US005874597A

United States Patent [19]
Jones

[11] Patent Number: 5,874,597
[45] Date of Patent: *Feb. 23, 1999

[54] CERTAIN AMINOSTEROL COMPOUNDS AND PHARMACEUTICAL COMPOSITIONS INCLUDING THESE COMPOUNDS

[75] Inventor: Steven Jones, West Chester, Pa.

[73] Assignee: Magainin Pharmaceuticals, Inc., Plymouth Meeting, Pa.

[*] Notice: The term of this patent shall not extend beyond the expiration date of Pat. No. 5,637,691.

[21] Appl. No.: 476,855

[22] Filed: Jun. 7, 1995

[51] Int. Cl.$^6$ .................................................... C07J 41/00
[52] U.S. Cl. .......................................................... 552/521
[58] Field of Search ............................... 552/521; 514/182

[56] References Cited

U.S. PATENT DOCUMENTS

| | | |
|---|---|---|
| 3,016,390 | 1/1962 | Counsell . |
| 3,370,070 | 2/1968 | Klimstra et al. . |
| 4,220,598 | 9/1980 | Hixson, Jr. et al. ........................ 424/1 |
| 4,372,888 | 2/1983 | Hjelmeland .......................... 260/397.1 |
| 4,425,273 | 1/1984 | Iida et al. .............................. 262/397.1 |
| 4,514,393 | 4/1985 | Castagnola et al. .................. 260/397.1 |
| 4,545,938 | 10/1985 | Mosbach et al. ...................... 260/397.1 |
| 4,550,163 | 10/1985 | Voss et al. ............................... 544/244 |
| 4,565,811 | 1/1986 | DiSchiena ............................... 514/182 |
| 4,771,042 | 9/1988 | Braughler et al. . |
| 4,793,948 | 12/1988 | Hatono et al. ........................ 260/397.1 |
| 4,966,897 | 10/1990 | Angelastro et al. .................... 514/177 |
| 4,994,443 | 2/1991 | Folkman et al. . |
| 5,001,116 | 3/1991 | Folkman et al. . |
| 5,004,737 | 4/1991 | Kim et al. . |
| 5,039,529 | 8/1991 | Bergendal et al. . |
| 5,057,509 | 10/1991 | Pellicciari et al. ...................... 514/182 |
| 5,061,701 | 10/1991 | Pellicciari et al. ...................... 514/182 |
| 5,063,222 | 11/1991 | Komoto et al. ......................... 514/180 |
| 5,075,464 | 12/1991 | Blohm et al. ........................... 552/522 |
| 5,135,919 | 8/1992 | Folkman et al. . |
| 5,192,756 | 3/1993 | Zasloff et al. . |
| 5,250,524 | 10/1993 | Kramer et al. . |

FOREIGN PATENT DOCUMENTS

| | | |
|---|---|---|
| 0394971 | 10/1990 | European Pat. Off. . |
| 0466315 | 1/1992 | European Pat. Off. . |
| 2361899 | 3/1978 | France . |
| 1565351 | 4/1980 | United Kingdom . |
| WO 87/02367 | 4/1987 | WIPO . |
| WO 91/19731 | 12/1991 | WIPO . |
| WO 93/25197 | 12/1993 | WIPO . |
| WO 94/19366 | 9/1994 | WIPO . |
| WO 94/20520 | 9/1994 | WIPO . |

OTHER PUBLICATIONS

Moriarty, R.M. et al., "Synthesis of Squalamine. A Steroidal Antibiotic from the Shark," *Tetrahedron Letters,* vol. 35, No. 44, 31 Oct. 1994, pp. 8103–8106.

K.S. Moore et al., "Squalamine: An aminosterol antibiotic from the shark," *Proc. Natl. Acad. Sci. USA,* vol. 90, Feb. 1993, pp. 1354–1358.

A.M. Bellini et al., "Antimicrobial Activity of basic Cholane Derivatives Part IX," *Arch. Pharm.* (Weinheim), vol. 323, 1990, pp.201–205.

A.M. Bellini et al., "Antimicrobial activity of basic cholane derivatives. X," *Steroids,* vol. 56, Jul. 1991, pp. 395–397.

J. McKenna et al., "Bis–steroids as Potential Enzyme Models," *J.C.S. Chem. Comm.,* 1977, pp. 809–811.

S.L. Wehrli et al., "Structure of the novel steroidal antibiotic squalamine determined by two–dimensional NMR spectroscopy," *Steroids,* vol. 58, No. 8, Aug. 1993.

A. Sadownik et al., "Rapid Construction of a Squalamine Mimic," *Journal of the American Chemical Society,* vol. 117, 1995, pp. 6138–6139.

R. Crum et al., "A New Class of Steroids Inhibits Angiogenesis in the Presence of Heparin or a Heparin Fragment," *Science,* vol. 230, Dec. 20, 1985, pp. 1377–1378.

W. Auerbach et al., "Angiogenesis Inhibition: A Review," *Pharmac. Ther.,* vol. 63, 1994, pp. 265–311.

A. Gagliardi et al., "Inhibition of Angiogenesis by Antiestrogens," *Cancer research,* vol. 53, Feb. 1, 1993, pp. 533–535.

*Primary Examiner*—Kimberly J. Prior
*Attorney, Agent, or Firm*—Finnegan, Henderson, Farabow, Garrett & Dunner, L.L.P.

[57] ABSTRACT

Aminosterol compounds are described that are useful as inhibitors of the sodium/proton exchanger (NHE). Methods of using such aminosterols compounds are also enclosed, including those employing compounds that are inhibitors of a spectrum of NHEs as well as those using compounds that are inhibitors of only one specific NHE. Advantageous screening techniques and assays for evaluating a compound's therapeutic activity are also disclosed.

5 Claims, 20 Drawing Sheets

CERTAIN AMINOSTEROL COMPOUNDS AND PHARMACEUTICAL COMPOSITIONS INCLUDING THESE COMPOUNDS

CROSS-REFERENCE TO RELATED APPLICATION

This application is related to U.S. Ser. No. 08/416,883, which is the U.S. national phase of International Application No. PCT/US94/10265, filed Sep. 13, 1994.

FIELD OF THE INVENTION

The present invention relates to aminosterol compounds useful as inhibitors of the sodium/proton exchanger (NHE). The invention is also directed to pharmaceutical compositions containing such compounds, and the use of such compounds for inhibiting NHE. The invention is further directed to assaying techniques for screening compounds for their efficacy as NHE inhibitors.

BACKGROUND OF THE INVENTION

Each of the body's cells must maintain its acid-base balance or, more specifically, its hydrogen ion or proton concentration. Only slight changes in hydrogen ion concentration cause marked alterations in the rates of chemical reactions in the cells—some being depressed and others accelerated. In very broad and general terms, when a person has a high concentration of hydrogen ions (acidosis), that person is likely to die in a coma, and when a person has a low concentration of hydrogen ions (alkalosis), he or she may die of tetany or convulsions. In between these extremes is a tremendous range of diseases and conditions that depend on the cells involved and level of hydrogen ion concentration experienced. Thus, the regulation of hydrogen ion concentration is one of the most important aspects of homeostasis.

A shorthand method of expressing hydrogen ion concentration is pH: $pH = \log 1/(H^+ \text{ concentration}) = -\log (H^+ \text{ concentration})$. The normal cell pH is 7.4, but a person can only live a few hours with a pH of less than 7.0 or more than 7.7. Thus, the maintenance of pH is critical for survival.

There are several mechanisms of maintaining pH balance. For example, during quiescence and constitutive growth, cells appear to utilize the chloride/bicarbonate exchanger, a well-studied device which provides for proton exchange across cells such as the red cell.

In addition, during accelerated periods of growth, which are induced by mitogens, growth factors, sperm, etc., cells engage another piece of cellular equipment to handle the impending metabolic burst. This is the sodium/proton ($Na^+/H^+$) exchanger—the "NHE," which is also called an "antiporter." Because the NHE functions in a number of roles and in a number of tissues, the body has developed a family of NHEs, and recent work has elucidated a family of NHE "isoforms" that are localized in certain tissues and associated with various functions. The NHE isoforms listed below are most likely to be significant.

NHE1 is a housekeeping exchanger and is believed to be unregulated in hypertension. It is thought to play a role in intracellular pH conduct. Also, it is believed that control of this exchanger will protect a patient from ischemic injury.

NHE1a is associated genetically with diabetes and, thus, inhibition might alter evolution of diabetes through effects on beta cells in the pancreas. In addition, vascular smooth muscle proliferation, responsive to glucose, is associated with increased expression of NHE1a.

NHE1β is present on nucleated erythrocytes. It is inhibited by high concentrations of amiloride. This NHE isoform is regulated by adrenergic agents in a cAMP-dependent fashion.

NHE2 is associated with numerous cells of the GI tract and skeletal muscle. Inhibition could alter growth of hyperplastic states or hypertrophic states, such as vascular smooth muscle hypertrophy or cardiac hypertrophy. Cancers of muscle origin such as rhabdomyosarcoma and leiomyoma are reasonable therapeutic targets.

NHE3 is associated with the colon. The work described below shows it to be associated with endothelial cells. Inhibition would affect functions such as water exchange in the colon (increase bowel fluid flux, which is the basis of, e.g., constipation), colonic cancer, etc. On endothelial cells, normal growth would be inhibited through inhibition of the exchanger.

NHE4 is associated with certain cells of the kidney. It appears to play a role in cellular volume regulation. Specific inhibitors might affect kidney function, and hence provide therapeutic benefit in hypertension.

NHE5 is associated with lymphoid tissue and cells of the brain. Inhibition of NHE5 should cause inhibition of proliferative disorders involving these cells. NHE5 is a likely candidate for the proliferation of glial cells in response to HIV and other viral infections.

As indicated by the above, although the NHE functions to assist the body, the inhibition of NHE function should provide tremendous therapeutic advantages. For example, although the NHE normally operates only when intracellular pH drops below a certain level of acidity, upon growth factor stimulation the cell's NHEs are turned on even though the cell is poised at a "normal" resting pH. As a consequence, the NHEs begin to pump protons from the cell at a pH at which they would normally be inactive. The cell undergoes a progressive loss of protons, increasing its net buffering capacity or, in some cases, actually alkalinizing. In settings where the pump is prevented from operating, the growth stimulus does not result in a cellular effect. Thus, inhibitors of the NHE family are likely to exert growth-inhibitory effects.

During severe acid stress—the condition that a tissue might find itself in when deprived of oxygen (or a blood supply)—the NHE family is believed to contribute to subsequent irreversible damage. For example, when blood flow to the heart is impaired, local acidosis occurs. Heart muscle cells develop a profound internal acidity. The acidity, in turn, activates otherwise dormant NHEs. These exchangers readily eliminate protons from the cell, but in exchange for sodium. As a consequence, intracellular sodium concentrations rise. Subsequently, the sodium-calcium exchanger is activated, exchanging internal sodium for external calcium. The rise in internal $Ca^+$ concentrations leads to cell death, decreased contractility, and arrhythmias. Thus, post ischemic myocardial damage and associated arrhythmias are believed to arise from an NHE-dependent mechanism, and inhibition of this NHE should therefore prevent such occurrences. If the NHE inhibited the internalization of $Na^+$ and slowed down metabolic activity as a consequence of the depressed pH, damage of the cell could be avoided. Hence, there is an interest in the development of NHE inhibitors for use in cardiac ischemia.

Other members of the NHE family appear to play a more classical role in water and sodium transport across epithelial surfaces. Specifically, the NHE3 isoform found in the colon is believed to play a role in regulating the fluid content of the colonic lumen. This pump is inhibited in cases of diarrhea. The NHE3 isoform present on the proximal tubules of the kidney is believed to play a similar role with respect to renal salt and acid exchange. Accordingly, inhibitors of the NHE family have been regarded as therapeutic modalities for the treatment of hypertension.

In view of the expected value of the inhibition of NHE action, scientists have sought out NHE inhibitors. The most widely studied inhibitor of NHE is amiloride, a guanidine-modified pyrazine used clinically as a diuretic. A number of derivatives have been generated, incorporating various alkyl substitutions. These derivatives have been studied with the several isoforms of NHE that are known and described above, except for NHE5, for which there is no known inhibitor.

The activities of these inhibitors against these specific exchangers have been previously determined. As seen in Table A below, each exchanger exhibits a different spectrum of response to each inhibitor:

TABLE A

|      | Amiloride $K_i$ ($\mu M$) | DMA $K_i$ ($\mu M$) | MPA $K_i$ ($\mu M$) |
| --- | --- | --- | --- |
| NHE1 | 3   | 0.1 | 0.08 |
| NHE2 | 3   | 0.7 | 5.0 |
| NHE3 | 100 | 11  | 10  |

Notes:
DMA = dimethylamiloride; MPA = methylpropylamiloride.
See Counillon et al., Molecular Pharmacology 44, 1993, 1041–1045.

The NHE inhibitors described by Counillon et al. exhibit specificity for NHE1. They therefore serve a therapeutic value in the treatment of conditions where inhibition of this isoform is beneficial. However, these inhibitors do not target the other known NHE isoforms—e.g., NHE3 is unaffected.

NHE3, as is demonstrated below, is expressed on endothelial cells, and its inhibition results in anti-angiogenic effects. The spectrum of NHE isoforms inhibited by the aminosterol compounds in accordance with the invention are different from those inhibited by the amiloride or the Counillon et al. compounds, and have different, distinct pharmacological effects.

In addition, Counillon et al. also reported that certain benzoylguanidine derivatives inhibit other NHE isoforms. In particular, (3-methylsulfonyl-4-piperidinobenzoyl) guanidine methanesulfonate exhibits particular selectivity to the NHE1 as shown in the table below.

TABLE B

| NHE Isoform | $K_i$ ($\mu M$) |
| --- | --- |
| NHE1 | 0.16 |
| NHE2 | 5.0 |
| NHE3 | 650 |

These benzoylguanadine compounds, which are based on the chemical structure of amiloride, exhibit greatest specificity for inhibiting NHE1 while retaining considerable activity against NHE2 and NHE3. To achieve pharmacological inhibition of NHE1, the widely distributed "housekeeping" isoform, undesirable inactivation of NHE2 and NHE3 would occur.

Those in the art have therefore continued to search for NHE inhibitors that exhibit selective action against a single, specific NHE. Such inhibitors would permit more precise inhibition of a tissue by perturbing the effect of the NHE on its growth.

Thus, artisans have recognized that the development of various NHE-specific inhibitors would allow for the development of new therapies for a whole host of diseases or conditions, including: treating arrhythmias; treating and preventing cardiac infarction; treating and preventing angina pectoris and ischemic disorders of the heart; treating and preventing ischemic disorders of the peripheral and central nervous system; treating and preventing ischemic disorders of peripheral organs and limbs; treating shock; providing anti-arteriosclerotic agents; treating diabetic complications; treating cancers; treating fibrotic diseases, including fibroses of lung, liver and kidney; and treating prostatic hyperplasia. Other therapeutic targets include: treatment of viral disease, such as HIV, HPV and HSV; prevention of malignancies; prevention of diabetes (i.e., islet cell injury); prevention of vascular complications of diabetes; treatment of disorders of abnormal neovascularization, e.g., macular degeneration, rheumatoid arthritis, psoriasis, cancer, malignant hemangiomas; prevention of vascular retenosis; prevention of hypertension-associated vascular damage; immunosuppression; and treatment of collagen vascular disorders.

Inhibitors of NHEs of bacteria fungi and protozoa would also be valuable as specific antimicrobials. It is known that all living cells use an NHE of one form or another to maintain intracellular $Na^+$ and pH homeostasis. NHEs have been cloned from numerous bacteria and fungi, and bear some sequence homology to the mammalian isoforms. Using a highly specific bacterial or fungal NHE as a target, it should be possible to develop a highly specific inhibitor of such an exchanger, one that is particularly advantageous or that lacks activity against the mammalian isoforms. Such compounds would be useful as antibiotics of a different mechanism.

Thus, there is a need in the art for specific inhibitors of NHEs. There is further a need to develop NHE inhibitors for various therapeutic uses.

SUMMARY OF THE INVENTION

The present invention fulfills needs felt in the art by providing various aminosterol compounds that inhibit various NHEs. The invention is directed to aminosterol compounds that exhibit inhibitory action on NHEs, and to compositions containing such compounds.

Thus, the invention is directed to newly isolated and synthesized aminosterol compounds that are useful as inhibitors of NHEs, such as compounds FX1A, FX1B, 1360, 1361, 371, 1437, and 353. Some of these steroid compounds have been found to inhibit a spectrum of NHEs, while others have been found to advantageously inhibit a single, specific NHE.

Further, the invention is directed to pharmaceutical uses and therapies employing the compounds of the invention. The invention is also directed to new uses for squalamine, which had been previously isolated and characterized.

Additionally, the invention is directed to advantageous screening methods for evaluating a compound's therapeutic efficacy. In particular, a tadpole assay has been developed, which has been found to be a convenient tool for screening compounds for NHE inhibition and therapeutic effects.

An especially preferred compound of the invention is compound 1436 (or a pharmaceutically acceptable salt thereof). The invention is directed to a pharmaceutical composition comprising an effective amount of this compound and a pharmaceutically acceptable vehicle or carrier. The invention is further directed to a method of inhibiting the proliferation of cells, comprising administering an effective amount of compound 1436, and particularly to such a method where the cells are malignant cells, vascular smooth muscle cells, bronchial smooth muscle cells, fibroblasts., lymphocytes or lymphoid tissue, muscle, bone, cartilage, epithelium, hematopoietic tissue, or neural tissue. Furthermore, the invention is directed to a method of inhibiting the proliferation of cells, comprising administering an effective amount of a combination comprising compound 1436 and squalamine. The invention also relates to a method for suppressing the immune system by inhibiting the proliferation of lymphocytes, comprising administering an effective amount of compound 1436. In addition, the invention involves suppressing the growth of a vertebrate, comprising administering an effective amount of compound 1436. The invention also relates to treating a viral infection by suppressing the growth of a viral target cell, comprising administering an effective amount of compound 1436. A method of controlling arterial pressure, comprising administering an effective amount of compound 1436, is also preferred. Also, the invention is directed to a method of protecting against cardiac ischemia, comprising administering an effective amount of compound 1436. The invention also relates to a method of preserving transplanted organs, comprising the administration of an effective amount of compound 1436. Furthermore, the invention is directed to a method of treating an infection caused by an microbial agent, such as bacteria, viruses, fungi, and protozoa, comprising the administration of an effective amount of compound 1436. The invention also pertains to the administration of an effective amount of this compound to inhibit an NHE.

The invention is also directed to a method of inhibiting NHE3, preferably to a method of specifically inhibiting this NHE isoform that is expressed in a pathological process, comprising the administration of an effective amount of squalamine (or its pharmaceutically acceptable salt). Another method according to the invention involves inhibiting the growth of endothelial cells, especially ones of new capillaries, comprising administering an effective amount of squalamine.

The invention also pertains to a or method for evaluating a compound for NHE-inhibiting activity or anti-angiogenic activity, comprising performing a tadpole assay comprising the steps of: (i) preparing an aqueous solution containing a compound to be assayed (e.g., at a concentration of 10 $\mu$g/ml); (ii) introducing a tadpole into the solution; and (iii) after at least one interval of time (e.g., about an hour), observing the tadpole (e.g., its tail and/or hands and feet) under a microscope. Preferably, the tadpole is a Xenopus tadpole, more preferably a stage 59–60 Xenopus tadpole. Such an assay can be used alone or in combination with another assay, e.g., a chick chorioallantoic membrane assay and/or a chick embryo vitelline capillary regression assay.

Other aspects, objects and advantages will be apparent from the detailed disclosure below, which illustrates preferred features and embodiments of the invention in conjunction with the appended drawing figures.

BRIEF DESCRIPTION OF DRAWING FIGURES

FIGS. 1A and 1B show the inhibition of rabbit sodium/proton exchanger isoform 3 (NHE3) by squalamine. FIG. 1A is a plot of the rate of pH recovery (y-axis) as a function of restored extracellular sodium ion concentration (x-axis) for cells acid preloaded by exposure to 40 mM $NH_4Cl$, with the curve marked by "+" being for control (no drug) and the curve marked by "Δ" being for squalamine. FIG. 1B shows the actual internal pH (y-axis) as a function of time (x-axis) following addition of 5 $\mu$g/ml of squalamine for cells not acid-preloaded.

FIG. 2A shows the lack of inhibition of rabbit sodium/proton exchanger isoform 1 (NHE1) by squalamine. FIG. 2B shows the lack of inhibition of human NHE1 by squalamine. In these plots of internal pH vs. time, the curve marked by "o" is for squalamine and that marked by "+" is the control (cells incubated in the absence of squalamin).

FIGS. 3A, 3B and 3C illustrate that endothelial cells exhibit greater sensitivity to squalamine (bar above 3 on the x-axis) than to other membrane-active agents, and that endothelial cells are more sensitive to squalamine than are epithelial cells and fibroblasts. FIG. 3A is for the administration of 1 $\mu$g/ml of the agent against bovine pulmonary endothelial cells, whereas FIGS. 3B and 3C are for administration of 10 $\mu$g/ml of the membrane-active agents to human epithelial cells and to human foreskin fibroblasts, respectively.

FIGS. 4, 4A, and 4, 4B-1, 4C, and 4C-1 show the suppression of the growth of murine melanoma, respectively through the subcutaneous, intraperitoneal and oral administration of squalamine.

FIG. 5 demonstrates the suppression of the growth of human melanoma 1205Lu in immunocompromised (RAG-1) mice by squalamine at various dosages ("o"=10 mg/kg/d, "+"=20 mg/kg/d, "●"=40 mg/kg/d; d=day).

DETAILED DESCRIPTION OF THE INVENTION

Syntheses of Aminosterol Compounds

The steroid known as squalamine is the subject of U.S. Pat. No. 5,192,756 to Zasloff et al., the disclosure of which is herein incorporated by reference. This compound is a broad-spectrum antibiotic, killing bacteria, fungi and protozoa. The absolute stereochemistry for squalamine, compound 1256, is shown below. The total chemical synthesis of squalamine was reported in 1994.

EXAMPLE 1

Preparation of Shark Liver Isolates

In addition to squalamine, at least ten other distinctly different aminosterols have been recovered from extracts of dogfish shark liver. To prepare the aminosterols, shark liver was extracted in methanol:acetic acid. The aqueous extract was adsorbed to C18 silica and eluted with 70% acetonitrile, and the eluate was adsorbed to SP-sephadex and eluted with 1.5M NaCl. The eluate was adjusted to 5M NaCl, and the steroids salted out. The precipitate was filtered over Celite and eluted with hot water, followed by methanol. The eluate was reduced in volume and applied to a 1-inch C18 column, and subjected to chromatography utilizing an increasing gradient in acetonitrile. Fractions were collected, concentrated by evaporation, and analyzed separately by thin layer chromatography (TLC).

Figure 9:
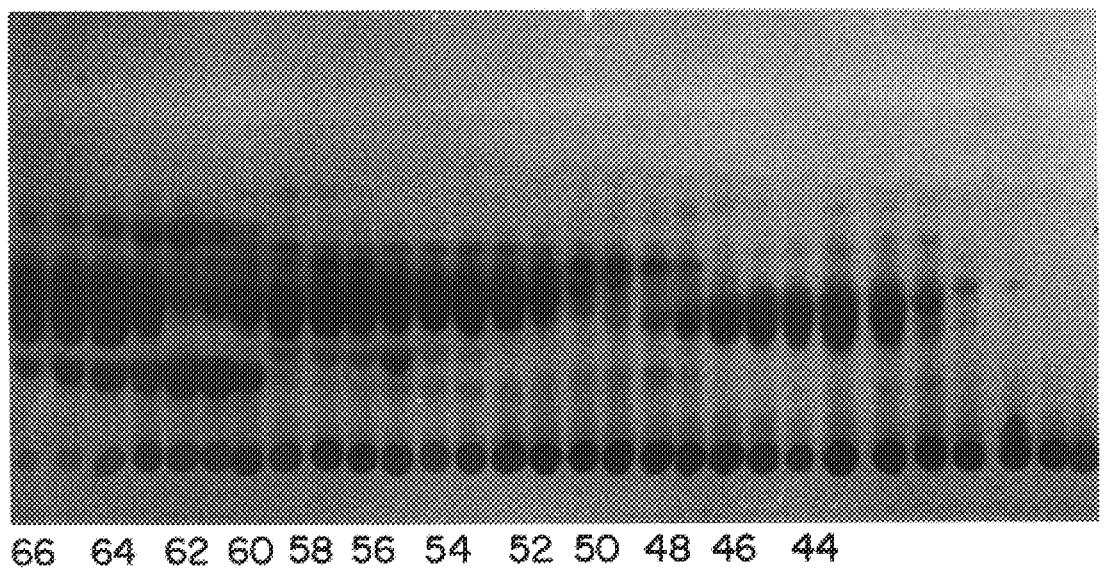
FIG. 9 is an HPLC profile for aminosterols derived from the liver of the dogfish shark, illustrating the diversity of these compounds.

The HPLC profile of the aminosterols isolated from 40 kg of shark liver is shown in FIG. 9. Final HPLC purification was performed as described in Moore et al., *Proc. Natl. Acad. Sci.* 90, 1993, 1354–1358. HPLC fractions were resolved individually by silica thin layer chromatography (6:3:1 $CH_2Cl_2$:MeOH:$NH_4OH$) visualized in iodine vapor. Fraction 40 represents the more hydrophilic portion of the elution profile, and fraction 66 represents the more hydrophobic portion.

Squalamine elutes beginning at about fraction 62 and continues until fraction 80. In addition, other steroids can be seen eluting between fractions 43–47 ($R_f$ 82), 53–55 ($R_f$ 1.02), 56–59 ($R_f$ 0.51), 57–62 ($R_f$ 0.96), 60–64 ($R_f$ 0.47) and 61–66 ($R_f$ 1.06), as described below in Table 1.

TABLE 1

Chemical and Structural Characterization of Aminosterols Isolated From Shark Liver

| FRACTION | TLC Rf | Compound No. | Mass |
|---|---|---|---|
| 43–47 | 0.82 | FX 1A | 664.5 |
|  |  | FX 1B | 641.5 |
| 53–55 | 1.02 | 1360 | 641.49 |
| 56–59 | 0.51 | FX 3 |  |
| 57–62 | 0.96 | 1437 | 657.52 |
| 60–64 | 0.47 | 1436 | 684.52 |
| 61–66 | 1.05 | 1361 | 543.48 |
| 63–80 | 1.0 | 1256 | 627.98 |

The structures for some of these compounds are shown below.

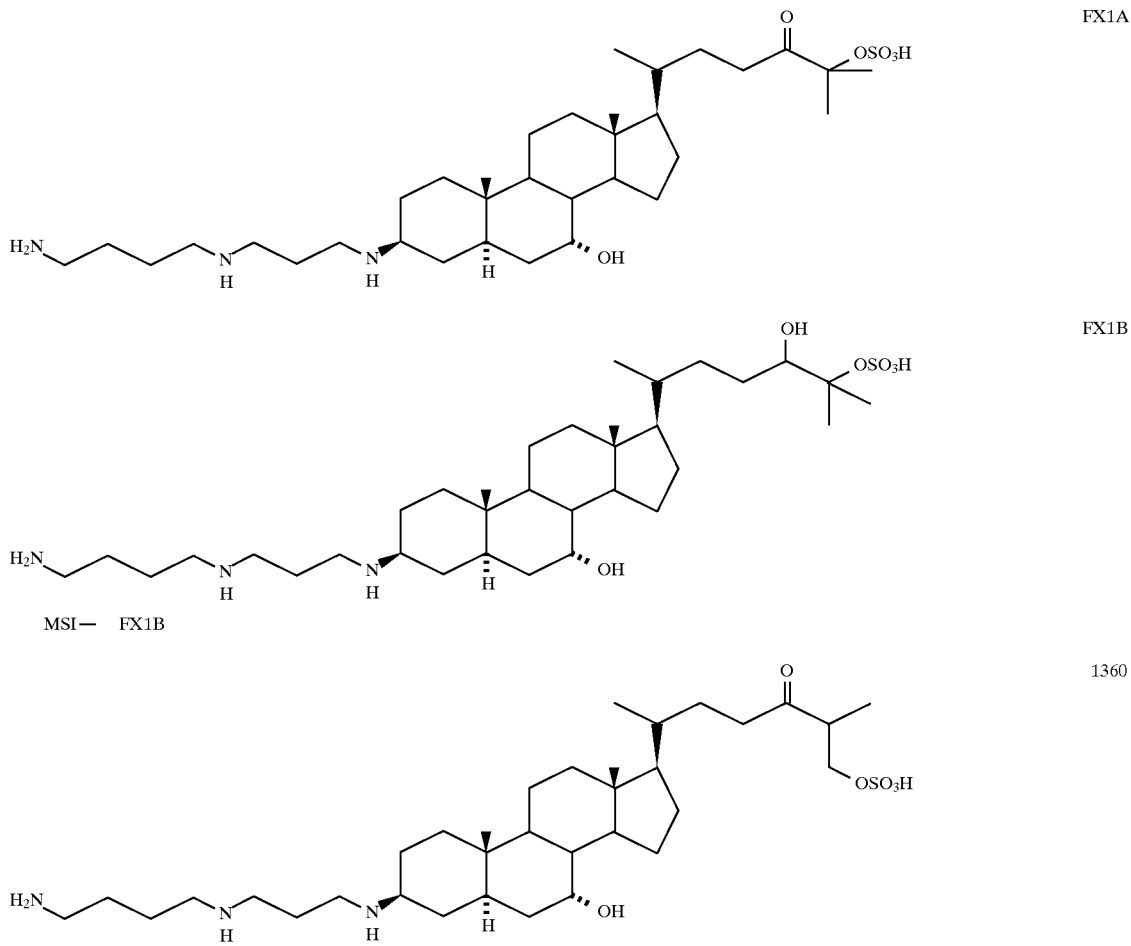

-continued

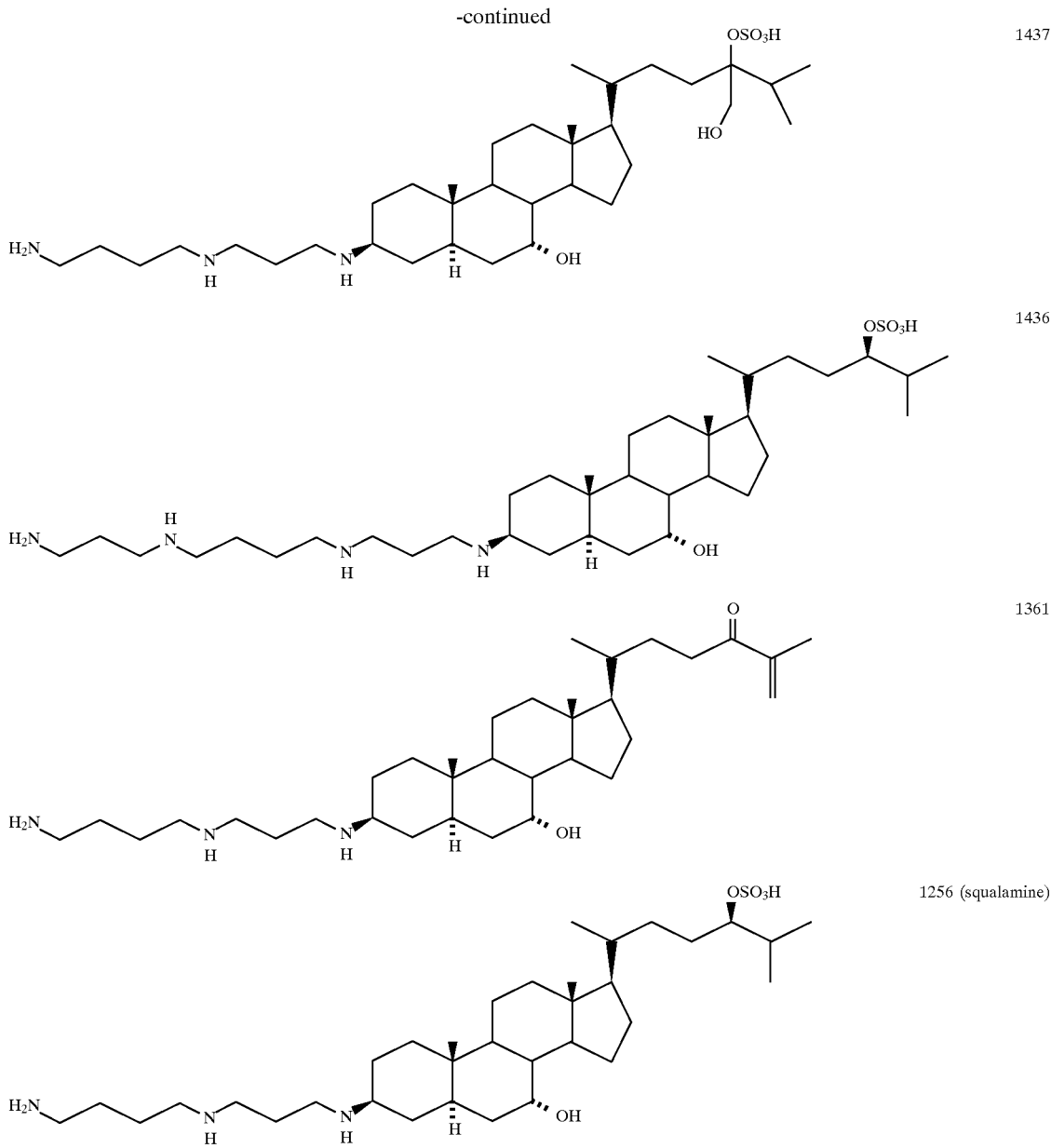

Each of these entities was isolated, purified, characterized, and the structure determined by NMR as described below.

Compound 1360:

This compound, the major steroid in Fraction 2 from preparative C18 RP-HPLC, was purified by strong cation exchange using sulfoethylaspartamide HPLC eluted with an increasing NaCl gradient. Steroid fractions were assayed by silica TLC developed in $CH_2C_2:CH_3OH:NH_4OH$ (6:3:1) and visualized with iodine. Steroid fractions were then pooled and re-chromatographed by C18 RP-HPLC with a gradient of increasing $CH_3CN$ in aqueous 0.1% TFA. TLC analysis of the purified compound showed a single spot with $R_f=1.02$ with respect to squalamine ($R_f$ squalamine=1.0).

For subsequent isolations of compound 1360, strong cation exchange chromatography was not performed. Instead, pooled fractions from preparative C18 RP-HPLC were subjected directly to C18 or C8 RP-HPLC using a shallower $CH_3CN$ gradient. Fractions were assayed both by TLC and also by $^1$H-NMR for samples redissolved in $D_2O$.

When analyzed by FAB-MS, the compound typically showed only a very weak (M+H)+ signal at 642.5 and an intense fragment at 562.5 daltons in the positive ion mode. In negative ion FAB-MS, (M−H)− was observed at 640.4. Subsequent electrospray ionization (ESI-MS) analysis exhibited strong (M+H)+ and (M−H)− signals consistent with a parent mass of 641.4, along with many TFA adducts. This suggested that lability of sulfate in compound 1360 was more pronounced under FAB conditions.

Since the parent ion in FAB positive ion mode was very weak in intensity, accurate mass determination was conducted on the dessulfate fragment. An accurate mass of 561.49325 was observed. An accurate parent mass of 641.49 daltons was then calculated by adding the mass of $SO_4$—, which matches with the molecular formula $C_{34}H_{63}N_3O_6S$. This molecular formula, with one additional oxygen and two fewer hydrogens when compared to squalamine ($C_{34}H_{65}N_3O_5S$), was suggestive of a compound bearing a carbonyl moiety.

$^1$H-NMR of compound 1360 in $D_2O$ (300 MHz) revealed several features distinguishing it from squalamine. For compound 1360, the resonance appearing furthest downfield at δ=4.15 ppm showed a splitting pattern of at least 7 signals with an integration of two protons; for squalamine, the most deshielded resonance at δ=4.2 ppm was the sulfate position (H24), resolved at 300 MHz as a multiplet of 5 signals with an integration of one proton. At 2.6 ppm, compound 1360 also showed a poorly resolved multiplet, attributed to 2 protons. It was suspected that these resonances could be attributed to methylene protons alpha to a carbonyl, based on comparison to the literature. In squalamine the region from 2.2–2.75 exhibited no resonances. Compound 1360 showed two distinct methyl doublets, one at 0.95 ppm and the other at 1.1 ppm; this contrasts with squalamine, where three methyl groups split as doublets overlapping in the 0.9–1.05 ppm region. Other resonance characteristics were quite similar for the two steroids. In the upfield methyl region, both compound 1360 and squalamine showed annular singlet methyl signals at 0.85 and 0.65 ppm, positions 19 and 18 respectively. The resonances from the steroid nucleus (1.0–2.1 ppm) and from spermidine also showed the same characteristic pattern for both compound 1360 and squalamine. H7, at the alcohol position in the ring, resonates at 3.85 ppm for both steroids in $D_2O$ A COSY (correlated spectroscopy) spectrum conducted in $D_2O$ (300 MHz) established the sulfate at position 27, —$CH_2OSO_3$—. Diagnostic crosspeak patterns in the 2-dimensional frequency (2D) plot indicated that the doublet peak at δ=1.1 ppm was methyl 26, which then connected to H25 at 3.05 ppm (hidden under the polyamine resonances), which in turn was the nearest neighbor to the complex multiplet at 4.15 ppm.

The polyamine region in the 2D map was consistent with the splitting pattern of spermidine, confirming that compound 1360 had the same polyamine as squalamine. Otherwise, the 2D map in $D_2O$ was deficient in many crosspeak signals, particularly in the steroid nucleus region, and could not be used to established the complete primary structure.

Compound 1360 was dried in vacuo and dissolved in DMSO-d6 under nitrogen, and then sealed under nitrogen using cycles of freeze-thaw-pump. Both ID and 2D $^1$H-NMR spectra were conducted at 300 MHz and at 600 MHz. All of the proton resonances of the compound in DMSO were sharp (except for the polyamine region (2.8–3.1)) and shifted with respect to assignments in $D_2O$. For example, the multiplet for position 27 was shifted upfield to 3.77 ppm and the H7 proton shifted to 3.60 ppm. In addition, a new doublet signal (integration=1H) appeared at 4.17 ppm. This new resonance was identified as the hydroxyl at position 7, based on its 2D connectivity to H7, which was unambiguous at 600 MHz. This resonance could not be observed in $D_2O$ due to its rapid exchange with solvent. The 2D map of compound 1360 in DMSO reconfirmed the location of the sulfate group at position 27, which was first deduced from the 2D COSY map in $D_2O$.

A careful comparison of 2D COSY maps for compound 1360 and squalamine suggested the presence of a carbonyl at position 24. The multiplet centered at 2.5 ppm (2.6 ppm in $D_2O$) with integration of 2 protons gave strong crosspeaks that identified these resonances as H23a,b (located alpha to a carbonyl at position 24) and with nearest neighbor connections to H22a,b. In a total correlation spectroscopy experiment (TOCSY), a new crosspeak was discernible as H22/H21, due to propagation of magnetization along the tail of the steroid. Noticeably absent from the 2D COSY and TOCSY maps were signals that would allow propagation of the magnetization from positions 23 to 24 and then from 24 to 25. Unlike the COSY of squalamine, which shows nearest neighbor crosspeaks for 22-23-24-25-26/27, compound 1360 showed an interruption in connectivity, suggesting that a functional group at position 24 blocked transfer of the proton signal. The structure can be verified by reducing C=O to an alcohol, however, since an alcoholic group at position 24 would allow for complete proton connectivity from positions 21–26 and 27.

$^{13}$C-NMR of compound 1360 in DMSO indicated 34 carbon signals. In comparison to squalamine, compound 1360 has one carbonyl at 212 ppm (C24). C27 resonated at 67 ppm, which is in good agreement with values reported for scymnol sulfate.

Compound 1361:

Compound 1361 was isolated from shark liver preparations in two different ways: first, as a degradation product of compound 1360; and, subsequently, as a minor aminosterol component fractionating with slightly faster retention time than squalamine during preparative C18 RP-HPLC (component of Fraction VI). In early attempts to purify each aminosterol to homogeneity, pooled fractions from C18 RP-HPLC were subjected to silica gel flash chromatography with $CH_2Cl_2$:$CH_3OH$:$NH_4OH$ 6:3:1, and the aminosterols were assayed on TLC plates. The pools of free base steroids were then re-subjected to C18 RP-HPLC, using an analytical column. The RP-HPLC elution profile showed two major steroids—compound 1360 and a second, more hydrophobic steroid eluting at higher % $CH_3CN$. The lability of the sulfate at position 27 in compound 1360 led to the formation of compound 1361, apparently through base-catalyzed elimination.

Hallmark features of the H spectrum for compound 1361 in $D_2O$ (400 MHz) included the absence of multiplet at δ=4.15 ppm corresponding to methylene protons at position 27, bearing the sulfate. Two new singlet protons at δ=5.95 and 6.15 in $D_2O$, each with integration values of 1H, were identified as vinyl protons. Also,. in contrast to the methyl doublet at δ=0.9 ppm in compound 1360, the new steroid showed a singlet methyl at δ=1.8 ppm, characteristic of an allylic methyl. The chemical shifts for the vinyl groups and for the allylic methyl compare favorably with literature values. Otherwise, the $^1$H spectrum showed features characteristic of compound 1360, including the presence of methylene signals at δ=2.75 ppm, alpha to carbonyl at position 24. The polyamine regions exhibited splitting patterns like that of squalamine, confirming the spermidine adduct.

An accurate mass of 543.4823 was measured by FAB-MS (positive ion mode). The molecular formula $C_{34}H_{61}N_3O_2$ has a calculated mass of 543.4842, in good agreement with the experimentally observed value. This molecular formula for compound 1361 is consistent with elimination of sulfate from the parent molecule, compound 1360. Moreover, the molecular formula for compound 1361 has a double bond equivalent (DBE) of 5.5, in comparison to 5.0 for compound 1360 and 4.0 for compound 1256; this DBE value is consonant with the additional unsaturation in compound 1361.

Compound 1436:

This compound and the steroids described below were purified by subjecting fractions from preparative C18 RP-HPLC to shallower CH3CN gradient conditions on smaller C18 columns. Although strong catiorL exchange chromatography and silica gel (SG) flash chromatography followed by RP-HPLC had been used in the purification of compounds 1360 and 1361, these protocols were not used when the pH lability was recognized.

Although compound 1436 elutes from C18 RP-HPLC with retention time only slightly faster than squalamine, its $R_f$=0.47 on TLC hints of a chemical structure with significantly greater polarity than squalamine under alkaline conditions ($CH_2Cl_2$:$CH_3OH$:$NH_4OH$ 6:3:1).

The $^1H$ NMR spectrum in $D_2O$ (400 MHz) revealed the polyamine regions differing from that of squalamine. Both the splitting pattern and integration resembled spermine rather than spermidine, i.e. N,N'-bis-3-aminopropyl-1,4-butane-diamine rather than N-(3-aminopropyl)-1,4-butanediamine. Otherwise, the $^1H$ spectrum appeared identical to that of squalamine: one proton at δ=4.15, the 24 sulfate position; one proton at δ=3.85, corresponding to H7 alcoholic ring position; three overlapping doublets in 0.85–0.95 ppm corresponding to methyl 21 and methyls 26 and 27. The identity of spermine was supported by performing COSY in $D_2O$, comparing crosspeak patterns to that of reference standards of spermine ($C_{10}H_{26}N_4$) and spermidine ($C_7H_{19}N_3$) as well as to that of squalamine in $D_2O$. Although COSY spectra of the aminosterols generally do not give a complete 2-dimensional map of crosspeaks in $D_2O$ and therefore cannol be relied on for complete nearest neighbor assignments, the polyamine region did produce a complete set of off-diagonal crosspeaks, which served reliably as the signature pattern for discerning between spermidine and spermine.

The $^{13}C$ spectrum of compound 1436 showed 3 additional signals in $D_2O$, but otherwise the carbon skeleton of the steroid was the same as for squalamine in $D_2O$. DEPT-135 (distortionless enhanced polarization transfer) was conducted such that methyl and methine signals were phased as positive signals, methylene groups as negative signals, and quaternary carbons gave zero intensity. DEPT-135 of the compound demonstrated that these 3 additional signals were methylenes (negative).

The molecular formula of $C_{37}H_{72}N_4O_5S$ has a calculated mass of 684.53017, in good agreement with the experimentally observed accurate mass of 684.5216 measured by high resolution FAB-MS (positive ion mode). The additional mass of 58 daltons (684.5 versus 627.5 for squalamine) was consistent with the presence of an extra 3-aminopropyl group attributed to spermine. Furthermore, the even number mass for the parent ion is consonant with the nitrogen rule, which predicts a compound having an even number of nitrogens. FAB-MS also showed fragmentation into species both 80 and 98 mass units less than the (M+H)+ parent at 685 amu (atomic mass units). These fragments represent loss of sulfate followed by dehydration, paralleling the structural lability of squalamine under FAB-MS conditions.

Compound 1436 was also synthesized from compound 1256 (squalamine) according to the following reaction scheme:

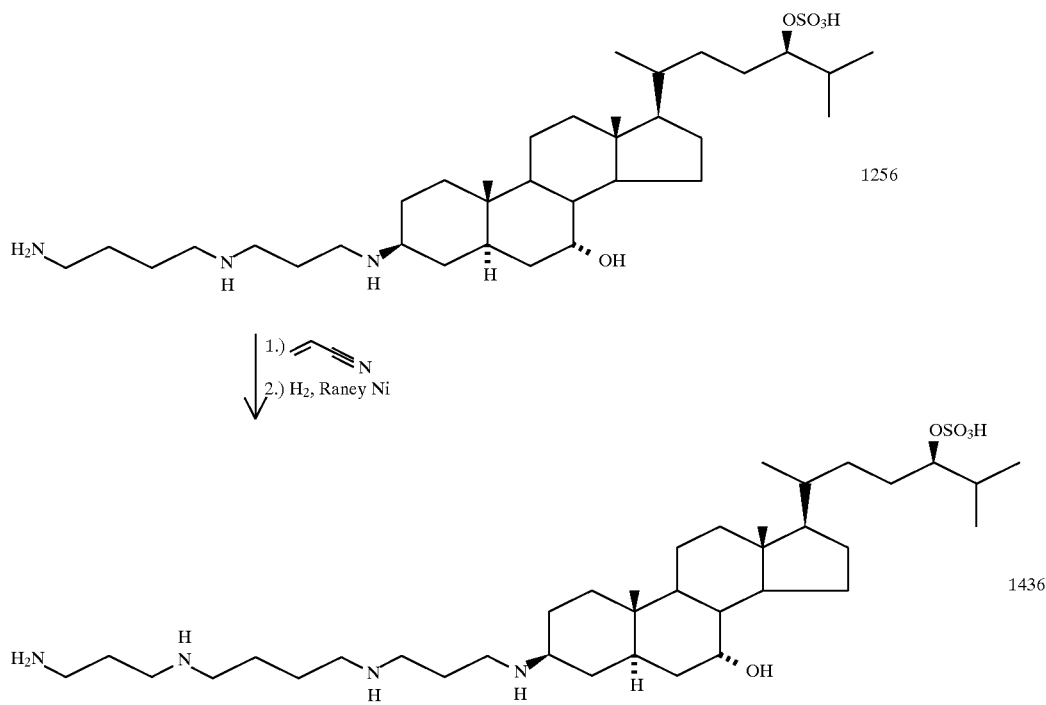

Into a round-bottom flask was introduced 95 mg (0.106 mmol) of squalamine (TFA salt), which was dissolved in 800 μl of anhydrous methanol. To the mixture was added 118 μl (0.848 mmol) of triethyl amine, followed by 100 μl (0.106 mmol) of diluted acrylonitrile solution (70 μl acrylonitrile diluted to 1000 μl in methanol). After 6 hours, a further 40 μl (0.042 mmol) of the dilute acrylonitrile solution was added. After 24 hours, TLC showed the presence of starting material and a product with $R_f$=0.7 (squalamine $R_f$=0.5). The reaction was stopped, and the product isolated by flash chromatography (12:3:1 to 6:3:1 $CH_2Cl_2$:MeOH:$NH_4OH$).

The product, although homogenous by TLC, appeared to be a mixture by NMR spectroscopy. The product thus obtained was added to a hydrogenation flask along with 10 mg of Raney nickel, 7.3 mg of sodium hydroxide and 5 ml of absolute ethanol, and hydrogenated at 40 psi for 17 hours. Two products, now separable (flash chromatography, 6:3:1 $CH_2Cl_2$:MeOH:$NH_4OH$), were seen on TLC, wherein the lower spot co-spotted with the reference (naturally isolated compound 1436). This product was separated by reverse-phase chromatography to yield 1.5 mg of pure material. This compound had a positive mass (M+1) Lon of 685, and its $^1$H and $^{13}$C NMR spectra were identical to those of the naturally isolated material, thus confirming its characterization and structure.

Compound 1437:

This steroid, eluting immediately after compound 1360 in preparative C18, exhibits $R_f$=0.96 on TLC, reflecting a more polar character than squalamine itself. $^1$H NMR (400 MHz) in $D_2O$ appeared essentially identical to squalamine for the methyl region, steroid nucleus and spermidine region, and 7H at the ring hydroxyl position. Conspicuously absent from the $^1$H spectrum was the multiplet at $\delta$=4.15 ppm corresponding to one proton at the 24-sulfate position. Instead, a new signal centered at $\delta$=3.95 was observed with the characteristic gem alcohol coupling and integration for 2 protons.

When compared to squalamine, the 13C spectrum of compound 1437 in $D_2O$ revealed only two noticeable changes. One new signal appeared at $\delta$=72 ppm, which was subsequently identified as a —CH$_2$OH group since its DEPT-135 signal was negative. In squalamine, the sulfate position was identified at $\delta$=86 ppm as a primary carbon (positive DEPT-135 signal). For compound 1437, however, this carbon resonance for the sulfate position shifted to 76 ppm and gave no DEPT-135 signal, thereby identifying it as a quaternary carbon. The aminosterol structure consistent with these data has the carbon skeleton of ergostanol, with carbon 24 bearing the sulfate and carbon 24' being the alcohol.

FAB-MS in positive ion mode indicated (M+H)+ at 658.6, fragmenting to 578.6 due to loss of sulfate; negative ion mode analysis confirmed a pseudomolecular parent ion (M–H)– at 656.4. An accurate mass of 578.5264 was determined on the dessulfate fragment, on account of the low intensity of the parent signal. The accurate mass of the parent ion could then be calculated as 657.526 (by adding the mass of sulfate). Compound 1437 is thus 30 daltons greater than squalamine, which could be explained by an additional -CH$_2$OH moiety.

Steroids in Fraction I:

Fraction I (FX1) is the earliest steroid fraction eluting from preparative Cl8 RP-HPLC. TLC analysis typically showed a single major spot with $R_f$=0.80–0.84 (with respect to squalamine, $R_f$=1.0) and protein which stayed at the TLC origin. If the TLC plates were run with concentrated samples ($\geq$3 mg/ml), hints of additional spots, with $R_f$ values either slightly greater than or less than the major component, were discernable.

When subjected to high resolution RP-HPLC using C18 columns with 60–100 Å pore size and very shallow CH$_3$CN gradients, Fraction I could be separated into as many as 7 components, designated I-1, I-2, I-3, I-4, I-S, I-6, and 1-7. Steroids FX1A, FX1B, FX1C, FX1D are presented as possible structures:

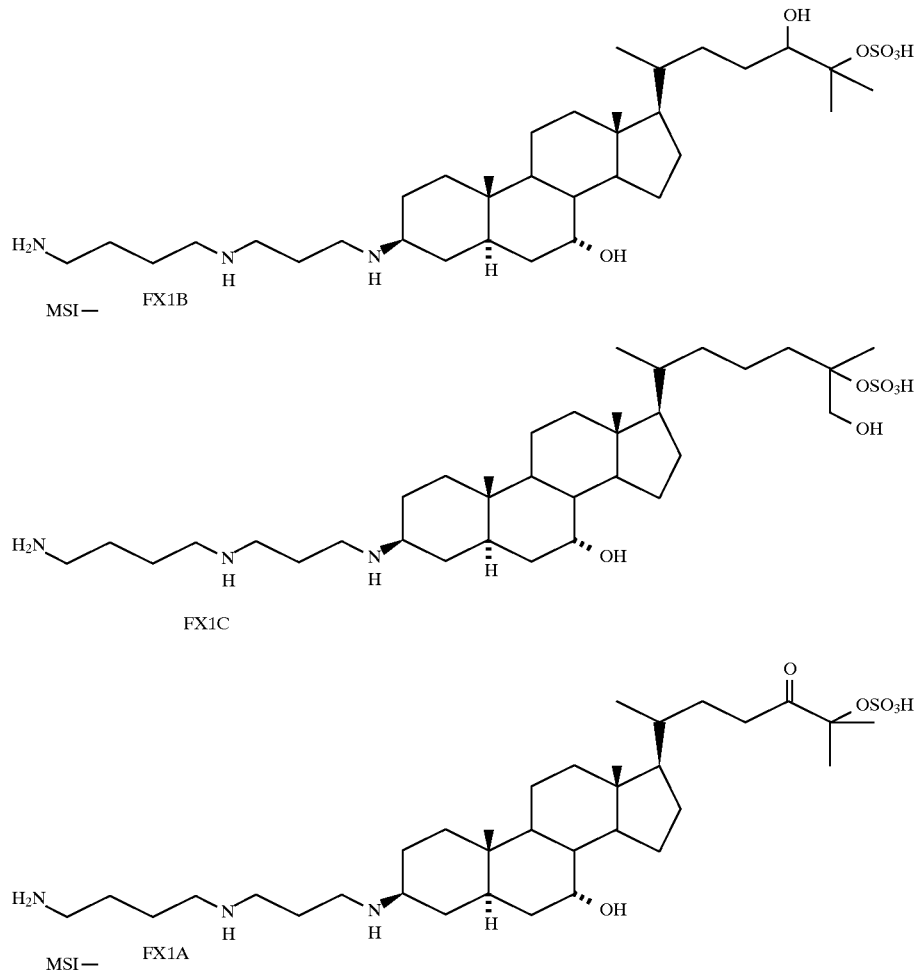

-continued

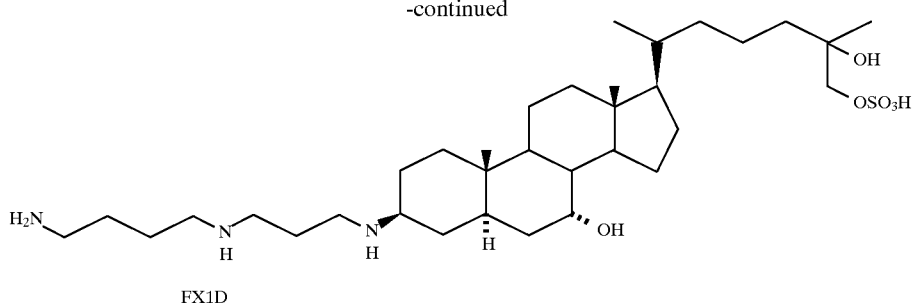

FX1D

EXAMPLE 2

Synthesis of Aminosterols

In addition to the above compounds, which were isolated from shark liver, synthetic aminosterol compounds have been developed. Various polyaminosterol compounds, including those specified in Examples A–G, are described in U.S. Ser. No. 08/416,883, which is the U.S. national phase of International Application No. PCT/US94/10265, filed Sep. 13, 1994, the disclosure of which is herein incorporated by reference. Compounds exemplified therein include the following:

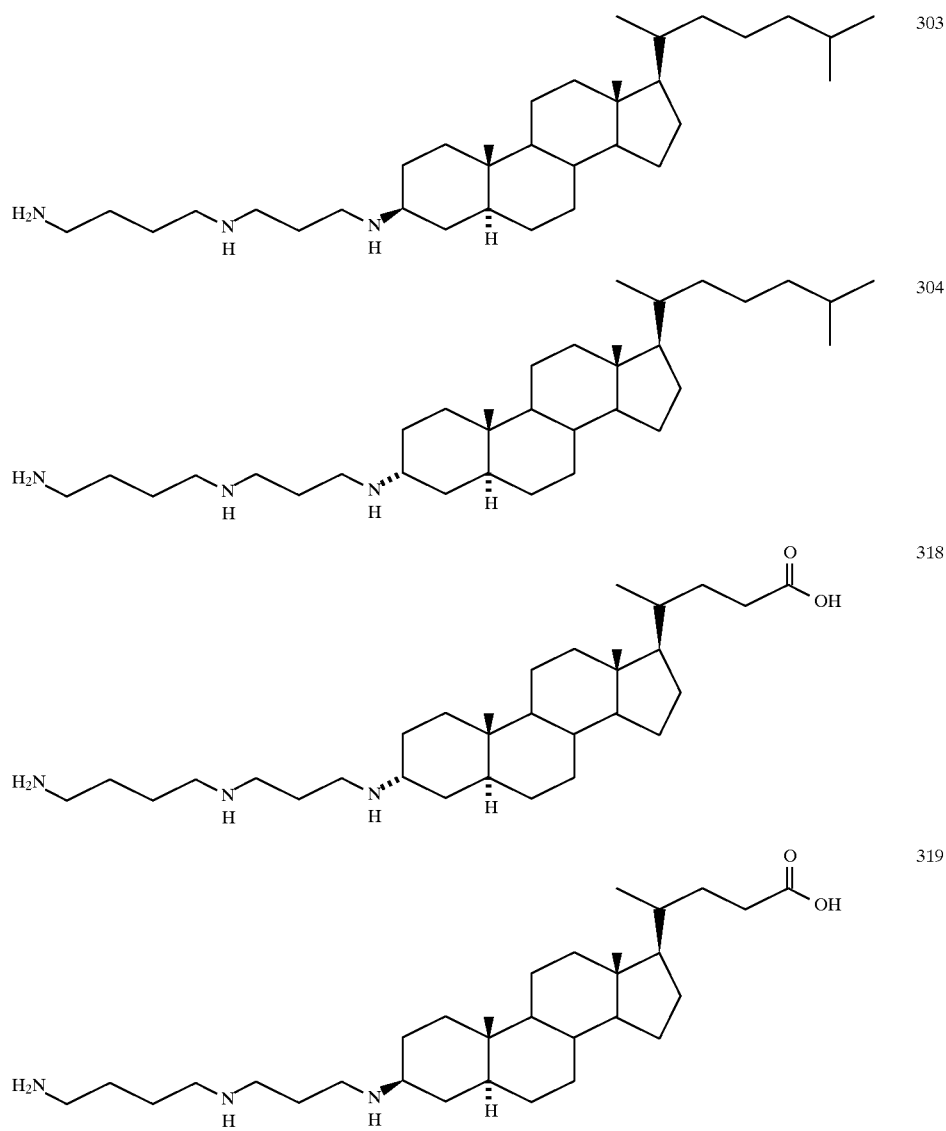

Additional aminosterol compounds have now been developed. Preferred compounds of the invention include those exemplified below.

EXAMPLE H

Preparation of compound 353 and compound 354:

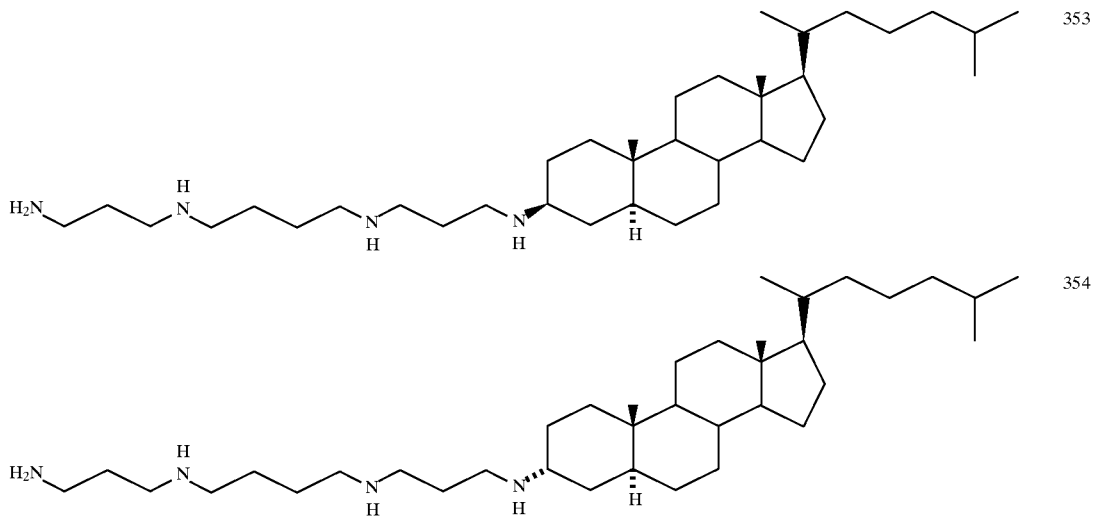

The above compounds were prepared by reductive coupling of 5α-cholestan-3-one to spermine (4 equivalents) with sodium cyanoborohydride in a manner analogous to the preparation of compound 303. Purification was achieved on silica gel (gradient elution with 9:3:1 to 3:3:1 chloroform:methanol:isopropylamine). Compound 353 (more polar) and compound 354 (less polar) were converted to their hydrochloride salts in the same manner as for compound 303. α-Amino compound 354: $^1$H NMR (200 MHz, CD$_3$OD) δ: 3.47 (m, 1H), 3.3–2.9 (m, 12H), 2.3–1.0 (m, 39H), 1.0–0.8 (m, 12H), 0.70 (s, 3H); IR (KBr, cm$^{-1}$): 3396, 2934, 1594, 1457, 1383; MS(+FAB): 573.6 (M+1); Anal. calcd. for C$_{37}$H$_{72}$N$_4$—4HCl—H$_2$O: C=60.31, H=10.67, N=7.60; Found: C=60.01, H=10.83, N=7.67. β-Amino compound 353: $^1$H NMR (200 MHz, CD$_3$OD) δ: 3.3–3.0 (m, 13H), 2.2–1.0 (m, 39H), 1.0–0.8 (m, 12H), 0.70 (s, 3H); IR (KBr, cm$^{-1}$): 2945, 1596, 1466, 1383; MS exact mass (+FAB) calcd.: 573.5835; Found: 573.5801; Anal. calcd. for C$_{37}$H$_{72}$N$_4$—4HCl—H$_2$O: C=58.87, H=10.68, N=7.42; Found: C=58.49, H=10.94, N=7.94.

Compound 353 is a simple adduct of spermine and cholestanol, representing a very inexpensive compound. It can be synthesized like compound 354 in the following straightforward manner:

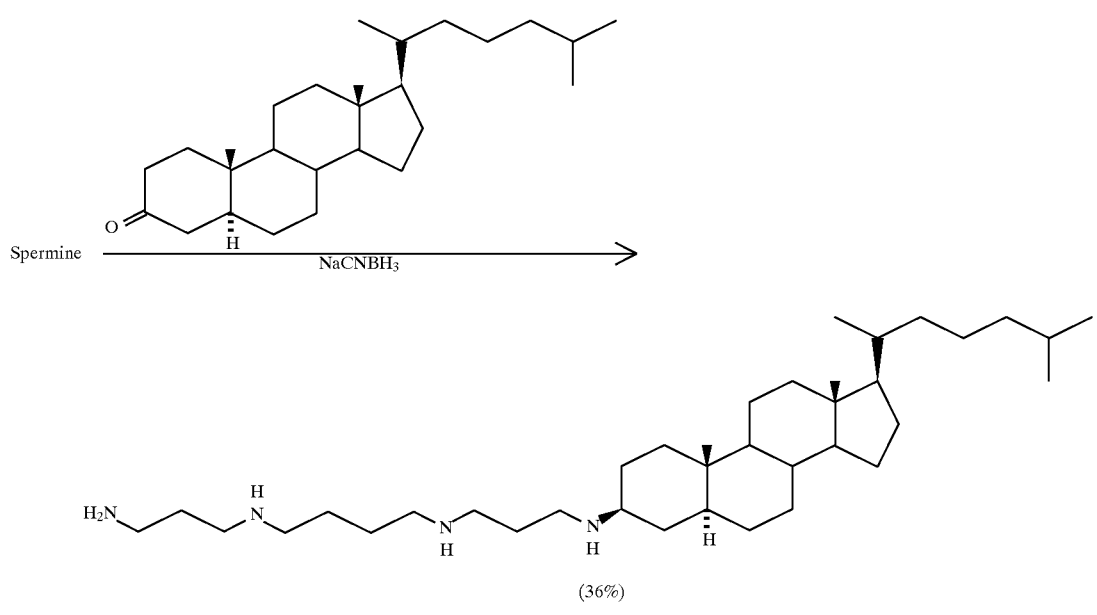

-continued

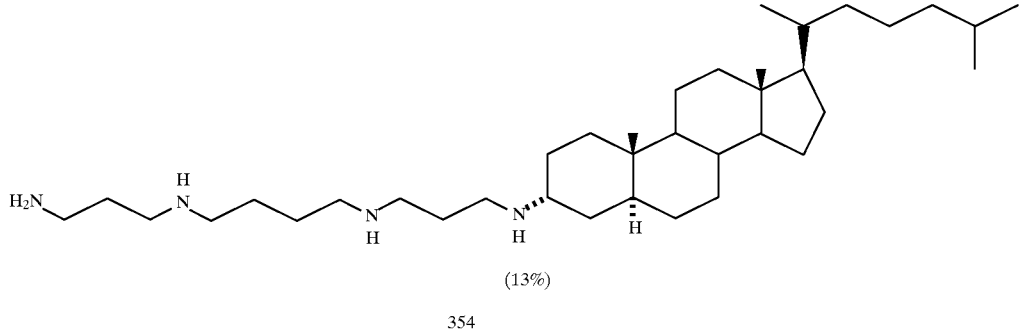

(13%)

354

EXAMPLE I

Preparation of compound 458 and compound 459:

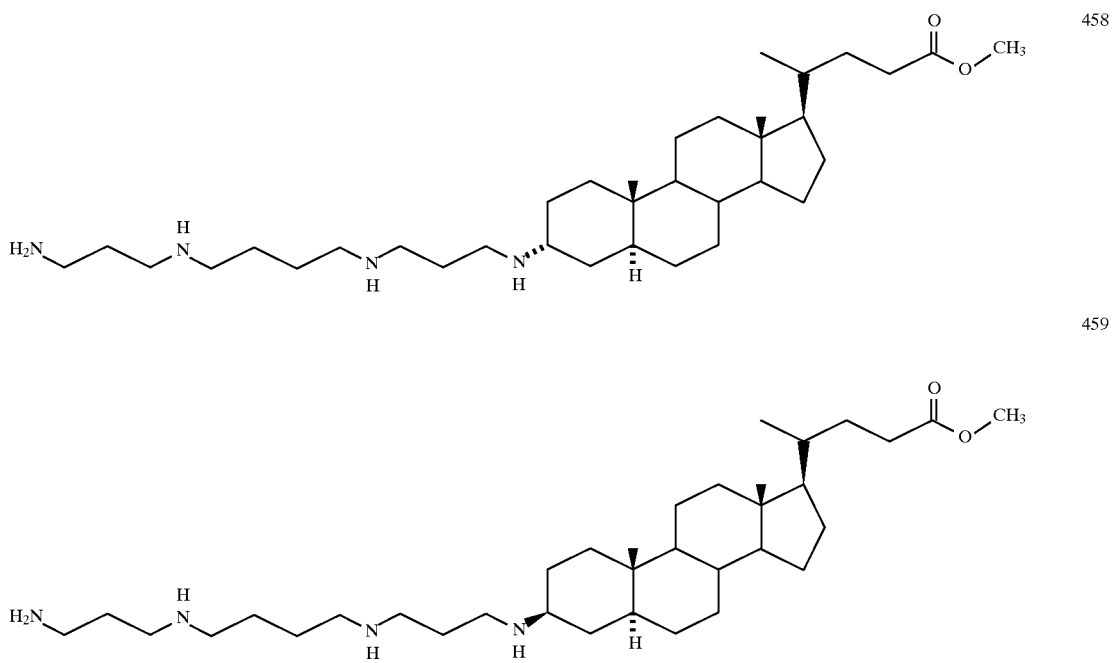

The above compounds were prepared from methyl 3-oxo-5α-cholanoate and spermine (1.35 equivalents) as in the synthesis of compound 353. Purification on silica gel (gradient elution with 6:3:1 to 3:5:2 chloroform:methanol:isopropylamine) afforded the less polar α-amino compound 458 and the more polar β-amino compound 459. These compounds were converted to their hydrochloride salts as done as for compound 303. Compound 458: $^1$H NMR (400 MHz, CD$_3$OD) δ: 3.64 (s, 3H), 3.45 (m, 1H), 3.25–3.05 (m, 12H), 2.4–1.0 (m, 36H), 0.93 (d, J=6 Hz, 3H), 0.87 (s, 3H), 0.70 (s, 3H); IR (KBr, cm$^{-1}$): 2943, 1741, 1458, 1169; MS(+FAB): 575.6 (M+1); Anal. calcd. for C$_{35}$H$_{66}$N$_4$O$_2$—4HCl—1.2H$_2$O: C=56.63, H=9.83, N=7.55; Found: C=56.58, H=9.46, N=7.29. Compound 459: $^1$H NMR (400 MHz, CD$_3$OD) δ: 3.63 (s, 3H), 3.2–3.0 (m, 13H), 2.4–1.0 (m, 36H), 0.92 (d, J=6 Hz, 3H), 0.86 (s, 3H), 0.69 (s, 3H); IR (KBr, cm$^{-1}$): 2942, 1739, 1595, 1459, 1382, 1170; MS(+FAB): 575.6 (M+1); Anal. calcd. for C$_{35}$H$_{66}$N$_4$O$_2$—4HCl—1.4H$_2$O: C=56.35, H=9.84, N=7.51; Found: C=56.35, H=9.26, N=7.67.

EXAMPLE J
Preparation of compounds 380, 381, 382 and 394:

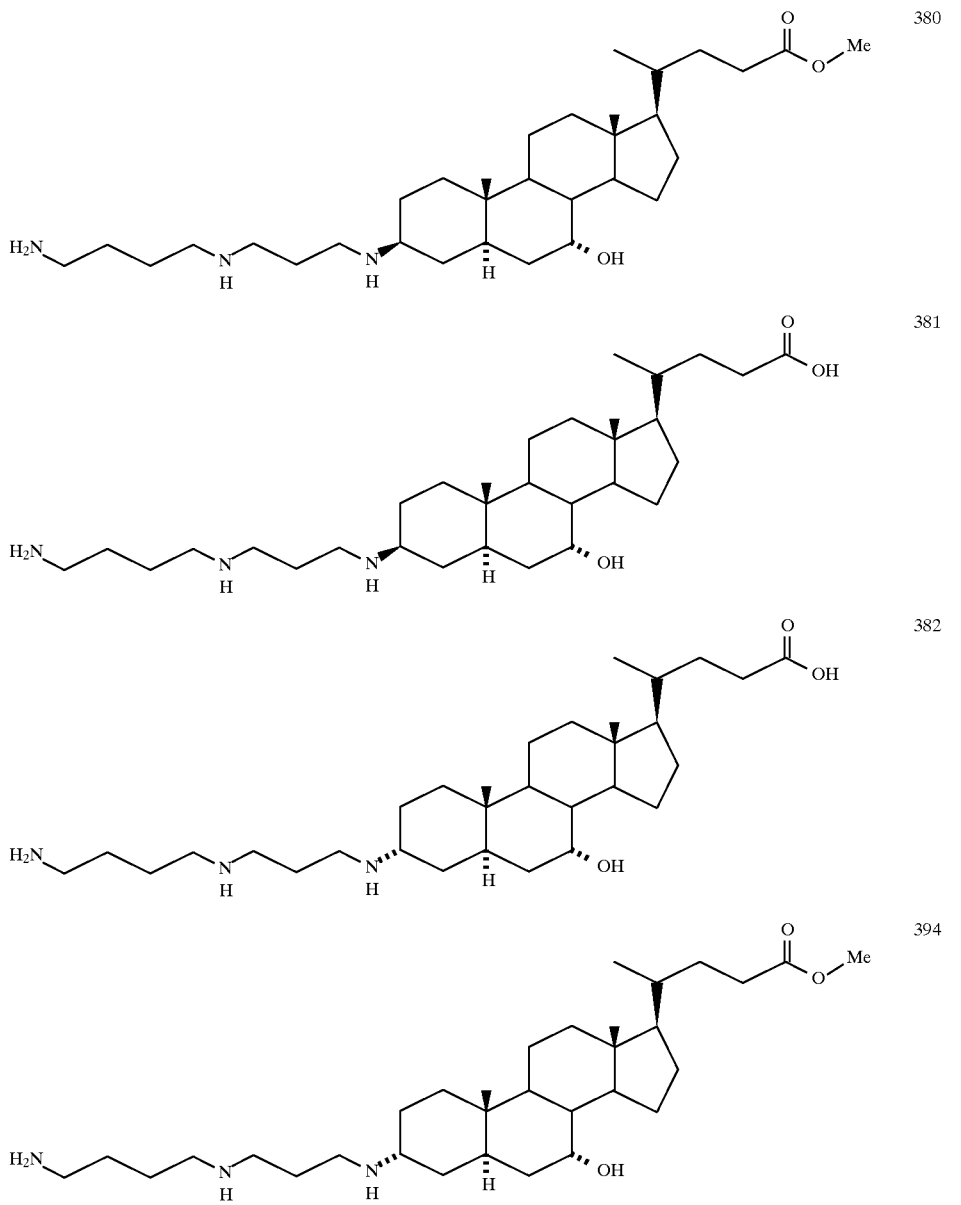

The steroid methyl 7α-hydroxy-3-oxo-5α-cholanoate was prepared according to the method of Iida et al., *Chem. Pharm. Bull.* 41(4), 1993, 763–765. This steroid was coupled to the polyamine compound 301 with sodium cyanoborohydride, the BOC groups were removed with trifluoroacetic acid, and the ester was hydrolyzed as in the preparation of compound 319, except that lithium hydroxide was used as the base. Purification was achieved on silica gel (15:4:1 to 10:4::1. chloroform:methanol:isopropylamine). Compounds 381 and 382 were treated with 2M ammonia in methanol and evaporated (3×20 ml) to drive off isopropylamine. The hydrochloride salt was prepared as for compound 303.

Compound 380, $C_{32}H_{59}N_3O_3$: $^1H$ NMR (200 MHz, $CDCl_3$) δ: 3.83 (br s, 1H), 3.66 (s, 3H), 2.8–2.4 (m, 9H), 2.3–1.0 (m, 32H), 0.92 (d, J=6 Hz, 3H), 0.78 (s, 3H), 0.65 (s, 3H); IR (KBr, cm$^{-1}$): 3278, 2928, 1736,. 1447, 1163; MS(+FAB): 534 (M+1).

Compound 381, $C_{31}H_{57}N_3O_3$—1.7 $H_2O$; $^1H$ NMR (200 MHz, $CD_3OD$) δ: 3.80 (br s, 1H), 3.0–2.5 (m, 9H), 2.2–1.1 (m, 32H), 0.94 (d, J=6 Hz, 3H), 0.84 (s, 3H), 0.69 (s, 3H); IR (KBr, cm$^{-1}$): 3380, 2929, 1560, 1395; MS(+FAB) calcd.: 520.4478 (M+1); Found: 520.4506; Anal. calcd.: C=67.64, H=11.06, N=7.63; Found: C=67.64, H=10.24, N=7.83.

Compound 382, $C_{31}H_{57}N_3O_3$—2$H_2O$: $^1H$ NMR (200 MHz, $CD_3OD$) δ: 3.80 (br s, 1H), 3.15 (br s, 1H), 3.1–2.6 (m, 8H), 2.2–1.1 (m, 32H), 0.96 (d, J=6 Hz, 3H) , 0.85 (s, 3H) , 0.69 (s, 3H) ; IR (KBr, cm$^{-1}$) 3416, 2930, 1560, 1395; MS(+FAB) calcd.: 520.4478 (M+1); Found: 520.4489; Anal. calcd: C=66.99, H=11.06, N=7.56; Found: C=66.93, H=10.16, N=7.28.

Compound 394, $C_{32}H_{59}N_3O_3$—3HCl—0.5$H_2O$: $^1H$ NMR (200 MHz, $CD_3OD$) δ: 3.83 (br s, 1H), 3.64 (s, 3H), 3.48 (br s, 1H), 3.3–2.9 (m, 8H), 2.4–1.1 (m, 32H), 0.94 (d, J=6 Hz, 3H), 0.87 (s, 3H), 0.70 (s, 3H); MS(+FAB): 535 (M+1); Anal. calcd.: C=58.93, H=9.74, N=6.44; Found: C=58.71, H=10.13, N=6.39.

EXAMPLE K

Preparation of compounds 395, 396 and 397:

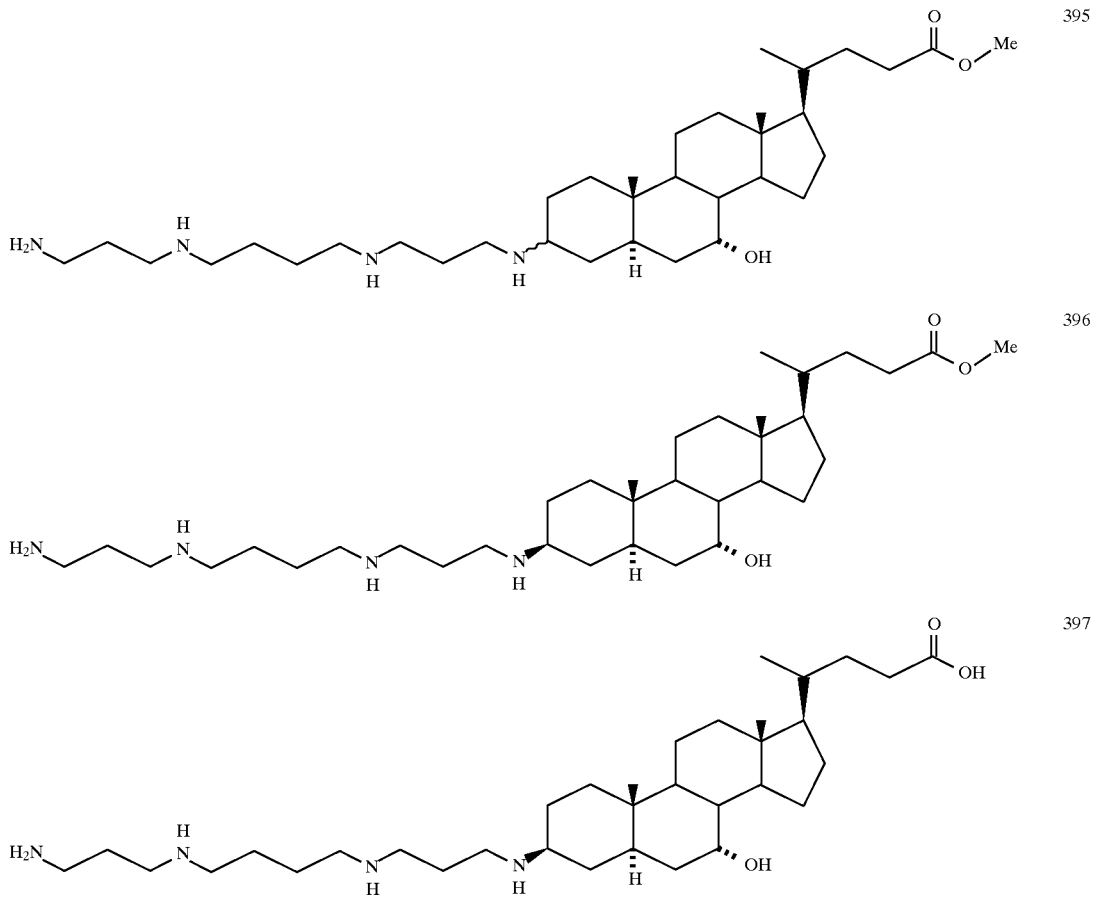

Methyl 7α-hydroxy-3-oxo-5α-cholanoate was coupled to spermine (2 equivalents) with sodium cyanoborohydride, and the ester was hydrolyzed as in the preparation of compound 319, except that lithium hydroxide was used as the base. Purification of compounds 395 and 396 was achieved on silica gel (15:5:1 to 5:5:1 chloroform:methanol:isopropylamine). Purification of compound 397 was achieved on silica gel (2:6:1 benzene:methanol:isopropylamine), followed by treatment with 2M ammonia in methanol (3×20 ml) to drive off isopropylamine. The hydrochloride salts of compounds 395 and 396 were prepared in the same manner as for compound 303.

Compound 395, $C_{35}H_{66}N_4O_3$—4HCl—2H$_2$O: $^1$H NMR (200 MHz, CD$_3$OD) δ: 3.80 (br s, 1H), 3.64 (s, 3H), 3.3–3.0 (m, 13H), 2.4–1.0 (m, 34H), 0.94 (d, J=6 Hz, 3H), 0.87 (s, 3H), 0.70 (s, 3H); Anal. calcd.: C=54.40, H=9.65, N=7.25; Found: C=54.16, H=9.31, N=7.12.

Compound 396, $C_{35}H_{66}N_4O_3$—4HCl—0.5H$_2$O: MS(+FAB): 592 (M+1) Anal. calcd.: C=56.37, H=9.60, N=7.51; Found: C=56.43, H=9.83, N=7.27.

Compound 397, $C_{34}H_{64}N_4O_3$: $^1$H NMR (200 MHz, CD$_3$OD) δ: 3.78 (br s, 1H), 2.9–2.5 (m, 13H), 2.2–1.1 (m, 34H), 0.95 (d, J=6 Hz, 3H), 0.87 (s, 3H), 0.70 (s, 3H); MS(+FAB): 577.3 (M+1).

EXAMPLE L

Preparation of compound 393:

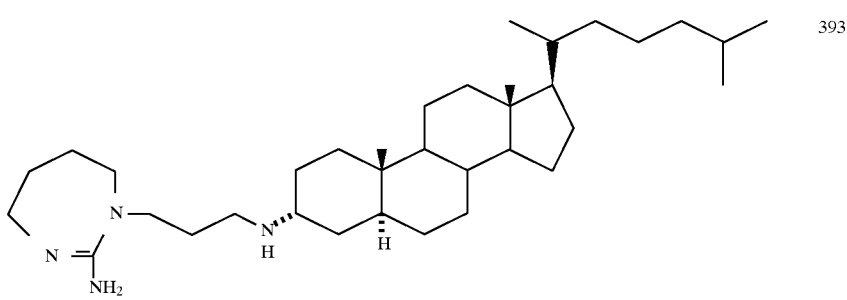

Compound 304 (210 mg, 0.41 mmol) was dissolved in methanol (10 ml) under nitrogen, and treated with o-methylisourea hydrochloride (50 mg, 0.45 mmol) and 1N sodium hydroxide solution (0.45 ml, 0.45 mmol). After 23 hours, additional o-methylisourea was added (102 mg, 0.92 mmol), and the reaction was continued for 7 hours, quenched with 1N hydrochloric acid solution (pH<7), and evaporated. The residue Was partitioned between 1N sodium hydroxide solution (50 ml) and chloroform (100 ml). After washing with additional chloroform (50 ml), the combined organic layers were dried ($Na_2SO_4$) and concentrated. Purification by flash chromatography on silica gel (2-cm diameter, gradient elution with 5 to 15% methanol in methylene chloride) afforded a white solid (32 mg). This material was dissolved in chloroform (3 ml), cooled in an ice bath, treated with 1M hydrogen chloride in ether (1 ml), and concentrated in vacuo to afford compound 393 (37 mg, 14% yield). $C_{35}H_{64}N_4$—2HCl—$2H_2O$: $^1$H NMR (200 MHz, $CD_3OD$) δ: 3.5–3.3 (m, 5H), 3.2–3.0 (m, 4H), 2.2–1.0 (m, 37H), 0.95–0.86 (m, 9H), 0.70 (S, 3H); IR (KBr, $cm^{-1}$): 3306, 3153, 2934, 1654, 1586, 1445, 1383; MS(+FAB): 541.4 (M+1); Anal. calcd.: C=64.69, H=10.86, N=8.62, Found: C=65.06, H=10.98, N=8.83.

EXAMPLE M

Preparation of compounds 370 and 371:

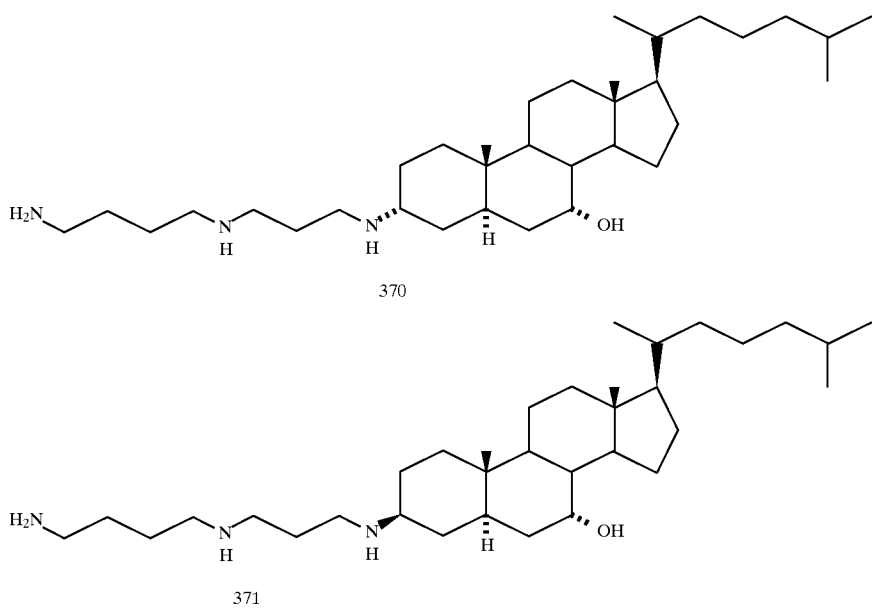

Preparation of compound 1010:

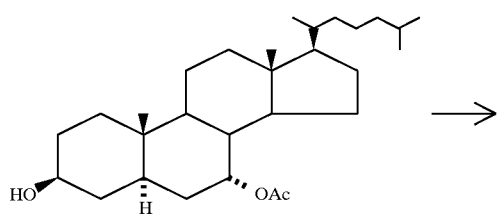

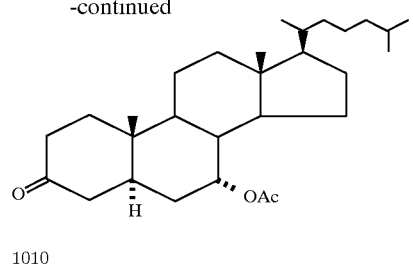

To a suspension of pyridinium chlorochromate (6.85 g, 31.8 mmol) in dichloromethane (130 ml) was added a solution of compound 1006 (5.96 g, 13.3 mmol) in dichloromethane (70 ml). After stirring for 3 hours at room temperature, the reaction mixture was diluted with ether (100 ml), filtered, and washed with ether. The organic layer was washed with 5% sodium hydroxide solution, 5% hydrochloric acid solution, saturated sodium bicarbonate and brine. The dried ethereal layer was evaporated and purified by flash chromatography (6 cm, gradient elution with 0–20% ethyl acetate in hexane) to yield pure compound 1010 (5.25 g, 77% yield). $^1$H NMR (200 MHz, $CDCl_3$) δ: 4.92 (m, 1H), 2.5–1.0 (m, 29H), 2.06 (s, 3H), 1.03 (s, 3H), 0.91 (d, J=6.5 Hz, 3H), 0.87 (d, J=6.5 Hz, 6H), 0.67 (s, 3H); IR (KBr, $cm^{-1}$): 2949, 1736, 1468, 1372, 1244, 1023; MS(ES+): 467.8 (M+Na).

Preparation of compounds 370 and 371: The steroid 1010 was coupled to polyamine 301 with sodium cyanoborohydride, the BOC groups were removed with trifluoroacetic acid, and the acetate was hydrolyzed as in the preparation of compound 319, except that sodium hydroxide was used as the base. Purification was achieved on silica gel (2:6:1 benzene:methanol:isopropylamine). Compound 370 ($^1$H NMR (200 MHz, $CD_3OD$) δ: 3.80 (m, 1H), 2.97 (m, 1H), 2.9–2.6 (m, 8H), 2.1–1.0 (m, 35H), 0.94 (d, J=6.5 Hz, 3H), 0.88 (d, J=6.5 Hz, 6H), 0.87 (s, 3H), 0.70 (s, 3H)) and compound 371 ($^1$H NMR (200 MHz, $CD_3OD$) δ: 3.77 (m, 1H), 2.8–2.5 (m, 9H), 2.1–1.0 (m, 35H), 0.93 (d, J=6.5 Hz, 3H), 0.88 (d, J=6.5 Hz, 6H), 0.83 (s, 3H), 0.69 (s, 3H)) were converted to their hydrochloride salts as in the preparation of compound 303. Compound 370: IR (KBr, cm$^{-1}$) : 3415, 2948, 1595, 1467, 1382, 1031; MS(+FAB): 532.4 (M+1); Anal. calcd. for $C_{34}H_{65}N_3O$—3HCl—2H$_2$O: C=60.29, H=10.71, N=6.20; Found: C=60.01, H=11.09, N=6.3. Compound 371: IR (KBr, cm$^{-1}$): 3414, 2953, 1596, 1468, 1381, 1033; MS(+FAB): 532.4 (M+1); Anal. calcd. for $C_{34}H_{65}N_3O$.3HCl.2H$_2$O: C=60.29, H=10.71, N=6.20; Found: C=60.49, H=11.00, N=6.47.

EXAMPLE N

Preparation of compound 470:

Preparation of precursors:

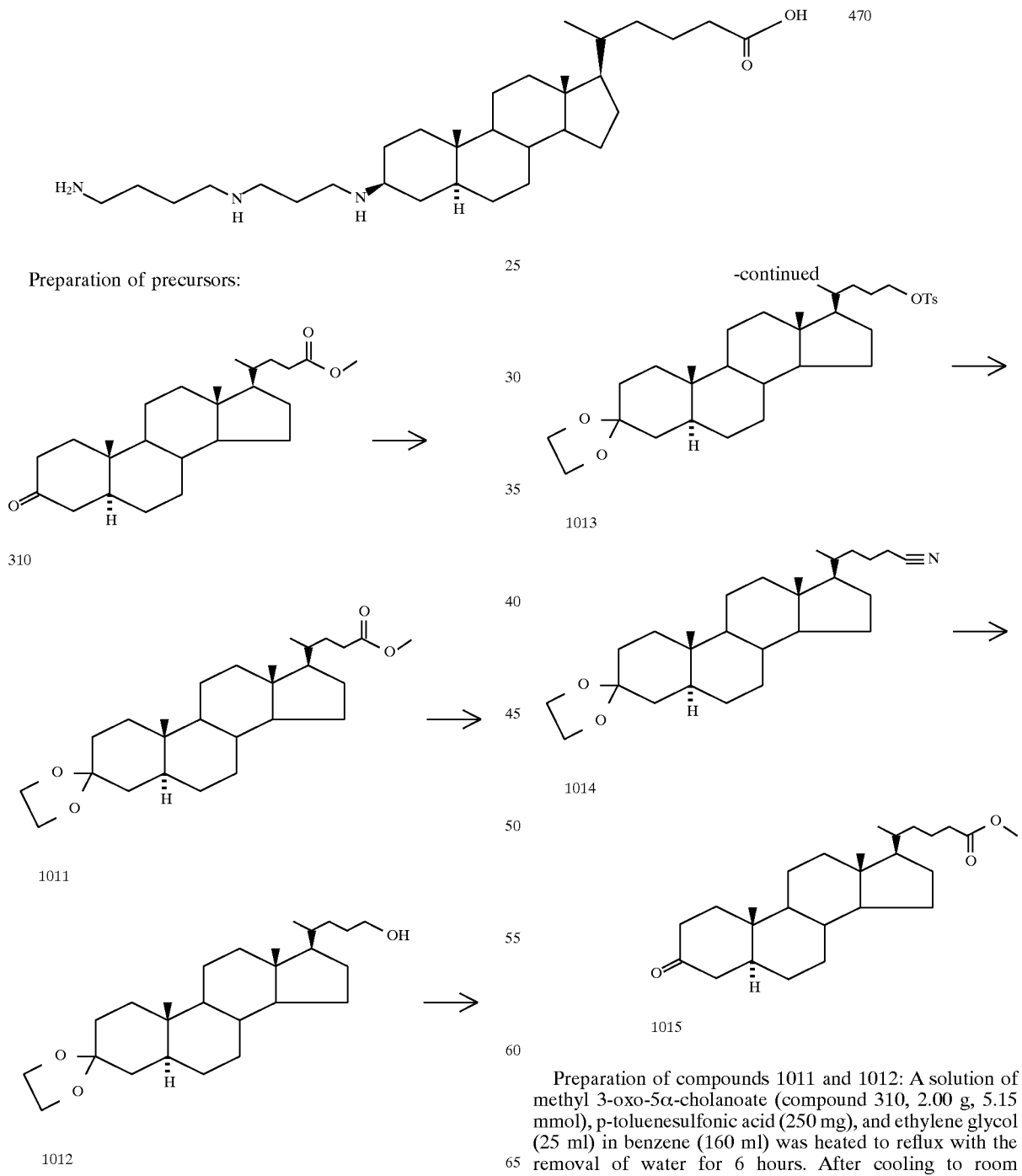

Preparation of compounds 1011 and 1012: A solution of methyl 3-oxo-5α-cholanoate (compound 310, 2.00 g, 5.15 mmol), p-toluenesulfonic acid (250 mg), and ethylene glycol (25 ml) in benzene (160 ml) was heated to reflux with the removal of water for 6 hours. After cooling to room temperature, saturated sodium bicarbonate (30 ml) was added, and the aqueous phase was extracted with benzene and ethyl acetate. The organic layers were washed with water and brine, dried over sodium sulfate, and evaporated to yield compound 1011, which was used for the next step without purification.

A solution of 1M lithium aluminum hydride (25 ml, 25 mmol) in ether under nitrogen was treated with a solution of compound 1011 in anhydrous ether (80 ml) and heated to reflux for 5 hours. After stirring overnight, the reaction mixture was quenched at 0° C. with water and 2N sodium hydroxide solution. The aqueous layer was extracted with ether, followed by washing with brine, drying over magnesium sulfate, and evaporating to afford compound 1012 (1.80 g, 86% yield). $^1$H NMR (400 MHz, CDCl$_3$) δ: 3.94 (s, 4H), 3.62 (m, 2H), 2.0–1.0 (m, 28H), 0.92 (d, J=6 Hz, 3H), 0.81 (s, 3H), 0.66 (s, 3H).

Preparation of compounds 1013 and 1014: A solution of compound 1012 (3.63 g, 8.97 mmol) in anhydrous pyridine (16 ml) was treated with p-toluenesulfonyl chloride (2.3 g, 12.1 mmol) at room temperature, and left overnight. Ice water was added, and the reaction mixture was left for 30 minutes with stirring. Then 6 N hydrochloric acid was added (70 ml), and the aqueous layer was extracted with dichloromethane and ether. The organic layers were washed with 2N hydrogen chloride, saturated sodium bicarbonate and brine, dried, and evacuated to yield crude compound 1013. Compound 1013 was dissolved in dimethylsulfoxide (40 ml) and treated with sodium cyanide (1.4 g, 28 mmol) at 90° C. for 2.5 hours under nitrogen. After cooling, the reaction mixture was treated with ice water and extracted into ether and dichloromethane. The organic layers were washed with brine, dried over sodium sulfate, and purified by chromatography (4-cm diameter, gradient elution with 0–25% ethyl acetate in hexane) to yield pure compound 1014. $^1$H NMR (400 MHz, CDCl$_3$) δ: 3.94 (s, 4H), 2.32 (m, 2H), 2.0–1.0 (m, 28H), 0.93 (d, J=6 Hz, 3H), 0.81 (s, 3H), 0.66 (s, 3H); IR (KBr, cm$^{-1}$): 2930, 2247, 1445, 1381, 1357, 1133, 1091, 928, 899; MS(+FAB): 414.4 (M+1).

Preparation of compound 1015: A solution of compound 1014 (480 mg, 1.16 mmol) in acetic acid (35 ml) and concentrated hydrochloric acid (25 ml) was refluxed for 25 hours. After evaporating the solvent, the residue was partitioned between water and ethyl acetate. After drying and evaporating, the crude carboxylic acid was dissolved in methanol (25 ml), treated with concentrated hydrochloric acid (1. ml), and brought to reflux for 20 minutes. After evaporation of solvent, the product was dissolved in ethyl acetate and water and extracted again with ethyl acetate. The organic layers were washed with brine, dried over sodium sulfate, and purified by flash chromatography (2-cm diameter, gradient elution with 0–25% ethyl acetate in hexane) to afford pure compound 1015 (298 mg, 64% yield), m.p. 147°–148° C. $^1$H NMR (400 MHz, CDCl$_3$) δ: 3.67 (s, 3H), 2.4–1.0 (m, 30H), 1.01 (s, 3H), 0.93 (d, J=6 Hz, 3H), 0.68 (s, 3H); $^{13}$C NMR (400 MHz, CDCl$_3$) δ: 212.3, 174.5, 56.5, 56.1, 54.0, 51.6, 46.9, 44.9, 42.8, 40.1, 38.8, 38.4, 35.8, 35.7, 35.6, 34.7, 31.9, 29.2, 28.4, 24.4, 21.7, 21.6, 18.8, 12.2, 11.7; MS(+FAB): 403.3 (M+1); Anal. calcd. for C$_{26}$H$_{42}$O$_3$: C=77.56, H=10.51; Found: C=77.49, H=10.52.

Preparation of compound 470: Steroid 1015 was coupled to polyamine 301 with sodium cyanoborohydride, the BOC groups were removed with trifluoroacetic acid, and the ester was hydrolyzed as in the preparation of compound 319, except that lithium hydroxide was used as the base. Purification was achieved on silica gel (gradient elution with 14:4:1 to 4:4:1 chloroform:methanol:isopropylamine). After evaporation from methanol:chloroform (3x), the compound was treated with 2M ammonia in methanol and evaporated (3×20 ml) to drive off isopropylamine. $^1$H NMR (400 MHz, CD$_3$OD) δ: 2.8–2.6 (m, 9H) , 2.2–1.0 (m, 36H) , 0.92 (d, J=6 Hz, 3H) , 0.80 (s, 3H) , 0.66 (s, 3H); MS(+FAB): 518.4 (M+1); Anal. calcd.: C=71.73, H=11.47, N=7.84; Found: C=7.03, H=11.06, N=7.53.

EXAMPLE O

Preparation of compounds 431, 432, 433, 465, 466, 467, and 469.

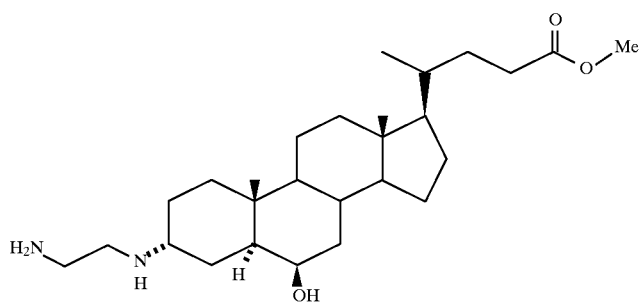

431

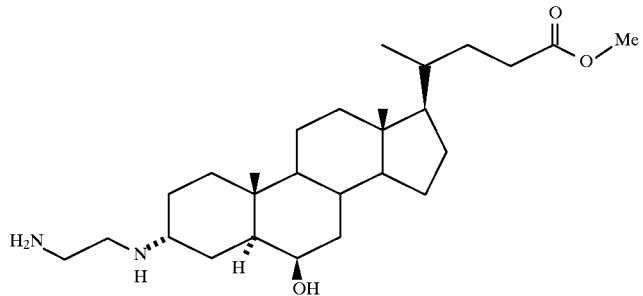

432

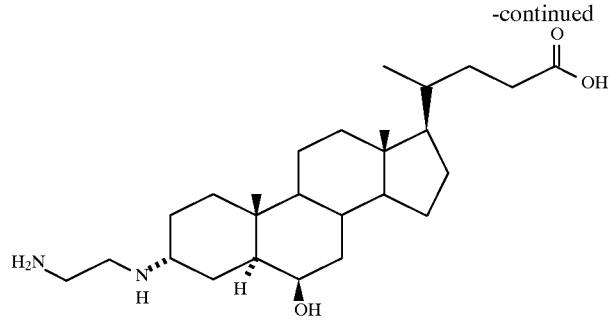
433
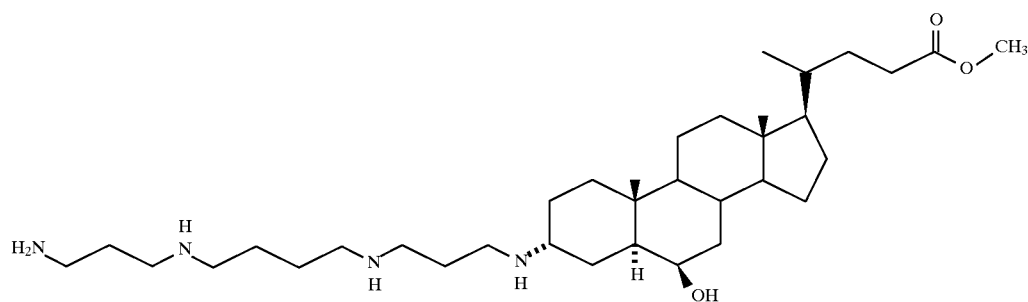
465
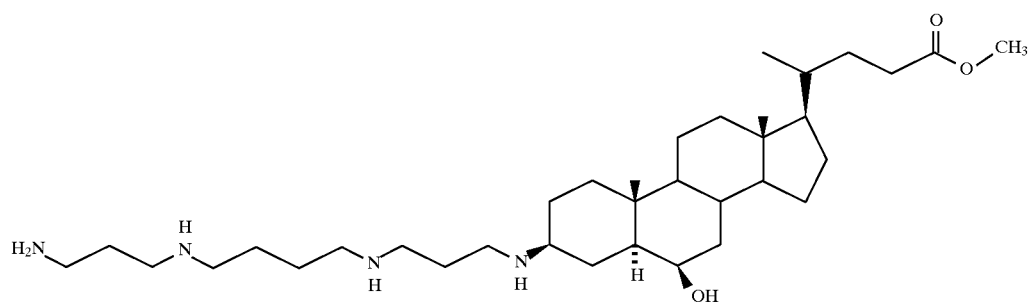
466
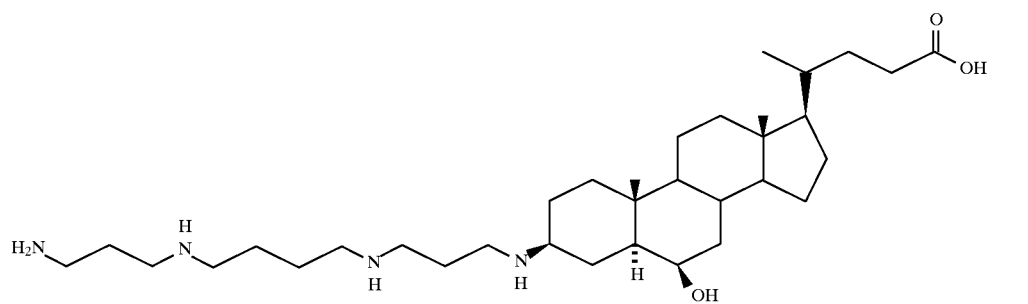
467
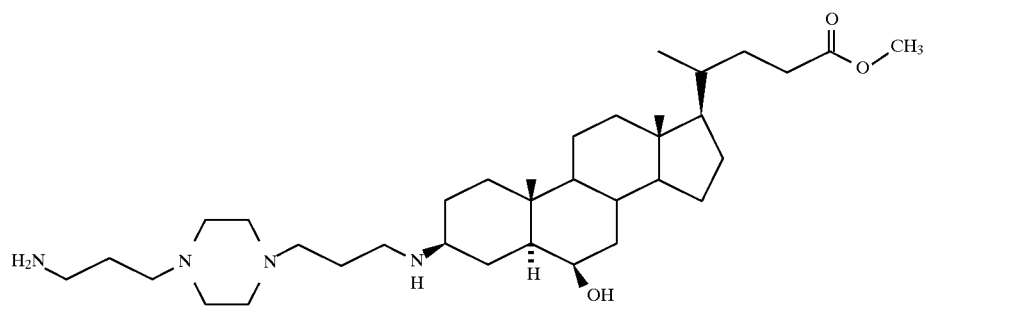
469

Preparation of precursors:

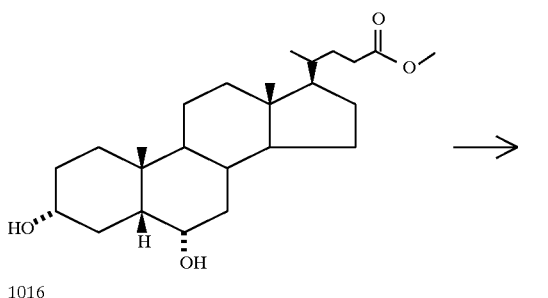

1016

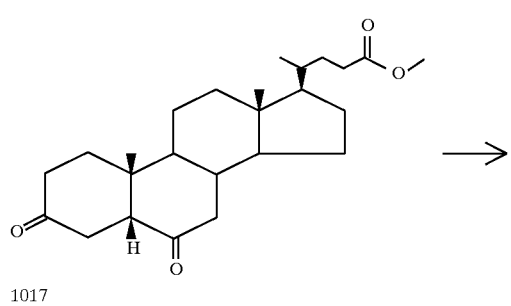

1017

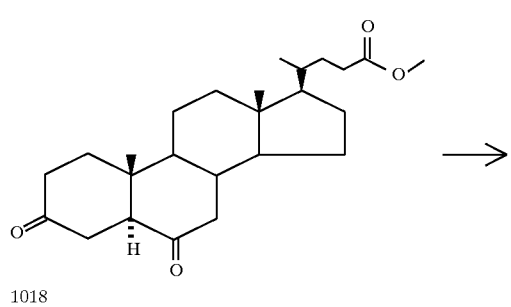

1018

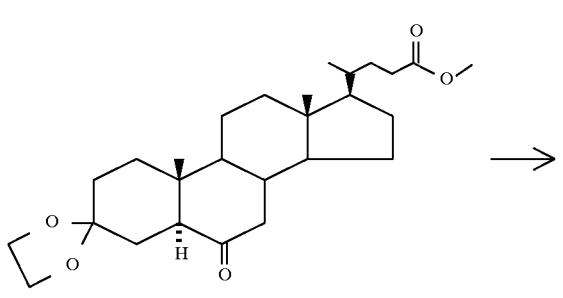

1019

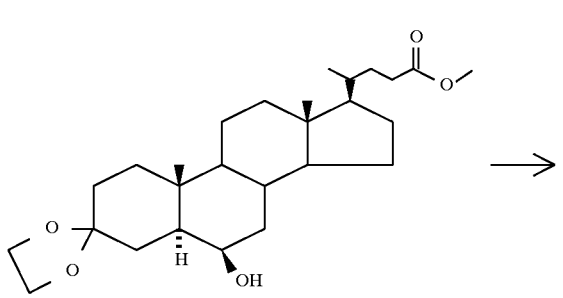

1020

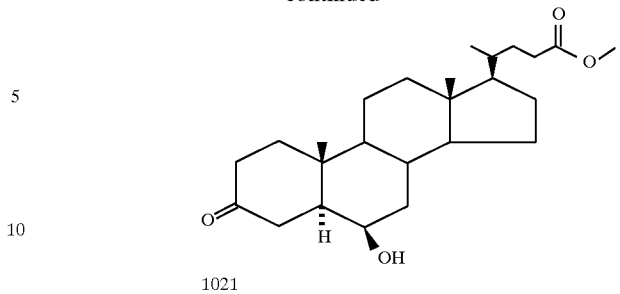

1021

Preparation of compound 1016: The methyl ester of hyodeoxycholic acid was prepared by acid-catalyzed esterification of hyodeoxycholic acid in methanol. To a magnetically stirred 500-ml round-bottom flask containing absolute methanol (200 ml) was added hyodeoxycholic acid (10 g, 25.5 mmol) and concentrated sulfuric acid (5 ml) dropwise. The reaction was stirred overnight and then treated with dichloromethane (250 ml), followed by washing with sodium bicarbonate solution (2×100 ml) and brine (100 ml). The organic layer was then dried over anhydrous sodium sulfate, filtered, and dried under vacuum to yield compound 1016 (10.1 g, 97% yield) (see *Organic Preparations and Procedures Int.* 19(2–3), 1987, 197–208).

Preparation of compound 1017: The 3,6-dioxo sterol was prepared by oxidation of methyl hyodeoxycholic acid with pyridinium chlorochromate. Compound 1016 (10.1 g, 25 mmol) was dissolved in dichloromethane (200 ml). To a magnetically stirred flask in an ice water bath was added pyridinium chlorochromate (33 g, 150 mmol). The reaction was allowed to warm to room temperature and to proceed for 8 hours, until the product was the only visible TLC spot. A major portion of the dichloromethane was removed under vacuum, and ethyl acetate (250 ml) was then added to the flask. The chromium crust in the bottom of the flask was broken up with a spatula, and the contents of the flask were filtered through a Celite column. The elutant from the column was then reduced in volume under vacuum and filtered through a florisil column (elution with ethyl acetate). The elutant was again reduced in volume to approximately 200 ml, and diethyl ether (100 ml) was added, followed by washing with sodium bicarbonate solution (2×250 ml) and then brine (250 ml). The organic layer was dried over anhydrous sodium sulfate, filtered, and dried under vacuum. The total yield of methyl 3,6-dioxo-5β-cholan-24-oate 1017 without recrystallization was 9.6 g (24 mmol, 96%) (see *Organic Preparations and Procedures Int.* 19(2–3), 1987, 197–208). The product can be recrystallized from a number of solvents (absolute methanol, ethyl acetate in hexanes, or diethyl ether in hexanes) if any chromium remains.

Preparation of compound 1018: The 3,6-dioxo-5α sterol was prepared by acid-catalyzed isomerization of the 5β sterol. To methanol (250 ml) was added the 3,6-dioxo-5β sterol 1017 (9.6 g, 24 mmol) and tetrahydrofuran (25 ml) to dissolve the sterol completely. Concentrated hydrochloric acid (12.5 ml) was added, and the reaction was allowed to proceed overnight. The solvent was then remove under vacuum to yield 9.6 g (100% yield) of methyl 3,6-dioxo-5α-cholan-24-oate 1018 (see *Organic Preparations and Procedures Int.* 19(2–3), 1987, 197–208; authors used base-catalyzed isomerization using sodium methoxide rather than HCl).

Preparation of compound 1019: The mono-protection of methyl 3,6-dioxo-5α-cholan-24-oate 1018 may be accomplished using a variety of techniques. One technique involved refluxing compound 1018 (9.6 g, 23.8 mmol) in toluene (250 ml) with ethylene glycol.(1.77 g, 28.5 mmol) in the presence of catalytic p-toluenesulfonic acid. A Dean Stark trap was used for removing the toluene/water azeotrope. The reaction was judged to be complete by TLC after approximately 20 minutes. The reaction was worked up by pouring the toluene over sodium bicarbonate solution (500 ml) and ice slurry. The organic layer was washed with additional sodium bicarbonate (200 ml) and brine (200 ml), dried over anhydrous sodium sulfate, filtered, and dried under vacuum. The crude product was chromatographed on silica gel (4 cm×25 cm, elution with 33% ethyl acetate in hexanes). Methyl 3-dioxolane-6-oxo-5α-cholan-24-oate 1019 (8.9 g, 81%) was the second band off the column; the only other product present was the less polar di-dioxolane. Subsequent techniques yielded better results by substituting benzene for toluene and following the reaction by TLC, which apparently allows for greater selectivity. The reaction can be stopped before significant di-protection occurs in the lower boiling solvent. Compound 1019: m.p. 124°–126° C.; $^1$H NMR (200 MHz, CDCl$_3$) δ: 4.04–3.93 (m, 4H), 3.68 (s, 3H), 0.95 (d, J=6 Hz, 3H), 0.78 (s, 3H), 0.69 (s, 3H); IR (KBr, cm$^{-1}$): 2945, 1742, 1709, 1439, 1381, 1313, 1162, 1090; MS(FD): 446 (M$^+$), 388.

Preparation of compound 1020: The 6β-hydroxy sterol was prepared in good yield from the mono-protected diketone by reduction with sodium borohydride. The 3-dioxolane-6-oxo sterol 1019 (5 g, 11 mmol) was dissolved in tetrahydrofuran (10 ml) and added to absolute methanol (200 ml) and sodium borohydride (2.5 g, 66 mmol). The sodium borohydride was dissolved and stirred for approximately 20–30 minutes before the addition of the sterol. After stirring overnight, the reaction mixture was treated with chloroform (500 ml), and washed with distilled water (2×200 ml) and then brine (100 ml). The organic layer was then dried over sodium sulfate, filtered, concentrated under vacuum, and purified by flash chromatography on silica gel (4 cm×25 cm, elution with 2:1:1 hexanes:ethyl acetate:methylene chloride) to yield methyl 3-dioxolane-6β-hydroxy-5α-cholan-24-oate 1020 (4.35 g, 87% yield). Alternatively, the crude product can be recrystallized from benzene in hexanes, ethyl acetate in hexanes, or chloroform in hexanes (2x) to yield a product of high purity without need for column chromatography. Compound 1020: m.p. 164° C.; $^1$H NMR (200 MHz, CDCl$_3$) δ: 4.04–3.93 (m, 4H), 3.77 (br s, 1H), 3.66 (s, 3H), 1.03 (s, 3H), 0.92 (d, J=6 Hz, 3H), 0.69 (s, 3H); IR (KBr, cm$^{-1}$): 3533, 2937, 1726, 1438, 1379, 1255, 1191, 1096; X-ray diffraction revealed the expected structure.

Preparation of compound 1021: The 3-dioxolane was deprotected using acidic acetone solution. The 3-dioxolane-6β-hydroxy-sterol 1020 (4.0 g, 8.9 mmol) was dissolved in acetone (200 ml) and treated with concentrated hydrochloric acid solution (10 ml). After approximately 1 hour, the reaction mixture was poured into a sodium bicarbonate solution. The solution was extracted with dichloromethane (3×200 ml), washed with distilled water (100 ml) and then brine (100 ml), dried over anhydrous sodium sulfate, filtered, and evaporated under vacuum to yield methyl 3-oxo-6β-hydroxy-5α-cholan-24-oate 1021 (3.45 g, 100% yield): $^1$H NMR (200 MHz, CDCl$_3$) δ: 3.8 (br m, 1H), 3.69 (s, 3H), 1.24 (s, 3H), 0.95 (d, J=6 Hz, 3H), 0.74 (s, 3H); IR (KBr, cm$^{-1}$): 3447, 2954, 1742, 1707, 1431.

Preparation of compounds 431 and 432: The ethylenediamine compounds were prepared as follows. A magnetically stirred solution of 50:50 methanol:tetrahydrofuran (100 ml) and ethylenediamine (2 ml) was treated with acetic acid to lower the pH to approximately 6. The 3-oxo sterol 1021 (1.5 g, 3.7 mmol) was added, and the mixture was stirred for 15 minutes. Sodium cyanoborohydride (1 g, 16 mmol) was dissolved in 10 ml methanol and added to the reaction vessel, and the pH was again adjusted to 6 by the addition of acetic acid. The reaction was stirred for 1 hour, and the contents of the flask were poured into a pH 10.5 carbonate-buffer ice slurry (250 ml). The solution was extracted with chloroform (5×150 ml). The organic layers were combined, dried over anhydrous sodium sulfate, filtered, dried under vacuum, and purified by flash chromatography on silica gel (4 cm×25 cm, elution with 8:2:1 chloroform:methanol:isopropylamine) to afford the less polar α-isomer 431 (260 mg, 15% yield) and the more polar β-isomer 432 (840 mg, 49% yield). Compound 431: $^1$H NMR (400 MHz, CD$_3$OD) δ: 3.74 (m, 1H), 3.65 (s, 3H), 3.53 (m, 1H), 1.06 (s, 3H), 0.94 (d, J=6 Hz, 3H), 0.74 (s, 3H); IR (KBr, cm$^{-1}$): 3426, 2943, 1740, 1590, 1438, 1379, 1258, 1168, 1027; MS(+FAB): 449.5 (M+1); Anal. calcd. for C$_{27}$H$_{48}$N$_2$O$_3$—2HCl—0.7H$_2$O: C=60.70, H=9.70, N=5.24; Found: C=60.97, H=9.68, N=5.34. Compound 432: $^1$H NMR (400 MHz, CD$_3$OD) δ: 3.75 (m, 1H), 3.64 (s, 3H), 1.02 (s, 3H), 0.94 (d, J=6 Hz, 3H), 0.73 (s, 3H); IR (KBr, cm$^{-1}$): 3560, 3366, 3257, 2936, 1726, 1648, 1605, 1438, 1376, 1166, 1047; MS(+FAB): 449.5 (M+1); Anal. calcd. for C$_{27}$H$_{48}$N$_2$O$_3$—0.4H$_2$O: C=71.13, H=10.79, N=6.14; Found: C=71.15, H=10.71, N=6.28.

Preparation of compounds 465 and 466: To a magnetically stirred flask containing anhydrous methanol (100 ml) was added compound 1021 (1.5 g, 3.7 mmol), spermine (2 g, 9.9 mmol), powdered 3 Å sieves (2 g), and acetic acid until the pH was 6. The flask was sealed, the contents stirred overnight, and then sodium cyanoborohydride (1 g, :16 mmol) in methanol (10 ml) was added. The pH was again adjusted with acetic acid, and the reaction mixture was stirred for 8 hours. The workup was similar to the workup for the ethylenediamine compounds. The crude product was purified by flash chromatography (5 cm×25 cm, elution with 4:5:1 chloroform:methanol:isopropylamine), affording less polar α-amino isomer 465 and more polar β-amino isomer 466. The total yield of amino sterol was 1.3 g (58% yield). Compound 465: $^1$H NMR (400 MHz, CD$_3$OD) δ: 3.75 (m, 1H), 3.65 (s, 3H), 3.54 (m, 1H), 1.06 (s, 3H), 0.95 (d, J=6 Hz, 3H), 0.74 (s, 3H); IR (KBr, cm$^{-1}$): 3406, 2944, 1740, 1596, 1466, 1168, 1049, 1027; MS(+FAB): 591.4 (M+1); Anal. calcd. for C$_{35}$H$_{66}$N$_4$O$_3$—4HCl—1.2H$_2$O: C=55.43, H=9.62, N=7.39; Found: C=55.70, H=9.15, N=7.12. Compound 466: $^1$H NMR (400 MHz, CD$_3$OD) δ: 3.79 (m, 1H), 3.65 (s, 3H), 1.06 (s, 3H), 0.95 (d, J=6 Hz, 3H), 0.74 (s, 3H); IR (KBr, cm$^{-1}$) : 3406, 2944, 1740, 1595, 1459, 1381, 1167, 1051, 1026; MS(+FAB): 591.4 (M+1); Anal. calcd. for C$_{35}$H$_{66}$N$_4$O$_3$—4HCl—1.2H$_2$O: C=55.43, H=9.62, N=7.39; Found: C=55.48, H=9.03, N=7.33.

Preparation of compound 469: This compound was prepared in a manner analogous to that used for compound 466, but using polyamine 1023:

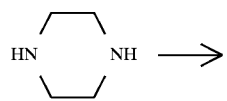

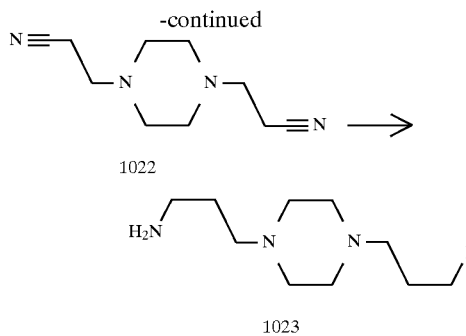

The polyamine was prepared from piperazine by double addition of acrylonitrile to yield compound 1022, which was reduced by Raney nickel catalyzed hydrogenation. β-amino isomer 469: $^1$H NMR (400 MHz, CD$_3$OD) δ: 3.78 (m, 1H), 3.64 (s, 3H), 3.5–3.3 (m, 8H), 3.2–3.0 (m, 9H), 2.4–1.0 (m, 30H), 1.03 (s, 3H), 0.92 (d, J=6.5 Hz, 3H), 0.71 (s, 3H); IR (KBr, cm$^{-1}$) : 3406, 2943, 1736, 1594, 1443, 1165; MS(+FAB): 589.4 (M+1); Anal. calcd. for C$_{35}$H$_{64}$N$_4$O$_3$—4HCl—3H$_2$O: C=53.29, H=9.46, N=7.10; Found: C=53.06, H=8.90, N=8.43.

Preparation of compounds 433 and 467: An amount of aminosterol methyl ester (1 mmol) as the free base was weighed into a 25-ml round-bottom flask. The aminosterol was dissolved in a minimal amount of tetrahydrofuran (2 ml), treated with 1N potassium hydroxide solution (10 ml), and magnetically stirred for 1 hour. The solution was then neutralized with 1N HCl, and the solvent was removed under vacuum. The residue was redissolved in a minimal amount of deionized water and applied to an octadecyl-functionalized silica gel column (Aldrich, 2×10 cm, gradient elution of acetonitrile in 2% trifluoroacetic acid in water). The fractions containing aminosterol were pooled, and the solvent was removed under vacuum. The aminosterol was redissolved in 0.1N HCl, and the solvent was removed under vacuum (2x) to insure the removal of trifluoroacetate. Benzene was added to the resulting hydrochloride salts, followed by evaporation overnight to remove as much water as possible.

Ethylenediamine β-amino isomer 433 was not treated with HCl, but isolated as the trifluoroacetate salt. Compound 433: $^1$H NMR (400 MHz, CD$_3$OD) δ: 3.78 (m, 1H), 1.06 (s, 3H), 0.95 (d,. J=6.5 Hz, 3H), 0.74 (s, 3H); IR (KBr, cm$^{-1}$): 3533, 3488, 2941, 1716, 1679, 1615, 1489, 1431, 1191; MS(+FAB): 435.5 (M+1), 531.5 (likely a trace of the trifluoroacetamide); Anal. calcd. for C$_{26}$H$_{46}$N$_2$O$_3$—2TFA—0.7H$_2$O: C=53.36, H=7.37, N=4.15; Found: C=54.36, H=7.45, N=4.40.

Spermine β-amino isomer 467: $^1$H NMR (400 MHz, CD$_3$OD) δ: 3.80 (m, 1H), 1.05 (s, 3H), 0.95 (d, J=6.5 Hz, 3H), 0.73 (s, 3H); IR (KBr, cm$^{-1}$): 3406, 2944, 1718, 1637, 1458; MS(+FAB): 577.4 (M+1); Anal. calcd. for C$_{34}$H$_{64}$N$_4$O$_3$—4HCl—4H$_2$O: C=51.38, H=9.64, N=7.05; Found: C=51.40, H=8.77, N=7.01.

EXAMPLE P

Preparation of bile acid methyl esters 409, 410, 411, 355, 356, 416, 448, 414, 415, 412, 413, 417 and 449:

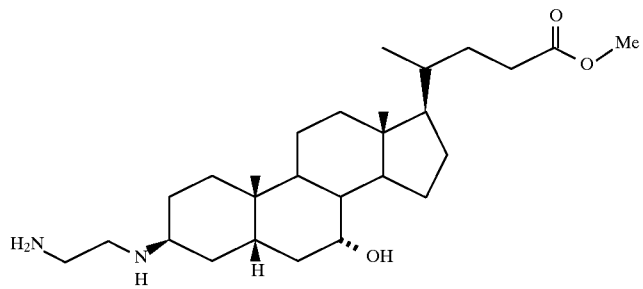

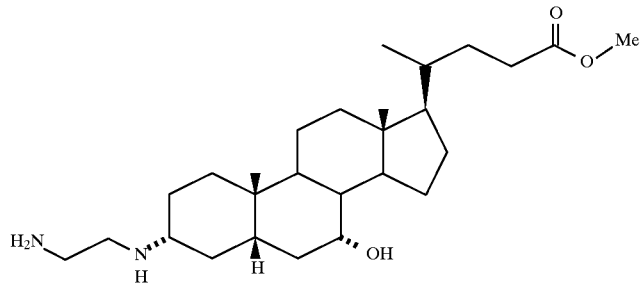

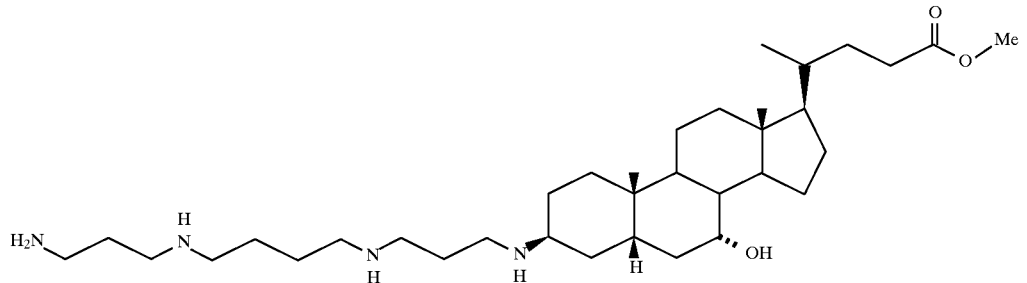

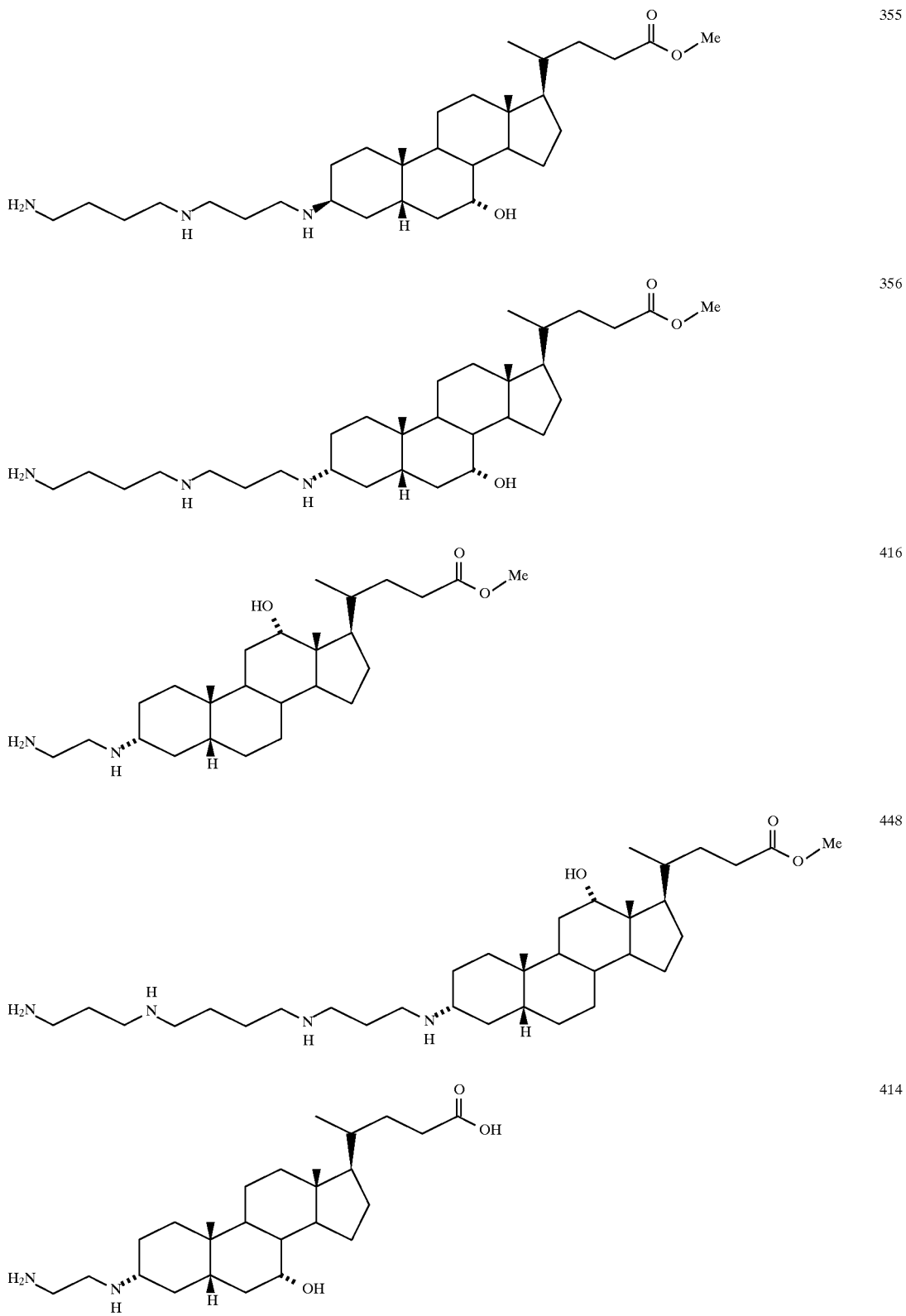

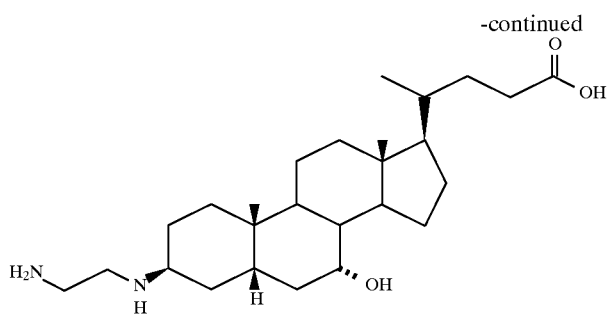
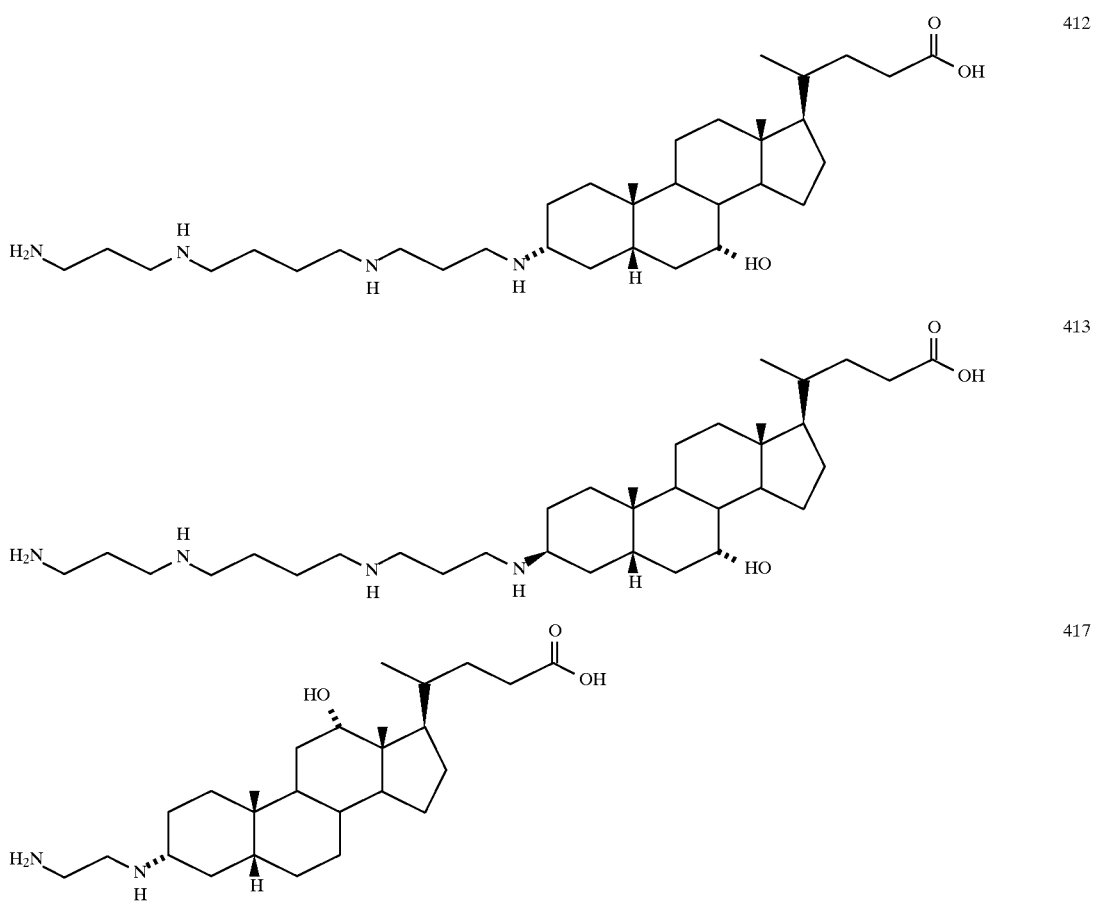
Preparation of precursors: The methyl esters of chenodeoxycholic acid and deoxycholic acid, which are structurally depicted below, were prepared by the same procedure as used to esterify hyodeoxycholic acid to compound 1016.

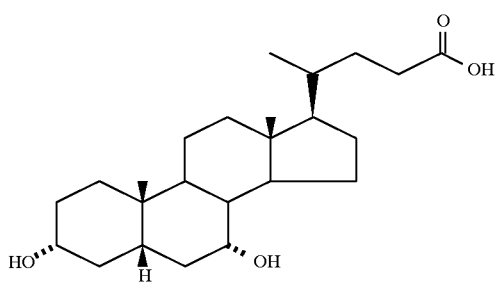

Chenodeoxycholic Acid

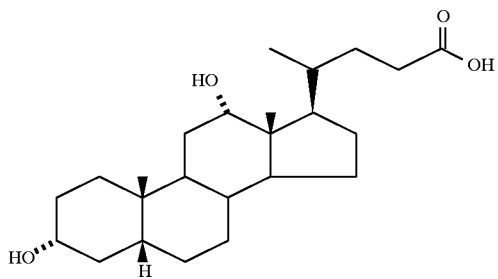

Deoxycholic Acid

Silver carbonate oxidations of bile acid esters to prepare 3-keto steroids: Both chenodeoxycholic and deoxycholic acid derivatives were prepared by reductive aminations of the 3-oxo sterols with the appropriate amines. The 3-oxo sterols were prepared by similar procedures. Silver carbonate on Celite was prepared by dissolving 4 equivalents of silver nitrate in deionized water and adding sufficient Celite to result in 50% silver carbonate on Celite. To the magnetically stirred solution was added 2.2 equivalents of sodium carbonate dissolved in deionized water, with continued vigorous stirring. The resulting silver carbonate precipitated on Celite was filtered through a glass-fritted funnel, washed with tetrahydrofuran, and allowed to dry in a vacuum desiccator. The methyl ester of the bile acid to be oxidized was dissolved in toluene, treated with 2 equivalents of silver carbonate on Celite, and heated to reflux using a Dean Stark apparatus for azeotropic removal of water. The oxidation was complete in less than 6 hours for both sterols. The only product in both cases was the desired 3-oxo sterol. The solution was filtered and the solvent removed under vacuum. The product in both cases recrystallized readily from ethyl acetate in hexanes to give the 3-oxo sterol in excellent yield (>89% in both cases).

Preparation of compounds 409 and 410: The 3-oxo sterol methyl ester of chenodeoxycholic acid (1.5 g, 3.7 mmol) was dissolved in methanol, to which a ten-fold excess of ethylenediamine (2.5 ml) was added. The pH was lowered with acetic acid to approximately 6, $NaBH_3CN$ (1 g, 15.9 mmol) dissolved in methanol was added, and the pH was again adjusted with acetic acid. The solution was stirred for 1 hour, and then worked up and purified in the same manner as compound 431. The total yield of aminosterol was 58%, with an approximate ratio of α-amino isomer to the less polar β-amino isomer of 7:3. β-Amino isomer 409: $^1$H NMR (400 MHz, $CD_3OD$) δ: 3.81 (m, 1H), 3.68 (s, 3H), 3.42 (m, 1H), 1.04 (s, 3H), 0.95 (d, J=6.5 Hz, 3H), 0.72 (s, 3H); IR (KBr, cm$^{-1}$): 3428, 2940, 2055, 1740, 15.91, 1440, 1377, 1169, 1077, 984; MS(+FAB): 449.3 (M+1); Anal. calcd. for $C_{27}H_{48}N_2O_3$—2HCl—1.2$H_2O$: C=59.70, H=9.72, N=5.16; Found: C=59.59, H=9.49, N=5.15. α-Amino isomer 410: $^1$H NMR (400 MHz, $CD_3OD$) δ: 3.82 (m, 1H), 3.65 (s, 3H), 3.05 (br m, 1H), 1.00 (s, 3H), 0.94 (d, J=6.5 Hz, 3H), 0.72 (s, 3H); IR (KBr, cm$^{-1}$): 3522, 2944, 2017, 1718, 1619, 1448, 1377, 1314, 1282, 1260, 1163, 1018; MS(+FAB): 449.3 (M+1); Anal. calcd. for $C_{27}H_{48}N_2O_3$—2HCl—3.7$H_2O$: C=55.13, H=9.84, N=4.76; Found: C=55.03, H=9.32, N=4.78.

Preparation of compound 411: This spermine compound was prepared by the same procedure as the ethylenediamine compounds, except for the following modification. One gram of the 3-oxo sterol methyl ester of chenodeoxycholic acid and 1 g of spermine (approx. 2 equiv.) were used, and the chromatography required a more polar solvent system (i.e., 5:4:1 $CHCl_3$:methanol:isopropylamine). The total yield of aminosterol was 48%. The ratio of α-amino isomer to β-amino isomer 411 was not determined due to incomplete separation. Compound 411: $^1$H NMR (400 MHz, $CD_3OD$) δ: 3.83 (m, 1H), 3.65 (s, 3H), 3.42 (m, 1H), 1.04 (s, 3H), 0.95 (d, J=6.5 Hz, 3H), 0.70 (s, 3H); IR (KBr, cm$^{-1}$): 3404, 2946, 2059, 1739, 1595, 1458, 1378, 1168, 1073, 1012, 985, 759; MS(+FAB): 591.4 (M+1); Anal. calcd. for $C_{36}H_{66}N_4O_3$—4HCl—4$H_2O$: C=51.97, H=9.72, N=6.93; Found: C=51.65, H=8.53, N=6.77.

Preparation of compounds 355 and 356: The 3-oxo sterol methyl ester of chenodeoxycholic acid was coupled to polyamine 301 with sodium cyanoborohydride, the BOC groups were removed with trifluoroacetic acid, and the ester was hydrolyzed as in the preparation of compound 319. Purification was achieved on silica gel (15:4:1 to 10:4:1 chloroform:methanol:isopropylamine). Less polar β-amino isomer 355, $C_{32}H_{59}N_3O_3$. $^1$H NMR (400 MHz, $CDCl_3$) δ: 3.87 (m, 1H), 3.68 (s, 3H), 3.15 (m, 1H), 3.0–2.7 (m, 8H), 2.4–1.0 (m, 32H), 0.99 (s, 3H), 0.91 (d, J=6 Hz, 3H), 0.66 (s, 3H); MS(DCI): 534 (M+1). More polar α-amino isomer 356, $C_{32}H_{59}N_3O_3$—3HCl: $^1$H NMR (400 MHz, $CD_3OD$) δ: 3.82 (m, 1H), 3.25–2.95 (m, 9H), 2.5–1.0 (m, 32H), 0.97 (s, 3H), 0.94 (d, J=6 Hz, 3H), 0.69 (s, 3H); MS(DCI): 534 (M+1).

Preparation of compound 416: The procedures used for the preparation of deoxycholic acid derivatives were the same as those used in the preparation of the chenodeoxycholic acid derivatives. For the ethylenediamine compound, the total yield of aminosterol was 62%, with the ratio of α-amino isomer 416 to β-amino isomer being 4:1. Compound 416: $^1$H NMR (400 MHz, $CD_3OD$) δ: 3.97 (m, 1H), 3.68 (s, 3H), 3.22 (br m, 1H), 1.02 (d, J=6.5 Hz, 3H), 1.01 (s, 3H), 0.73 (s, 3H); IR (KBr, cm$^{-1}$): 3418, 2940, 1739, 1616, 1456, 1379, 1253, 1169, 1036; MS(+FAB): 449.4 (M+1); $C_{27}H_{48}N_2O_3$—2HCl—0.5$H_2O$: C=61.12, H=9.69, N=5.28; Found: C=61.20, H=9.50, N=5.07.

Preparation of compound 448: For the spermine derivatives of deoxycholic acid, the total yield of aminosterol was 46% (difficulty in the workup was likely responsible for the lower yield). The ratio of α-amino isomer 448 to β-amino isomer was not determined due to incomplete separation. Compound 448: $^1$H NMR (400 MHz, $CD_3OD$) δ: 3.98 (m, 1H), 3.67 (s, 3H), 1.01 (d, J=6 Hz, 3H), 1.01 (s, 3H), 0.73 (s, 3H); IR (KBr, cm$^{-1}$): 2944, 1738, 1594, 1451, 1378, 1169, 1038, 758; MS(+FAB): 591.5 (M+1); Anal. calcd. for $C_{35}H_{66}N_4O_3$—4HCl—2.3$H_2O$: C=54.02, H=9.66, N=7.20; Found: C=54.00, H=8.64, N=7.22.

Preparation of compounds 414 and 415: The free acids were prepared from the methyl esters as in the preparation of 6β-hydroxy 433. α-Amino isomer 414: $^1$H NMR (400 MHz, $CD_3OD$) δ: 3.83 (m, 1H), 3.06 (br m, 1H), 1.04 (s, 3H), 0.96 (d, J=6 Hz, 3H), 0.73 (s, 3H); IR (KBr, cm$^{-1}$):

2940, 2053, 1709, 1452, 1378, 1167, 1076, 1007, 975; MS(+FAB): 435.5 (M+1); Anal. calcd. for $C_{26}H_{46}N_2O_3$—2HCl—1.5$H_2O$: C=58.41, H=9.62, N=5.24; Found: C=58.24, H=9.40, N=5.47. β-Amino isomer 415: $^1$H NMR (400 MHz, $CD_3OD$) δ: 3.83 (m, 1H), 3.47 (m, 1H), 1.06 (s, 3H), 0.95 (d, J=6 Hz, 3H), 0.73 (s, 3H); IR (KBr, $cm^{-1}$) 3488, 2935, 2054, 1709, 1593, 1499, 1450, 1246, 1168, 1077, 1022, 984; MS(+FAB): 435.5 (M+1); Anal. calcd. for $C_{26}H_{46}N_2O_3$—2HCl—1.5$H_2O$: C=58.41, H=9.62, N=5.24; Found: C=58.59, H=9.35, N=5.43.

Preparation of compounds 412, 413, 417 and 449: These compounds were produced using procedures analogous to those above.

α-Amino 412: $^1$H NMR (400 MHz, $CD_3OD$) δ: 3.83 (m, 1H), 3.00 (br m, 1H), 1.04 (s, 3H), 0.96 (d, J=6 Hz, 3H), 0.74 (s, 3H); IR (KBr, $cm^{-1}$): 3413, 2942, 2061, 1710, 1594, 1460, 1377, 1167, 1074; MS(+FAB): 577.7 (M+1); Anal. calcd. for $C_{34}H_{64}N_4O_3$—4HCl—2.5$H_2O$: C=53.19, H=9.58, N=7.30; Found: C=53.27, H=9.47, N=7.32.

β-Amino 413: $^1$H NMR (400 MHz, $CD_3OD$) δ: 3.8 (m, 1H), 3.4 (m, 1H), 1.05 (s, 3H), 0.96 (d, J=6 Hz, 3H), 0.73 (s, 3H); MS(+FAB): 577.7 (M+1).

Deoxycholic acid ethylenediamine 417 (α-amino isomer): $^1$H NMR (400 MHz, $CD_3OD$) δ: 4.03 (m, 1H), 3.22 (br m, 1H), 1.03 (d, J=6 Hz, 3H), 1.00 (s, 3H), 0.74 (s, 3H); IR (KBr, $cm^{-1}$): 2940, 1706, 1456, 1379, 1254, 1034; MS(+FAB): 435.4 (M+1); Anal. calcd. for $C_{26}H_{46}N_2O_3$—2HCl—2$H_2O$: C=57.45, H=9.64, N=5.15; Found: C=57.32, H=9.22, N=5.13.

Deoxycholic acid spermine 449 (α-amino isomer): $^1$H NMR (400 MHz, $CD_3OD$) δ: 4.02 (m, 1H), 1.04 (d, J=6 Hz, 3H), 1.00 (s, 3H), 0.75 (s, 3H); IR (KBr, $cm^{-1}$): 2941, 1716, 1448, 1038; MS(+FAB): 577.4 (M+1); Anal. calcd. for $C_{34}H_{64}N_4O_3$—4HCl—1.5$H_2O$: C=54.57, H=9.54, N=7.47; Found: C=54.31, H=8.71, N=7.80.

EXAMPLE Q

Preparation of monoamine compounds 363 and 364:

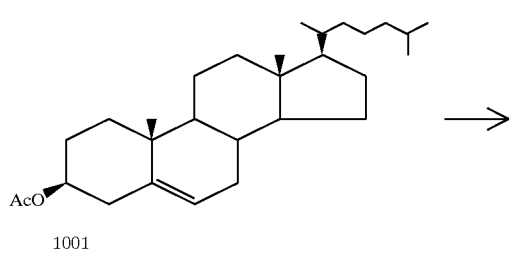

1001

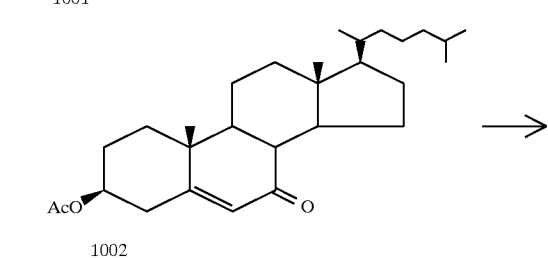

1002

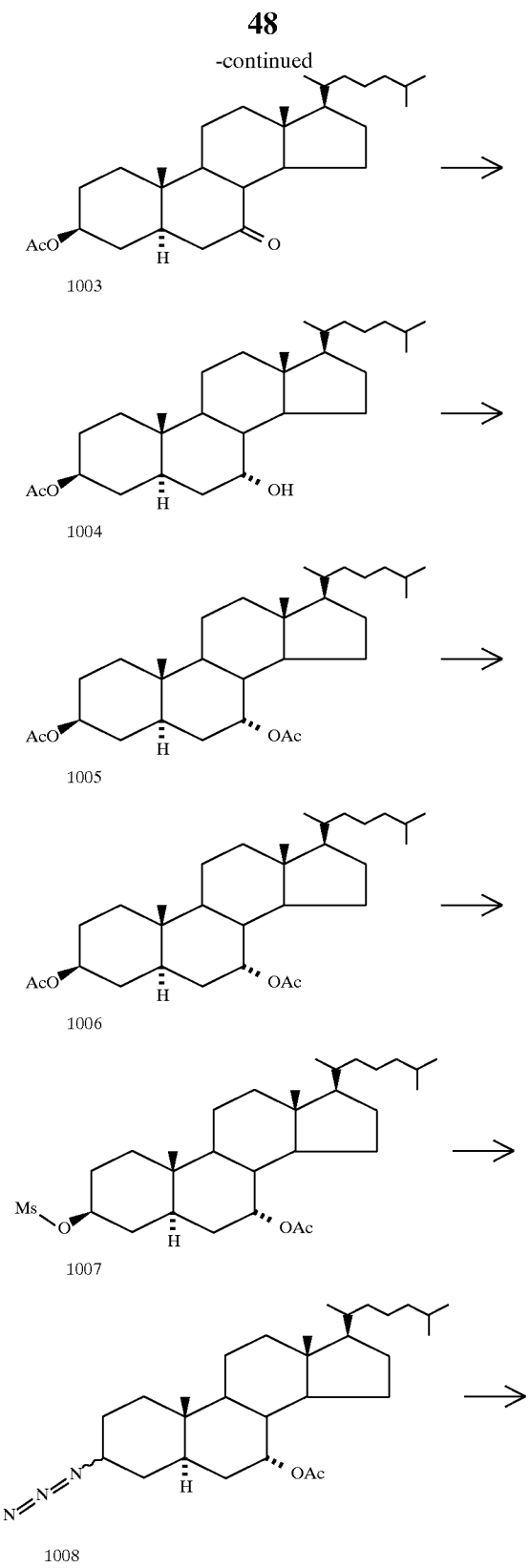

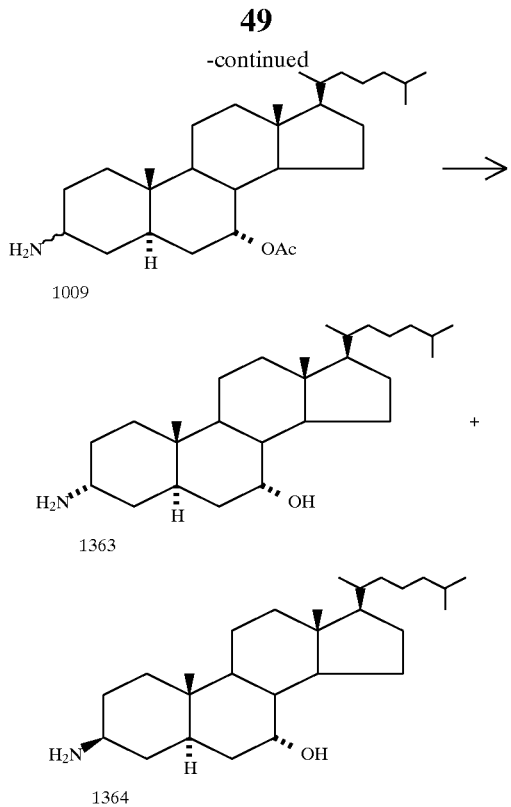

Preparation of compound 1002: To a suspension of chromium trioxide (72.6 g, 660 mmol) in dichloromethane (1000 ml) at −78° C., was added 3,5-dimethylpyrazole (63.4 g, 660 mmol). After 20 minutes, cholesteryl acetate (compound 1001, 24 g, 56 mmol) was added, and the mixture was allowed to warm to room temperature slowly and stirred overnight. To the reaction mixture (0° C.) was added 5N sodium hydroxide solution (280 ml), and the mixture was stirred for 1 hour. The organic phase was washed with 2N HCl, water and brine. After removing the solvent, the crude product was purified by chromatography (6 cm, gradient elution with 10% to 30% ethyl acetate in hexane) to afford starting material (6.78 g) and compound 1002 (12.78 g, 52%). $^1$H NMR (200 MHz, CDCl$_3$) δ: 5.71 (s, 1H), 4.7 (br m, 1H), 2.5–1.0 (m, 27 H), 2.05 (s, 3H), 1.21 (s, 3H), 0.92 (d, J=6.5 Hz, 3H), 0.86 (d, J=7 Hz, 6H), 0.68 (s, 3H).

Preparation of compound 1003: A solution of compound 1002 (14.32 g, 32.3 mmol) in ethyl acetate (1.4 l) was purged with nitrogen, treated with platinum(IV) oxide (263 mg), and hydrogen gas (atmospheric) for 3 hours at room temperature. After filtration through Celite, the solution was evaporated and purified by flash chromatography (6 cm, gradient elution with 0–20% ethyl acetate in hexane) to yield pure compound 1003 (10.86 g, 76% yield). $^1$H NMR (200 MHz, CDCl$_3$) δ: 4.67 (br m, 1H), 2.4–1.0 (m, 29H), 2.02 (s, 3H), 1.10 (s, 3H), 0.90 (d, J=6.5 Hz, 3H), 0.86 (d, J=6.5 Hz, 6H), 0.65 (s, 3H); IR (KBr, cm$^{-1}$): 2950, 1730, 1707, 1471, 1373, 1264, 1032; MS(+ES): 445.7 (M+1).

Preparation of compounds 1004 and 1005: To a solution of compound 1003 (11.62 g, 26.1 mmol) in tetrahydrofuran (THF) (500 ml) was added 1M K-Selectride® (80 ml, 80 mmol) in THF at room temperature. After 5 hours at 50° C., the reaction mixture was cooled in an ice bath, and then treated with 30% hydrogen peroxide (45 ml) and saturated ammonium chloride solution (200 ml). The organic phase was separated and the aqueous phase was extracted with ether (3×100 ml), and the combined organic layers were washed with saturated sodium bicarbonate, ammonium chloride and water. After drying, the crude product was purified by chromatography (6 cm, gradient elution with 0–30% ethyl acetate in hexane) to afford compound 1004 (10.95 g, 24.5 mmol), which was dissolved in dichloromethane (200 ml) with dimethylaminopyridine (30.30 g, 248 mmol) and treated with acetic anhydride (40 ml, 424 mmol) for 19 hours. To this solution was added methanol (150 ml), and the solvent was evaporated. The residue was dissolved in ethyl acetate, washed with 2N hydrochloric acid solution (3×150 ml), water (100 ml), saturated sodium carbonate solution (3×100 ml) and brine (2×100 ml). The organic layer was dried, evaporated, and purified by flash chromatography (6 cm, gradient elution with 0–20% ethyl acetate in hexane) to yield compound 1005 (11.47 g, 90% yield). $^1$H NMR (200 MHz, CDCl$_3$) δ: 4.88 (m, 1H), 4.71 (br m, 1H), 2.08 (s, 3H), 2.02 (s, 3H), 2.0–1.0 (m, 29H), 0.92–0.83 (m, 12H), 0.64 (s, 3H); IR (KBr, cm$^{-1}$): 2954, 2867, 1730, 1468, 1367, 1257, 1025; Anal. calcd. for C$_{31}$H$_{52}$O$_4$: C=76.18, H=10.72; Found: C=76.09, H=10.56.

Preparation of compound 1006: A solution of compound 1005 (10.85 g, 22.2 mmol) and sodium cyanide (1.20 g, 24.4 mmol) in methanol (420 ml) was stirred overnight at room temperature, and then refluxed for 10 hours. The solvent was evaporated, and the residue was dissolved in dichloromethane and water, which was acidified with 2N hydrochloric acid solution. After another dichloromethane extraction, the organic layer was washed with brine, dried over magnesium sulfate, and evaporated to afford compound 1006 (9.22 g, 92% yield). $^1$H NMR (200 MHz, CDCl$_3$) δ: 4.89 (m, 1H), 3.62 (br m, 1H), 2.07 (s, 3H), 2.0–1.0 (m, 29H), 0.90 (d, J=6 Hz, 3H), 0.87 (d, J=6.5 Hz, 6H), 0.82 (s, 3H), 0.64 (s, 3H); IR (KBr, cm$^{-1}$): 3446, 2935, 1735, 1469, 1375, 1245, 1042, 941; MS(+ES): 470 (M+Na).

Preparation of compounds 1007, 1008 and 1009: To a solution of compound 1006 (892 mg, 2.0 mmol) in anhydrous dichloromethane (20 ml) under nitrogen (−10° to −5° C.) was added triethylamine (3 ml, 22 mmol) and methanesulfonyl chloride (0.40 ml, 5.2 mmol) in dichloromethane (4 ml). After 40 minutes, the mixture was poured into 1N hydrochloric acid solution (100 ml), and the organic phase was separated. After extracting with more dichloromethane (3×20 ml), the organic phase was washed with 1N hydrochloric acid solution (30 ml), saturated sodium bicarbonate solution (30 ml) and brine (2×30 ml). After drying over sodium sulfate, the solvent was evaporated to yield compound 1007, which was used for the next step without purification.

Crude compound 1007 was dissolved in dimethylformamide (50 ml), treated with sodium azide (2.0 g, 31 mmol), and heated to 100° C. for 18 hours. After cooling, the reaction mixture was diluted with water (250 ml), extracted with dichloromethane (3×150 ml), washed with water (3×100 ml), dried (Na$_2$SO$_4$), filtered, and evaporated to yield compound 1008, which was used in the next step without purification.

A solution of compound 1008 in anhydrous tetrahydrofuran (60 ml) was treated with 1M lithium aluminum hydride (20 ml, 20 mmol) and heated to reflux for 5 hours. After cooling in an ice bath, to the mixture was added water (50 ml) and then 2M sodium hydroxide solution (200 ml). The aqueous phase was extracted with dichloromethane (3×150 ml), followed by washing with brine (2×100 ml) and water (50 ml). The dried organic layer was evaporated to afford compound 1009, which was used without purification in the next step.

Preparation of compounds 1363 and 1364: Crude compound 1009 was dissolved in methanol (40 ml) and treated with 2N sodium hydroxide solution (40 ml) at 80° C. for 12 hours. After evaporation, water was added (40 ml), followed by extraction with dichloromethane (3×60 ml). After washing with brine (3×50 ml), the organic layer was dried ($Na_2SO_4$), filtered and evaporated. Purification by flash chromatography (2-cm diameter, elution with 95:4.5:0.5 dichloromethane:methanol:ammonium hydroxide) afforded compound 1363 (slower eluting; $^1$H NMR (200 MHz, $CDCl_3$) δ: 3.82 (m, 1H), 3.19 (m, 1H), 2.0–1.0 (m, 29H), 0.91 (d, J=6.5 Hz, 3H), 0.87 (d, J=6.5 Hz, 6H), 0.78 (s, 3H), 0.65 (s, 3H); IR (KBr, $cm^{-1}$): 3362, 2931, 1575, 1467, 1382; MS (+FAB): 404.4 (M+1)) and compound 1364 (faster eluting; $^1$H NMR (200 MHz, $CDCl_3$) δ: 3.4 (br m, 1H), 3.2 (m, 1H), 2.0–1.0 (m, 29H), 0.91 (d, J=6.5 Hz, 3H), 0.86 (d, J=6.5 Hz, 6H), 0.80 (s, 3H), 0.68 (s, 3H)). Each compound was dissolved in methanol, treated with excess 1N hydrogen chloride in ether, and evaporated to yield the hydrochloride salt. Compound 1363 (646 mg, 74% overall yield for 4 steps): Anal. calcd. for $C_{27}H_{49}NO$—HCl—$0.5H_2O$: C=72.20, H=11.44, N=3.12; Found: C=72.40, H=11.44, N=3.26. Compound 1364 (50 mg, 6% overall yield for 4 steps): MS(+FAB): 404.4 (M+1); Anal. calcd. for $C_{27}H_{49}NO$—HCl—$H_2O$: C=70.78, H=11.44, N=3.06; Found: C=71.02, H=11.33, N=3.35.

EXAMPLE R

Preparation of compounds 388 and 387:

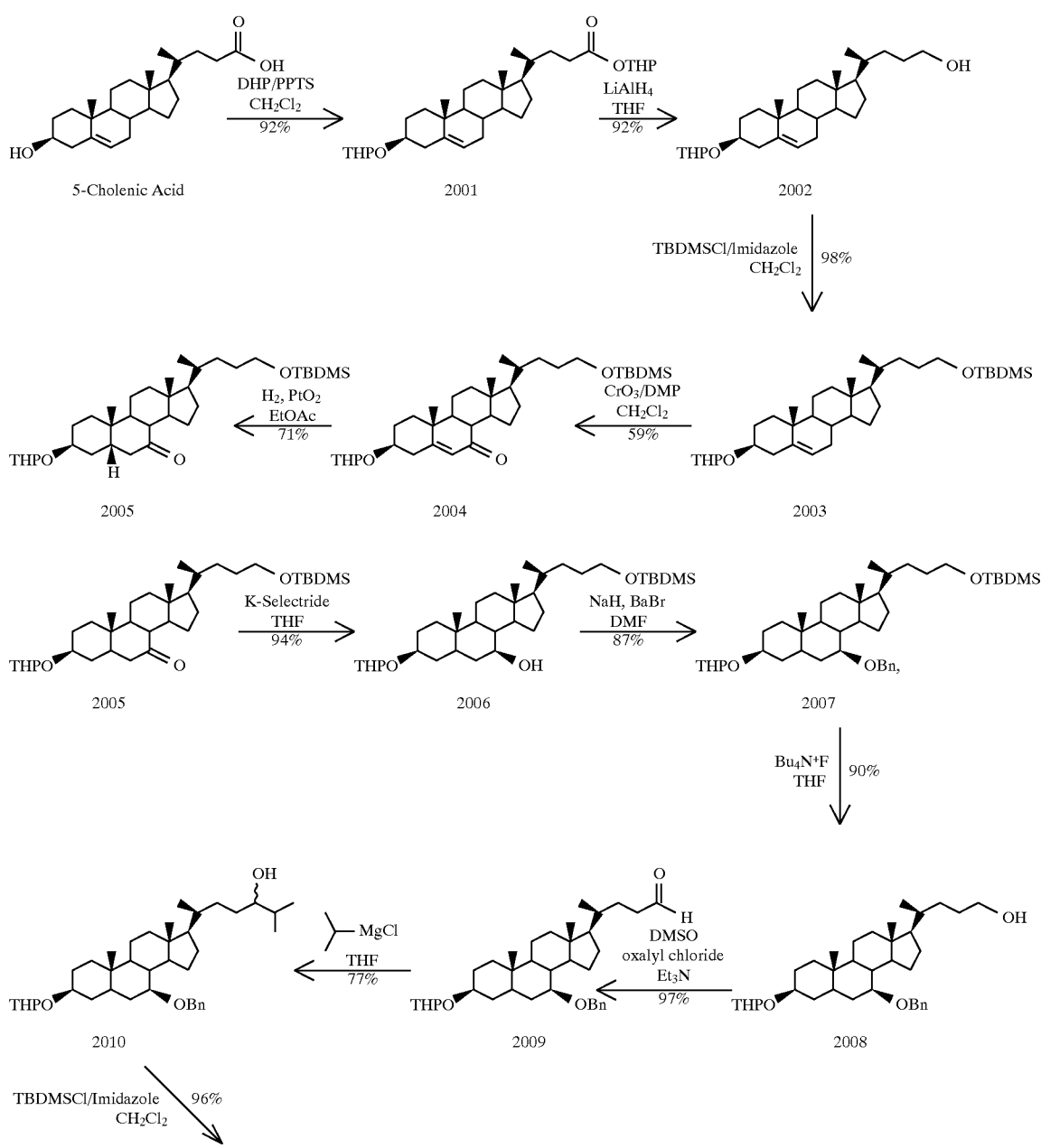

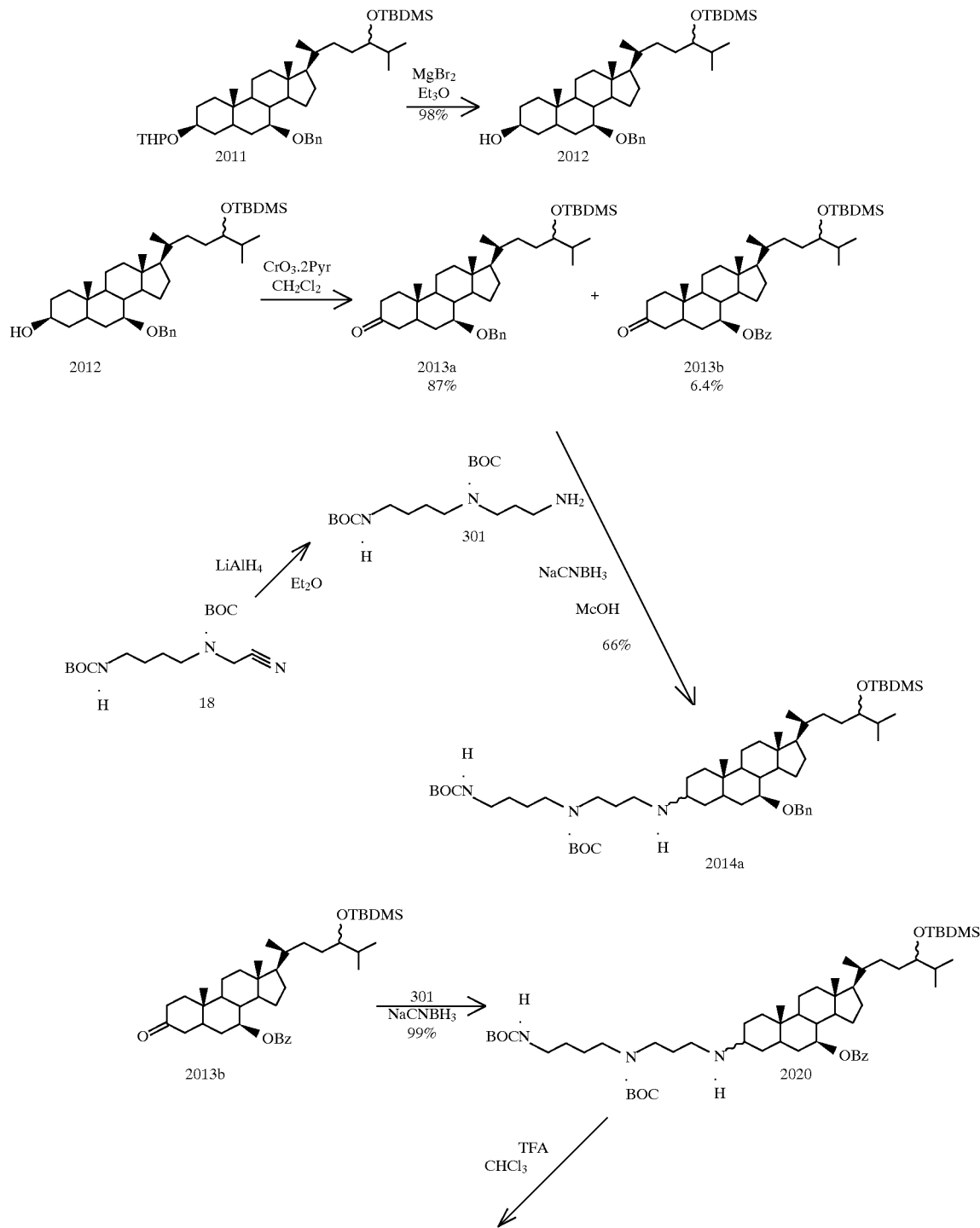

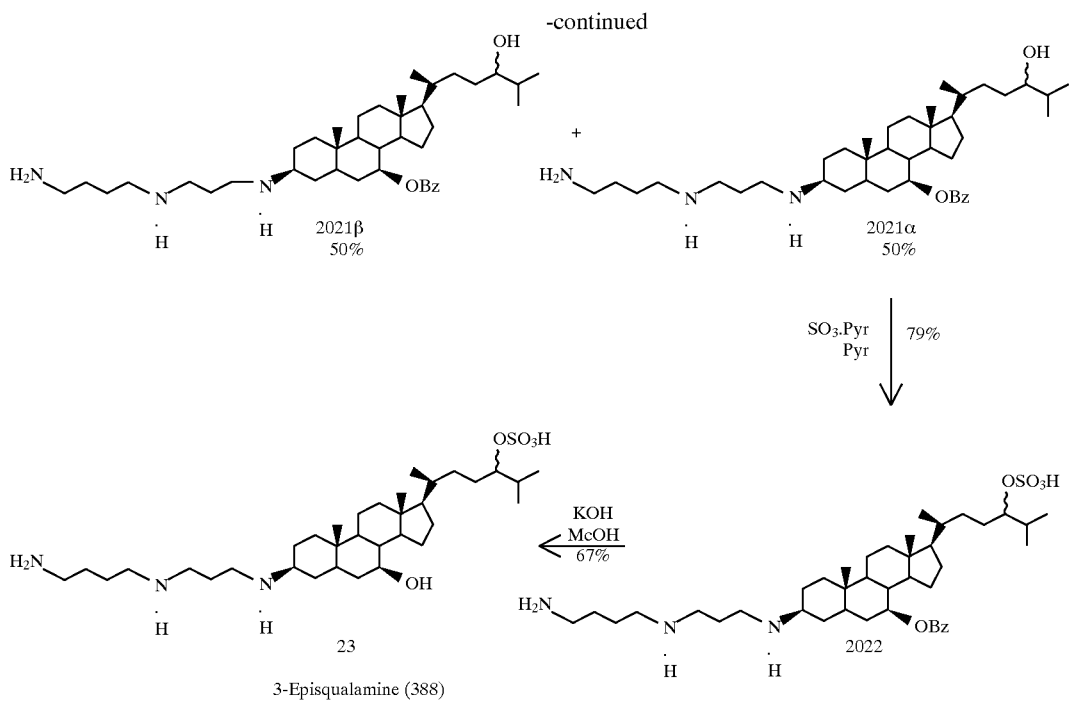

3-Episqualamine (388)

¹H-NMR spectra were obtained on a Varian XL-200 (200 MHz) or a Varian Unity-500 (500 MHz) NMR spectrometer. Infrared spectra were recorded on a Perkin Elmer 298 spectrometer. Direct insertion probe (DIP) chemical ionization mass spectral data were obtained on a Hewlett Packard HP 5087 GC-MS. Melting points were determined on a Thomas Hoover capillary melting point apparatus and are uncorrected. Elemental analyses were performed by Quantitative Technologies Inc., Whitehouse, N.J. FAB mass spectral data (low and high resolution) were obtained from M-Scan Inc., West Chester, Pa.

5-Cholenic acid was obtained from Steraloids and used as received. The following reagents were purchased from Aldrich Chemical Company and were used as received unless otherwise indicated: dihydropyran (distilled prior to use), p-toluenesulfonic acid, lithium aluminum hydride, t-butyldimethylsilyl chloride, imidazole, 3,5-dimethylpyrazole, platinum (IV) oxide, potassium tri-sec-butylborohydride (K-Selectrides®, 1M in THF), hydrogen peroxide (30%), sodium hydride (60% in mineral oil), benzyl bromide (distilled prior to use), tetrabutylammonium fluoride (1M in THF), oxalyl chloride, diisopropylethylamine, dimethylsulfoxide (distilled prior to use), isopropylmagnesium chloride (2M in THF), magnesium bromide, sodium cyanoborohydride (1M in THF), 10% palladium on carbon, and sulfur trioxide pyridine complex. THF and Et₂O were distilled from sodium/benzophenone ketyl. Pyridine was distilled from KOH. Methylene chloride and pentane were distilled from CaH₂. DMF was distilled from BaO under reduced pressure. Methanol was dried over 3 Å molecular sieves prior to use. PPTS was prepared via the method of Miyashita et al., *J. Org. Chem.* 42, 1977, 3772). Molecular sieves were dried in an oven (170° C.) overnight prior to use. Silica gel (EM Science Silica Gel 60, 230–400 mesh) was used for all flash chromatography.

Preparation of 3β-Tetrahydropyranyloxychol-5-en-24-oic acid 24-tetrahydropyranyl ester (2001):

5-Cholenic acid (7.58 g, 20 mmol) was suspended in a solution of dry CH₂Cl₂ (300 ml). Distilled dihydropyran (19.0 ml, 200 mmol) was added, followed by a catalytic amount of pyridinium p-toluene sulfonate (1.1 g, 4.0 mmol). The suspension was stirred at room temperature overnight under argon. During this period of time, the steroid went into solution. The resultant solution was washed with a aqueous saturated NH₄Cl solution (2x), aqueous saturated NaHCO₃ solution (2x), and aqueous saturated NaCl solution. The organic later was dried over anhydrous MgSO₄, filtered, and the solvent was removed in vacuo. The crude solid was purified by flash chromatography (SiO₂, hexanes/EtOAc (10:1), giving compound 2001 as a white solid (9.8 g, 18.5 mmol, 92%). ¹H NMR (500 MHz, CDCl₃) δ: 5.96 (brs, 1H, THP ester methine H), 5.37–5.32 (m, 1H, C-6 H), 4.72 (brs, 1H, THP ether methine H), 3.95–3.87 (m, 2H, THP CH₂O), 3.71–3.64 (m, 1H, THP CH₂O, 3.58–3.44 (m, 2H, THP CH₂O & C-3 H), 1.01 (s, 3H, C-19 H), 0.94 (d, J=6.3 Hz, 3H, C-21 H) 0.68 (s, 3H, C-18 H).

Preparation of 3β-Tetrahydropyranyloxychol-5-en-24-ol (2002):

Compound 2001 (16.1 g, 30 mmol) in dry tetrahydrofuran (THF, 150 ml) was added to a suspension of LiAlH₄ (5.5 g, 145 mmol) in dry THF (200 ml). The suspension was stirred at 0° C. with a mechanical stirrer under argon overnight. The resultant gray slurry was quenched with EtOAc, followed by aqueous saturated Na₂SO₄ solution. During the addition of the Na₂SO₄ solution, a white precipitate formed and the solution became clear. Anhydrous Na₂SO₄ was added, the mixture was stirred for 15 minutes, and then filtered. The filter cake was washed well with ethyl acetate and the filtrate was concentrated in vacuo. The resulting solid was purified by flash chromatography (SiO₂, hexanes:EtOAc 5:1) giving compound 2002 as a white solid (12.3 g, 27.7 mmol, 92%). ¹H NMR (500 MHz, CDCl₃) δ 5.37–5.32 (m, 1H, C-6 H), 4.72 (brs, 1H, THP methine H), 3.95–3.88 (m, 1H, THP CH₂O), 3.62–3.47 (m, 4H, THP CH₂O & C-3 H & C-24 H), 1.01 (s, 3H, C-19 H), 0.93 (d, J=6.6 Hz, C-21 H), 0.68 (s, 3H, C-18 H); IR (CHCl₃) 3610, 2900 cm⁻¹; MS (CI/isobutane) m/z 445 (M+1, 2%), 343 (M+1-THPOH, 100%); m.p. 130°–131° C.

Preparation of 24-t-Butyldimethylsilyloxy-3β-tetrahydropyranyloxychol-5-ene (2003):

Compound 2002 (7.6 g, 17 mmol) in dry $CH_2Cl_2$ (300 ml) was treated with a solution of t-butyldimethylsilylchloride (TBDMSCl, 1.0M) and imidazole (0.5M) in dry $CH_2Cl_2$ (38.0 ml, 38.0 mmol TBDMSCl). The solution was stirred at room temperature under argon overnight. The resultant solution was poured into an aqueous saturated $NaHCO_3$ solution and the mixture extracted with $CH_2Cl_2$ (3x). The combined organic layers were washed with saturated sodium chloride, dried over anhydrous $MgSO_4$, filtered, and the solvent removed in vacuo. The resultant solid was purified by flash chromatography ($SiO_2$, hexanes:EtOAc gradient from 20:1 to 5:1) giving compound 2003 (9.4 g, 17 mmol, 98%). $^1$H NMR (500 MHz, $CDCl_3$) δ: 5.38–5.32 (m, 1H, C-6 H), 4.72 (brs, 1H, THP methine H), 3.95–3.88 (m, 1H, THP $CH_2O$), 3.60–3.46 (m, 4H THP $CH_2O$ & C-3 H & C-24 H), 1.01 (s, 3H, C-19 H), 0.93 (d, J=6.6 Hz, C-21 H), 0.89 (s, 9H, t-Bu), 0.67 (s, 3H, C-18 H), 0.05 (s, 6H, TBDMS $CH_3$); IR ($CHCl_3$) 2900 cm$^{-1}$; MS (CI/isobutane) m/z 559 (M+1, 1%), 474 (M+1-THP, 12%), 457 (M+1-THPOH, 18%), 343 (M+1-THP-TBDMSOH, 6%), 325 (M+1-THPOH-TBDMSOH, 100%); m.p. 116°–118° C.; Anal. calcd. for $C_{35}H_{62}O_3Si$: C=75.21, H=11.18; Found: C=75.37, H=11.24.

Preparation of 24-t-Butyldimethylsilyloxy-3β-tetrahydropyranyloxychol-5-en-7-one (2004):

Chromium trioxide (6.43 g, 64.4 mmol) was suspended in dry $CH_2Cl_2$ (100 ml). The mechanically stirred suspension under argon was cooled to −78° C. via a dry-ice/acetone bath. 3,5-Dimethylpyrazole (6.18 g, 64.4 mmol) was added to the suspension as a solid and the mixture was allowed to stir for 25 minutes at −78° C. to ensure complete formation of the complex. Compound 2003 (3.10 g, 5.37 mmol) was then added to the mixture as a solid, and the reaction mixture was allowed to slowly warm to room temperature and stirred overnight. The mixture was then transferred to a one-neck 500 ml round-bottom flask and silica gel (flash grade) was introduced. The slurry was concentrated to a free-flowing solid which was introduced onto the top of a wet packed flash column ($SiO_2$) and the product was eluted with hexanes:ethyl acetate (gradient 30:1 to 15:1 to 6:1 to 3:1). The desired product, compound 2004 (1.80 g, 59%) was obtained as a white solid. $^1$H NMR (500 MHz, $CDCl_3$) δ: 5.65 & 5.63 (2S, 1H, C-6 H), 4.70–4.64 (m, 1H, THP methine), 3.90–3.81 (m, 1H, THP $CH_2O$), 3.70–3.62 (m, 1H, C-3H or THP $CH_2O$), 3.57 (t, J=6.6 Hz, 2H, C-24 H), 3.52–3.46 (m, 1H, C-3 H or THP $CH_2O$), 1.19 (s, 3H, C-19 H), 0.93 (d, J=6.3 Hz, C-21 H), 0.90 (s, 9H, t-butyl), 0.68 (s, 3H, C-18 H), 0.05 (s, 6H, TBDMS $CH_3$); IR ($CHCl_3$) 2900, 1650 cm$^{-1}$; MS (CI/isobutane) m/z 573 (M+1, 11%), 489 (M+1-THP, 100%); m.p. 118°–120° C.

Preparation of 24-t-Butyldimethylsilyloxy-3β-tetrahydropyranyloxy-5α-cholan-7-one (2005):

Compound 2004 (1.0 g, 1.75 mmol) was dissolved in EtOAc (75 ml) and platinum(IV) oxide (0.012 g, 0.049 mmol) was added. The mixture was placed on a hydrogenation apparatus (atmospheric). The set-up was evacuated to remove the dissolved oxygen and then hydrogen was introduced. The evacuation and introduction of hydrogen process was repeated 2 times. The reaction was stirred under hydrogen at atmospheric pressure for 2.5 hours. The reaction mixture was filtered through Celite and concentrated in vacuo. The crude product was purified by flash chromatography ($SiO_2$, hexanes:EtOAc gradient starting with 20:1) giving compound 2005 as a white solid (0.70 g, 71%).

24-t-Butyldimethylsilyloxy-3β-tetrahydropyranyloxy-5α-cholan-7β-ol was obtained as a by-product (21%). (Note: This by-product could be converted to the desired ketone 2005 with Collin's reagent in 64% yield.) Compound 2005: $^1$H NMR (500 MHz, $CDCl_3$) δ: 4.73–4.66 (m, 1H, THP methine H), 3.95–3.85 (m, 1H, THP $CH_2O$), 3.66–3.52 (m, 3H, THP $CH_2O$ & C-24 H), 3.50–3.45 (M, 1H, C-3 H), 1.08 (s, 3H, C-19 H), 0.91 (d, J=6.6 Hz, C-21 H), 0.89 (s, 9H, t-Bu), 0.64 (s, 3H, C-18 H), 0.04 (s, 6H, TBDMS $CH_3$); IR ($CHCl_3$) 2900, 1685 cm$^{-1}$; MS (CI/isobutane) m/z 575 (M+1, 85%), 491 (M+1-THP, 100%); m.p. 166°–170° C.; Anal. calcd. for $C_{35}H_{62}O_4Si$: C=73.12, H=10.87; Found: C=72.88, H=10.78.

Preparation of 24-t-Butyldimethyulsilyloxy-3β-tetrahydropyranyloxy-5α-cholan-7α-ol (2006):

K-Selectride® (potassium tri-sec-butylborohydride) (8.9 ml, 1M in THF, 8.9 mmol) was added dropwise via syringe to a solution of ketone 2005 (1.7 g, 3.0 mmol) in dry THF (50 ml) at room temperature under argon. The reaction mixture was heated to 50° C. in an oil bath and stirred for 5 hours. The mixture was allowed to cool to room temperature and then quenched by adding 30% $H_2O_2$ dropwise until the evolution of gas ceased. Saturated aqueous $NH_4Cl$ solution was added and the aqueous solution was extracted (3x) with $Et_2O$. The combined organic extracts were washed with aqueous saturated $NaHCO_3$ solution (2x), distilled $H_2O$ (2x), and aqueous saturated NaCl solution, dried over anhydrous $MgSO_4$, filtered, and the solvent was removed in vacuo. The crude product was purified by flash chromatography ($SiO_2$, hexanes:EtOAc 10:1) giving alcohol 2006 as a white solid (1.6 g, 94%). $^1$H NMR (500 MHz, $CDCl_3$) δ: 4.73–4.66 (m, 1H, THP methine H), 3.95–3.85 (m, 1H, THP $CH_2O$), 3.82 (s, 1H, C-7H), 3.66–3.52 (m, 3H, THP $CH_2O$ & C-24 H), 3.50–3.45 (m, 1H, C-3H), 1.08 (s, 3H, C-19H), 0.91 (d, J=6.6 Hz, C-21H), 0.89 (s, 9H, t-Bu), 0.64 (s, 3H, C-18H), 0.04 (s, 6H, TBDMS $CH_3$); MS (CI/isobutane) m/z 577 (M+1, 5%), 493 (M+1-THP, 22%), 475 (M+1-THPOH, 26%), 458 (M+1-THPOH-$H_2O$, 38%), 343 (M+1-THPOH-TBDMSOH, 80%), 325 (M+1-THPOH-TBDMSOH-$H_2O$, 100%); IR ($CHCl_3$) 3430, 2860 cm$^{-1}$; m.p. 130°–133° C.; Anal. calcd. for $C_{35}H_{64}O_4Si$: C=72.86, H=11.18; Found: C=72.69, H=11.32.

Preparation of 7α-Benzyloxy-24-t-butyldimethylsilyloxy-3β-tetrahydropyranyloxy-5α-cholane (2007):

A flame-dried round-bottom flask with stirring bar was charged with sodium hydride (60% in mineral oil, 28 mg, 0.69 mmol), equipped with a septum and a gas-needle inlet and flushed with argon. The mineral oil was removed by washing (3x) with dry pentane, and the pentane was removed to provide the sodium hydride as a powder. Dry DMF (2.0 ml) was added. A solution of alcohol 2006 (40 mg, 0.069 mmol) in dry THF (2 ml) was added dropwise via syringe. The reaction mixture was stirred overnight and then heated to 40° C. in an oil bath over a 20-minute period. Freshly distilled benzyl bromide (0.165 ml, 1.38 mmol) was added dropwise, and the reaction mixture was stirred at 40° C. for 10 hours. The reaction was allowed to cool to room temperature, and the solvent was removed under reduced pressure. The flask was placed under vacuum overnight to remove any residual DMF. The crude material was purified by flash chromatography ($SiO_2$, hexanes:EtOAc 50:1) giving compound 2007 as a white solid (40 mg, 0.060 mmol, 87%). A gradient of increasing EtOAc concentration provided other components, including the 7α-formate (1 mg, 1%) as well as recovered starting material (3 mg, 8%). Compound 2007: $^1$H NMR (500 MHz, $CDCl_3$) δ: 7.35–7.20

(m, 5H, benzyl Ar—CH$_2$), 4.73–4.66 (m, 1H, methine H), 4.535 (d, J=12.0 Hz, 1/2H, benzyl-CH$_2$), 4.53 (d, J=12.0 Hz, 1/2H, benzyl-CH$_2$), 4.26 (d, J=12.2 Hz, 1/2H, benzyl-CH$_2$), 4.245 (d, J=11.8 Hz, 1/2H, benzyl-CH$_2$), 3.95–3.85 (m, 1H, THP CH$_2$O), 3.66–3.52 (m, 3H, THP CH$_2$O & C-24H), 3.50–3.45 (m, 1H, C-3H), 1.08 (s, 3H, C-19H), 0.91 (d, J=6.6 Hz, C-21H), 0.89 (s, 9H, t-Bu), 0.64 (s, 3H, C-18 H), 0.04 (s, 6H, TBDMS CH$_3$); MS (CI/isobutane m/z 668 (M+1, 6%), 584 (M+1-THP, 18%), 475 (M+1-THPOH, 30%), 457 (M+1-THPOH-HOBn, 58%), 343 (M+1-THP-HOBn-TBDMSOH, 100%), 325 (M+1-THPOH-TBDMSOH-HOBn, 83%).

Preparation of 7α-Benzyloxy-3β-tetrahydropyranyloxy-5α-cholan-24-ol (2008):

Compound 2007 (0.0527 g, 0.079 mmol) in anhydrous THF (4 ml) under Ar was treated with tetrabutylammonium fluoride (TBAF) (0.237 ml, 1M in THF, 0.237 mmol). The solution was stirred until no starting material remained by TLC. The solvent was removed in vacuo, the residue taken up in 5 ml CH$_2$Cl$_2$, washed with 5 ml aqueous saturated NaHCO$_3$ solution, and the aqueous layer was extracted 2x with 5 ml CH$_2$Cl$_2$. The combined organic layers were dried over anhydrous MgSO$_4$, filtered, and the solvent removed in vacuo. Flash chromatography (SiO$_2$, 8:1 hexanes:EtOAc) gave compound 2008 (0.0395 g, 90%) as a white solid foam. $^1$H NMR (500 MHz, CDCl$_3$) δ: 7.35–7.34 (m, 5H, benzyl Ar—H), 4.71–4.69 (m, 1H, THP ether methine H), 4.585 (d, J=11.8 Hz, 1/2H, benzyl-CH$_2$), 4.58 (d, J=11.8 Hz, 1/2H, benzyl-CH$_2$), 4.315 (d, J=12.0 Hz, 1/2H, benzyl-CH$_2$), 4.29 (d, J=12.0 Hz, 1/2H, benzyl-CH$_2$), 3.94–3.90 (m, 1H, THP OCH$_2$), 3.62–3.58 (m, 3H, C-24 H & THP OCH$_2$), 3.50–3.48 (m, 1H, C-3 H), 3.45 (s, 1H, 7-H), 0.92 (d, J=6.6 Hz, 3H, C-21 H), 0.81 (s, 3H, C-19 H), 0.63 (s, 3H, C-18H) (Note: product is a mixture of diastereomers); IR (CHCl$_3$) 3600, 2900 cm$^{-1}$; MS (CI/isobutane) m/z 554 (M+1, 2%), 361 (M+1-THP-HOBn, 42%), 343 (M+1-THP-HPBn, H$_2$O, 100%); m.p. 52°–56° C.; Anal. calcd. for C$_{36}$H$_{56}$O$_4$: C=78.21, H=10.21; Found: C=77.93, H=10.39.

Preparation of 7α-Benzyloxy-3β-tetrahydropyranyloxy-5α-cholan-24-al (2009):

DMSO (0.01 ml, 0.14 mmol) in CH$_2$Cl$_2$ (0.1 ml) was added dropwise to a stirred solution of oxalyl chloride (0.008 ml, 0.0917 mmol) in anhydrous CH$_2$Cl$_2$ (2 ml) at −78° C. under anhydrous conditions (drying tube). This solution was stirred at −78° C. for 15 minutes. Steroid 2008 (0.0234 g, 0.0423 mmol) in dry CH$_2$Cl$_2$ (0.5 ml) was then added dropwise and the solution stirred for 40 minutes at −78° C. Diisopropylethylamine (DIPEA) (0.08 ml, 0.458 mmol) was added and the solution allowed to warm to 0° C. with stirring over a 30-minute period. Aqueous saturated NaHCO$_3$ solution (5 ml) was added and the solution extracted 3x with 5 ml CH$_2$Cl$_2$. The combined organic extracts were washed 2x with 5 ml of aqueous saturated NaCl solution, dried over anhydrous MgSO$_4$, filtered, and the solvent removed in vacuo. Flash chromatography (SiO$_2$, 10:1 hexanes:EtOAc) gave compound 2009 (0.0226 g, 97%) as a white solid foam. $^1$H NMR (500 MHz, CDCl$_3$) δ: 9.76 (s, 1H, C-24 H), 7.35–7.34 (m, 5H, benzyl Ar—H), 4.71–4.69 (m, 1H, THP ether methine H), 4.59 (d, J=11.8 Hz, 1/2H, benzyl-CH$_2$), 4.585 (d, J=11.8 Hz, 1/2H, benzyl-CH$_2$), 4.30 (d, J=12.0 Hz, 1/2H, benzyl-CH$_2$), 4.29 (d, J=12.0 Hz, 1/2H, benzyl-CH$_2$), 3.95–3.89 (m, 1H, THP OCH$_2$), 3.63–3.58 (m, 3H, C-24H & THP OCH$_2$), 3.50–3.47 (m, 1H, C-3H), 3.45 (s, 1H, 7-H), 2.49–2.42 (m, 1H, C-23H), 2.37–2.31 (m, 1H, C-23 H), 0.958 (d, J=6.5 Hz, 3H, C-21H), 0.81 (s, 3H, C-19 H), 0.63 (s, 3H, C-18 H) (Note: product is a mixture of diastereomers); IR (CHCl$_3$) 2900, 1700 cm$^{-1}$; MS (CI/isobutane) m/z 552 (M+1, 0.4%), 465 (M+1-THP, 3%), 449 (M+1-THPO, 14%), 375 (M+1-THP-Bn, 7%), 359 (M+1-THP-HOBn, 68%), 341 (M+1-THP-HOBn-H$_2$O, 100%); m.p. 50°–54° C.; Anal. calcd. for C$_{36}$H$_{54}$O$_4$: C=78.50, H=9.88; Found: C=78.11, H=10.04.

Preparation of 7α-Benzyloxy-3β-tetrahydropyranyloxycholestan-24ξ-ol (2010):

A solution of compound 2009 (0.374 g, 0.679 mmol) in anhydrous THF (10 ml) under argon was treated with isopropylmagnesium chloride (2 ml, 2M in THF, 5.43 mmol) at room temperature. The reaction was stirred until no starting material remained by TLC. Aqueous NH$_4$Cl solution (10%, 15 ml) was added to quench the reaction and the THEF was removed in vacuo. Distilled H$_2$O (5 ml) was added and the solution extracted 3x with 15 ml CH$_2$Cl$_2$. The combined organic layers were washed with aqueous saturated NaCl solution (15 ml), dried over anhydrous MgSO$_4$, filtered and the solvent removed in vacuo. Flash chromatography (SiO$_2$, 12:1 hexanes:EtOAc) gave compound 2010 (0.3117 g, 77%) as a white foam. $^1$H NMR (500 MHz, CDCl$_3$) δ: 7.35–7.34 (m, 5H, benzyl Ar-H), 4.71–4.69 (m, 1H, THP ether methine H), 4.585 (d, J=11.9 Hz, 1H, benzyl-CH$_2$), 4.31 (d, J=12.0 Hz, 1/2H, benzyl-CH$_2$), 4.295 (d, J=12.0 Hz, 1/2H, benzyl-CH$_2$), 3.94–3.91 (m, 1H, THP, OCH$_2$), 3.62–3.58 (m, 1H, THP OCH$_2$), 3.50–3.48 (m, 1H, C-3 H), 3.45 (s, 1H, C-7 H), 3.32–3.31 (m, 1H, C-24 H), 0.81 (s, 3H, C-19 H), 0.63 (d J=2.4 Hz, 3H, C-18 H) (Note: product is a mixture of diastereomers); IR (CHCl$_3$) 3605, 2900 cm$^{-1}$; MS (CI/isobutane) m/z 595 (M+1, 10%), 401 (M+1-THP-Bn-H$_2$O, 25%), 385 (M+1-THP-HOBn, H$_2$O, 100%); m.p. 55°–59° C.; Anal. calcd. for C$_{39}$H$_{62}$O$_4$: C=78.74, H=10.50; Found: C=78.65, H=10.54.

Preparation of 7α-Benzyloxy-24ξ-t-butyldimethylsilyloxy-362-tetrahydropyranyloxycholestane (2011):

Compound 2010 (0.050 g, 0.084 mmol) in dry CH$_2$Cl$_2$ (1 ml) was treated with a solution of t-butyldimethylsilylchloride (TBDMSCl, 0.5M) and imidazole (1.0M) in dry CH$_2$Cl$_2$ (0.80 ml, 0.40 mmol TBDMSCl). The reaction was stirred at room temperature under argon for 24 hours. Aqueous saturated NaHCO3 solution (5 ml) was added and the solution extracted 3x with 10 ml CH$_2$Cl$_2$. The combined organic layers were washed with 10 ml aqueous saturated NaCl solution and dried over anhydrous Na$_2$SO$_4$. Filtration and removal of solvent in vacuo followed by flash chromatography (SiO$_2$, 20:1 hexanes:EtOAc) gave the desired product 2011 (0.057 g, 96%) as a white solid. $^1$H NMR (500 MHz, CDCl$_3$) δ: 7.35–7.34 (m, 5H, benzyl Ar-H), 4.70–4.69 (m, 1H, THP ether methine H), 4.59 (d, J=12.0 Hz, 1H, benzyl-CH$_2$), 4.315 (d, J=12.3 Hz, 1/2H, benzyl-CH$_2$), 4.31 (d, J=12.0 Hz, 1/2H, benzyl-CH$_2$), 3.94–3.91 (m, 1H, THP OCH$_2$), 3.62–3.58 (m, 1H, THP OCH$_2$), 3.50–3.48 (m, 1H, C-3H), 3.45 (s, 1H, C-7 H), 3.37–3.35 (m, 1H, C-24 H), 0.89 (d, J=1 Hz, 9H, SiC(CH$_3$)$_3$, diastereomeric at C-24), 0.81 (s, 3H, C-19 H), 0.62 (s, 3H, C-18 H), 0.04 & 0.03 (2s, 6H, Si(CH$_3$)$_2$, diastereotopic and/or diastereomeric) (Note: product is a mixture of diastereomers); IR (CHCl$_3$) 2900 cm$^{-1}$; MS (CI/isobutane) m/z 709 (M+1, 20%), 367 (M+1-THPOH-HOBn-TBDMSOH, 100%); m.p. 52°–58° C.; Anal. calcd. for C$_{45}$H$_{76}$O$_4$S: C=76.21, H=10.80; Found: C=76.11, H=10.81.

Preparation of 7α-Benzyloxy-24ξ-t-butyldimethylsilyloxycholestan-3β-ol (2012):

Compound 2011 (0.057 g, 0.0803 mmol) was dissolved in dry Et$_2$O (3 ml) under argon. MgBr$_2$ (0.142 g, 0.771 mmol) was added quickly as a solid and the reaction was stirred until no starting material remained by TLC. $H_2O$ (10 ml) was added and the mixture was extracted 3x with 10 ml $Et_2O$. The combined organic layers were dried over anhydrous $MgSO_4$, filtered and the solvent removed in vacuo. Flash chromatography ($SiO_2$, 7:1 hexanes:EtOAc) gave compound 2012 (0.0493 g, 98%) as a white foam. $^1H$ NMR (500 MHz, $CDCl_3$) δ: 7.36–7.35 (m, 5H, benzyl-Ar H), 4.59 (d, J=12.0 Hz, 1H, benzyl-$CH_2$), 4.34 (d, J=12.0 Hz, 1H, benzyl-$CH_2$), 3.65–3.60 (m, 1H, C-3H), 3.475 (d, J=2.4 Hz, 1H, C-7H), 3.40–3.36 (m, 1H, C-24H), 0.91 (d, J=0.9 Hz, 9H, $SiC(CH_3)_3$, diastereomeric at C-24), 0.82 (s, 3H, C-19 H), 0.65 (s, 3H, C-18 H), 0.05 & 0.04 (s, 6H, $Si(CH_3)_2$, diastereotopic and/or diastereomeric) (Note: product is a mixture of diastereomers); IR ($CHCl_3$) 3600, 2900 $cm^{-1}$; MS (CI/isobutane) m/z 624 (M+1, 3%), 501 (M+1-OTHP, 6%), 385 (M+1-OTHP-TBDMS, 68%), 367 (M+1-THPOH-TBDMSOH, 100%); m.p. 55°–58° C.; Anal. calcd. for $C_{40}H_{68}O_3Si$: C=76.86, H=10.97; Found: C=76.69, H=10.87.

Preparation of 7α-Benzyloxy-24ξ-t-butyldimethyl-silyloxycholest-3-one (2013a) and 7α-Benzoyloxy-24ξ-t-butyldimethylsilyloxycholestan-3-one (2013b):

A solution of compound 2012 (0.229 g, 0.3664 mmol) in dry $CH_2Cl_2$ (30 ml) was treated with Collin's reagent (0.385 g, 1.49 mmol). The mixture was stirred at room temperature overnight under argon. At this time no starting material remained by TLC. Celite was added and the mixture was stirred for 20 minutes and then filtered through a pad of Celite. The cake was rinsed well with $CH_2Cl_2$. The solvent was removed in vacuo. Flash chromatography ($SiO_2$, 20:1 hexanes:EtOAc) gave the desired product 2013a (0.198 g, 87%) as a white solid along with the 7α-benzoate 2013b (0.015 g, 6.4%) as a white foam. Note: If the reaction was run at higher concentration, a higher yield of the benzoate was obtained. Compound 2013a: $^1H$ NMR (500 MHz, $CDCl_3$) δ: 7.35–7.27 (m, 5H, benzyl Ar-H), 4.55 (d, J=11.7 Hz, 1H, benzyl-$CH_2$), 4.32 (d, J=11.7 Hz, benzyl-$CH_2$), 3.495 (d, J=2.0 Hz, 1H, C-7 H), 3.38–3.35 (m, 1H, C-24 H), 1.02 (s, 3H, C-19 H), 0.90 (d, J=0.8 Hz, 9H, $SiC(CH_3)_3$, diastereomeric at C-24), 0.67 (s, 3H, C-18 H), 0.04 & 0.03 (s, 6H, $Si(CH_3)_3$, diastereotopic and/or diastereomeric) (Note: product is a mixture of diastereomers); IR ($CHCl_3$) 2900, 1690 $cm^{-1}$; MS (CI/isobutane) m/z 624 (M+1, 50%), 534 (M+1-Bn, 7%), 518 (M+1-OBn, 36%), 492 (M+1-HOSi $(Me)_2$t-Bu, 28%), 383 (M+1-$C_{14}H_{30}$OSi, 100%). Compound 2013b: $^1H$ NMR (500 MHz, $CDCl_3$) δ: 8.03 (d, J=7.3 Hz, 2H, benzoate Ar H), 7.59 (t, J=7.4 Hz, lH, Ar H), 7.48 (t, J=7.7 Hz, 2H, Ar H), 5.20 (br s, 1H, C-7 H), 3.35–3.31 (m, 1H, C-24 H), 1.08 (s, 3H, C-19 H), 0.86 (d, J=3.7, 9H, $SiC(CH_3)_3$), 0.71 (s, 3H, C-18 H) (Note: product is a mixture of diastereomers); IR ($CHCl_3$) 2900, 1690 $cm^{-1}$; MS (CI/isobutane) m/z 637 (M+1, 3%), 516 (M+1-OBz, 16%), 382 (M+1-OBz-TBDMSOH, 100%); m.p. 62°–65° C.

Preparation of 7α-Benzyloxy-3ξ-(5,10-di-t-butoxycarbonyl-1,5,10-triazadecyl)-24ξ-t-butyldimethylsilyloxycholestane (2014a):

A mixture of compound 2013a (0.07 g, 0.11 mmol), approximately 2 equivalents of amino compound 301 (based on 60% yield for the reduction of compound 2018 to compound 301), and 3 Å molecular sieves (0.5 g) in MeOH (6 ml, dried over 3 Å sieves) was stirred for 12 hours at room temperature under argon. $NaCNBH_3$ (0.33 ml, 1M in THF, 0.33 mmol) was added and the solution stirred for 24 hours at room temperature under argon. The mixture was filtered through Celite and the cake was washed well with MeOH and $CH_2Cl_2$ and the solvents were removed in vacuo. The residue was dissolved in $CH_2Cl_2$ (10 ml), washed 2x with 5 ml $H_2O$ made basic with aqueous NaOH solution (5%), and washed 2x with 5 ml aqueous saturated NaCl solution. The combined aqueous layers were back-extracted with $CH_2Cl_2$, and the combined organic layers were dried over anhydrous $MgSO_4$. Filtration, removal of the solvent in vacuo, and flash chromatography ($SiO_2$, gradient of increasing polarity from 2% MeOH in $CH_2Cl_2$ to 10% MeOH in $CH_2Cl_2$) gave the desired product 2014a (0.07 g, 66%) and a more polar product, compound 2014b, which is missing one t-BOC group and is contaminated with excess amine. Compound 2014a: $^1H$ NMR (500 MHz, $CDCl_3$) δ: 7.36–7.28 (m, H, benzyl-Ar H), 4.63 (d, J=12.0 Hz, 1/2H, benzyl-$CH_2$), 4.58 (d, J=12.0 Hz, 1/2H, benzyl-$CH_2$), 4.33 (t, J=1.25 Hz, 1H, benzyl-$CH_2$), 3.49 (s, 1H, C-7 H), 3.46–3.14 (m, 8H, N(BOC)$CH_2$ & C-24 H), 2.91–2.86 (m, 2H, $NCH_2$), 1.47–1.41 (m, 18H, 2xCOC$(CH_3)_3$), 9.90 (s, 9H, $SiC(CH_3)_3$), 0.84 (s, 3H, C-19H), 0.64 (s, 3H, C-18H), 0.05 & 0.04 (s, 6H, $Si(CH_3)_2$ diastereotopic and/or diastereomeric) (Note: This product is a mixture of diastereomers).

Preparation of 7α-Benzyloxy-3β-(1,5,10-triazadecyl) cholestan-24ξ-ol (2015β) and 7α-benzyloxy-3α-(1,5,10-triazadecyl)cholestan-24ξ-ol (2015a):

TFA (1.8 ml, 24 mmol) was added to a solution of compound 2014a (0.386 g, 0.4 mmol) in $CHCl_3$ (15 ml) at room temperature. The reaction was stirred until no starting material remained by TLC. The solvent was removed in vacuo and the residue purified by preparative TLC ($SiO_2$, 2000 μm, 6:3:1 $CH_2Cl_2$:MeOH:$NH_4OH$, $R_f$=0.46) to give the desired 3β product 2015β (0.122g, 48%) and the 3α isomer 2015α (0.109 g, 43%). Compound 2014b could be treated with TFA under the same conditions to give compounds 2015α and 2015β. Compound 2015β: $^1H$ NMR (500 MHz, $CD_3OD$) δ: 7.32–7.35 (m, 5H, benzyl-Ar H), 4.57 (d, J=11.7 Hz, 1H, benzyl-$CH_2$), 4.31 (d, J=11.7 Hz, 1H, benzyl-$CH_2$), 3.52 (s, 1H, C-7H) 3.22–3.21 (m, 2H, C-24H & $NCH_2$), 2.86 (t, J=7.1 Hz, 2H, $NCH_2$), 2.81 (t, J=6.6 Hz, 2H, $NCH_2$), 2.74 (t, J=7.0 Hz, 2H, $NCH_2$), 2.67 (t, J=6.3 Hz, 2H, $NCH_2$), 0.85 (s, 3H, C-19H), 0.683 (s, 1.5H, C-18, diastereomeric at C-34), 0.678 (s, 1.5H, C-18, diastereomeric at C-24); MS (pos. FAB) m/z 638.6 (M+1, 100%). Compound 2015α: $^1H$ NMR (500 MHz, $CD_3OD$) δ: 7.35–7.22 (m, 5H, benzyl-Ar H), 4.61 (d, J=11.4 Hz, 1H, benzyl-$CH_2$), 4.28 (d, J=11.5 Hz, 1H, benzyl-$CH_2$), 3.53 (s, 1H, C-7 H), 3.43 (s, 1H, C-3 H), 3.24–3.20 2H, C-24 H & $NCH_2$), 3.11 (t, J=7.1 Hz, 2H, $NCH_2$), 3.08–3.02 (m, 2H, $NCH_2$), 2.96 (t, J=6.9 Hz, 2H, $NCH_2$), 0.85 (s, 3H, C-19H), 0.691 (s, 1.5H, C-18, diastereomeric at C-24), 0.686 (s, 1.5H, C-18, diastereomeric at C-24); MS (pos. FAB) m/z 638.6 (M+1, 100%).

Preparation of 3β-(1,5,10-Triazadecyl)cholesta-7α,24ξ-diol (2016):

To a solution of compound 2015β (0.0128 g, 0.02 mmol) in absolute EtOH (8 ml) was added a catalytic amount of 10% Pd/C and 2 drops of concentrated hydrochloric acid. The mixture was placed on a Parr hydrogenation apparatus and shaken under 55 psi ($H_2$) for 24 hours. The solution was filtered through a pad of Celite, and the cake was washed well with EtOH and MeOH, and the solvents removed in vacuo. The desired product 2016 (0.0074 g, 68%) was obtained. If the product was pure by TLC, it was used without further purification. If impurities were observed by TLC, the material was purified by flash chromatography ($SiO_2$, 15:4:1 $CH_2Cl_2$:MeOH:$NH_4OH$). $^1H$ NMR (500 MHz, $CD_3OD$) δ: 3.79 (s, 1H, C-7 H) 3.22–3.13 (m, 6H, 2x$CH_2N$ & C-24H & C-3 H), 3.09 (t, J=7.4, 2H, $CH_2N$), 2.99 (t, J=7.3 Hz, 2H, $CH_2N$), 0.87 (s, 3H, C-19 H), 0.694 (s, 1.5H, C-18 H, diastereomeric at C-24), 0.691 (s, 1.SH, C-18 H, diastereomeric at C-24).

Preparation of squalamine (compound 1256):

Compound 2016 (0.0176 g, 0.032 mmol) was dissolved in a solution of concentrated hydrochloric acid in MeOH (1 ml concentrated hydrochloric acid in 10 ml MeOH). The solution was stirred for 15 minutes and the solvent removed in vacuo. To the crude, dried procluct was added $SO_3$-pyridine complex (0.010 g, 0.064 mmol) and the flask was flushed with argon. Dry pyridine (1 ml) was added, the solution was warmed to 80° C. in an oil bath and stirred for 2 hours. MeOH (2 ml) was added. The flask was removed from the oil bath and the mixture was stirred for 15 minutes. The solvent was removed in vacuo, and the residue was resuspended in MeOH and filtered through a pad of Celite. The cake was washed well with MeOH. Flash chromatography ($SiO_2$, 12:4:1 $CH_2Cl_2$:MeOH:$NH_4OH$) gave the desired product 1256 (0.0113 g, 56%) as a white solid. $^1H$ NMR (500 MHz, $CD_3OD$) δ: 4.13–4.10 (m, 1H, C-24H), 3.79 (s, 1H, C-7H), 3.22–3.10 (m, 5H $CH_2N$), 3.08 (t, J=6.7 Hz, 2H, $CH_2N$), 2.98 (t, J=6.8 Hz, 2H, $CH_2N$), 0.87 (s, 3H, C-19H), 0.70 (s, 3H, C-18 H); MS (pos. FAB) m/z 628.4 (M+1, 57%), 548.5 (M+1-$SO_3$, 23%), 530.5 (M+1-$H_2SO_4$, 100%); high resolution MS (pos. FAB) m/z 628.4669 (calcd.: 628.4723).

Preparation of 5,10-Di-t-butoxycarbonyl-1,5,10-triazadecane (301):

Nitrile 2018 (0.0624 g, 0.181 mmol) in dry $Et_2O$ (0.30 ml) was added to a suspension of $LiAlH_4$ (0.024 g, 0.63 mmol) in dry diethyl ether (1 ml) at 0° C. The mixture was stirred at 0° C. for 30 minutes. Aqueous NaOH solution (1M) was added to quench excess $LiAlH_4$, and the resulting white suspension was filtered through a pad of Celite. The cake was washed well with $Et_2O$, and the combined organic layers were washed with $H_2O$. The $H_2O$ layer was extracted with $Et_2O$ and the combined ether layers were washed with aqueous saturated NaCl solution, dried over anhydrous $MgSO_4$, filtered and the solvent removed in vacuo. The $^1H$ NMR spectrum (500 MHz) of the crude product 301 (0.056 g, 88%) matched that reported in the literature (*Tetrahedron* 46, 1990, 3267–3286), and the material was used crude.

Preparation of 7α-Benzoyloxy-3ξ-(5,10-di-t-butoxycarbonyl-1,5,10-triazadecyl)-24ξ-t-butyldimethylsilyloxycholestane (2020):

Compound 2013b (0.110 g, 0.1726 mmol) was converted to compound 2020 (0.166 g, 99%) using the previously described procedure for the conversion of compound 2013a to compound 2014a. $^1H$ NMR (500 MHz, $CDCl_3$) δ: 8.19 (d, J=7.6 Hz, 1/2H, benzoate-Ar H), 8.05 (d, J=7.4 Hz, 3/2H, benzoate-Ar H), 7.61–7.58 (m, 1H, benzoate-Ar H), 7.55–7.45 (m, 2H, benzyl-Ar H), 5.23 (s, 1/4H, C-7 H), 5.16 (s, 3/4H, C-7H), 4.78–4.64 (m, 1H), 3.40-3.22 (m, 2H), 3.20–3.06 (m, 3H, $NCH_2$), 2.98–2.8 (m, 4H, $NCH_2$), 0.673 (s, 1.5H, C-18, diastereomeric at C-24), 0.667 (s, 1.5H, C-18, diastereomeric at C-24).

Preparation of 7α-Benzoyloxy-3α-(1,5,10-triazadecyl)cholestan-24ξ-ol (2021a) and 7α-benzoyloxy-3β-(1,5,10-triazadecyl)cholestan-24ξ-ol (2021β):

Compound 2020 (0.166 g, 0.1717 mmol) was converted to compounds 2021α and 2021β (quantitative yield of a 1:1 mixture of the 3α and 3β products) in the same manner as described previously for the conversion of compound 2014a to compounds 2015α and 2015β. Compound 2021β: $^1H$ NMR (500 MHz, $CD_3OD$) δ: 8.01 (d, J=8.3 Hz, 2H, benzoate-Ar H), 7.61–7.59 (m, 1H, benzoate-Ar H), 7.51–7.45 (m, 2H, benzyl-Ar H), 5.14 (s, 1H, C-7H), 3.20–3.15 (m, 1H), 2.90–2.75 (m, 4H, $NCH_2$), 2.72 (t, J=6.9 Hz, 2H, $NCH_2$), 2.65 (t, J=6.7 Hz, 2H, $NCH_2$), 0.85 (s, 3H, C-19H), 0.726 (s, 1.5H, C-18, diastereomeric at C-24), 0.723 (s, 1.5H, C-18, diastereomeric at C-24); MS (pos. FAB) m/z 652.5 (M+1, 100%), 530.5 (M+1-HOBz, 6%). Compound 2021α: $^1H$ NMR (500 MHz, $CD_3OD$) δ: 8.01 (d, J=8.3 Hz, 2H, benzoate-Ar H), 7.61–7.59 (m, 1H, benzoate-Ar H), 7.51–7.45 (m, 2H, benzyl-Ar H), 5.12 (s, 3H, C-7 H), 3.19–3.15 (m, 1H), 2.86 (s, 1H), 2.70–2.60 (m, 4H, $NCH_2$) 2.60–2.54 (m, 2H, $NCH_2$), 2.54–2.49 (m, 2H, $NCH_2$) 0.73 (s, 3H, C-18, diastereomeric at C-24); MS (pos. FAB) m/z 652.5 (M+1, 100%), 530.5 (M+1-HOBz, 10%).

Preparation of 7α-Benzoyloxy-3α-(1,5,10-triazadecyl)cholestan-24ξ-sulfate (2022):

Compound 2021α (0.0214 g, 0.0328 mmol) was converted to compound 2022 (0.0190 g, 79%) as previously described for the conversion of compound 2016 to compound 2017. $^1H$ NMR (500 MHz, $CD_3OD$) δ: 8.21–8.14 (m, 2H, benzoate-Ar H), 7.62–7.50 (m, 2H, benzoate-Ar H), 5.18–5.09 (m, 1H, C-7 H), 4.22–4.16 (m, 1/2H, C-24 H), 4.10–4.06 (m, 1/2H, C-24 H), 3.43 (br s, 1H, C-3 H), 3.22–3.10 (m, 5H, $CH_2N$), 3.09 (t, J=7.5 Hz, 2H, $CH_2N$), 3.04 (br s, 2H, $CH_2N$), 2.99–2.96 (m, 2H, $CH_2N$), 0.60 (s, 3/2H, C-18 H), 0.52 (s, 3/2H, C-18 H) (Note: compound is a mixture of diastereomers at C-24).

Preparation of 3-Episqualamine (388):

Compound 2022 (0.066 g, 0.085 mmol) was dissolved in methanolic KOH (5%, 5 ml) and refluxed for 7 hours. No starting material remained by TLC. Neutralization with 5% (v/v) concentrated hydrochloric acid in methanol followed by removal of the solvent and flash chromatography ($SiO_2$, 12:4:1 $CH_2Cl_2$:MeOH:$NH_4OH$) gave the desired product 2023 (0.0365 g, 67%). $^1H$ NMR (500 MHz, $CD_3OD$) δ: 4.14–4.09 (m, 1H, C-24 H), 3.80 (s, 1H, C-7H), 3.48 (s, 1H, C-3H), 3.24–3.15 (m, 4H, $CH_2N$), 3.10 (t, J=7.4 Hz, 2H, $CH_2N$), 3.01 (t, J=7.1 Hz, 2H, $CH_2N$), 0.86 (s, 3H, C-19 H), 0.69 (s, 3H, C-18H); MS (pos. FAB) m/z 628.5 (M+1, 18%), 548.5 (M+1-$SO_3$, 65%), 530.4 (M+1-$H_2SO_4$, 100%); high resolution MS (pos. FAB) m/z 628.4713 (calcd.: 628.4723).

Preparation of 3-Episqualamine Dessulfate (3α-(1,5,10-Triazadecyl)cholestan-7α,24ξ-diol, 387):

Compound 2015α (0.089 g, 0.1397 mmol) was converted to compound 387 (0.0372 g, 49%) as described for the conversion of compound 2015β to compound 2016. $^1H$ NMR (500 MHz, $CD_3OD$) δ: 3.80 (s, 1H, C-7 H), 3.48 (s, 1H, C-3 H), 3.24–3.15 (m, 4H, $CH_2N$), 3.10 (t, J=7.4 Hz, 2H, $CH_2N$), 3.00 (t, J=7.3 Hz, 2H, $CH_2N$), 0.86 (s, 3H, C-19H), 0.69 (2s, 3H, C-18 H), MS (pos. FAB) m/z 548.5 (M+1, 100%); high resolution MS (pos. FAB) 548.5162 (calcd.: 548.5155).

EXAMPLE S

Preparation of compound 399:

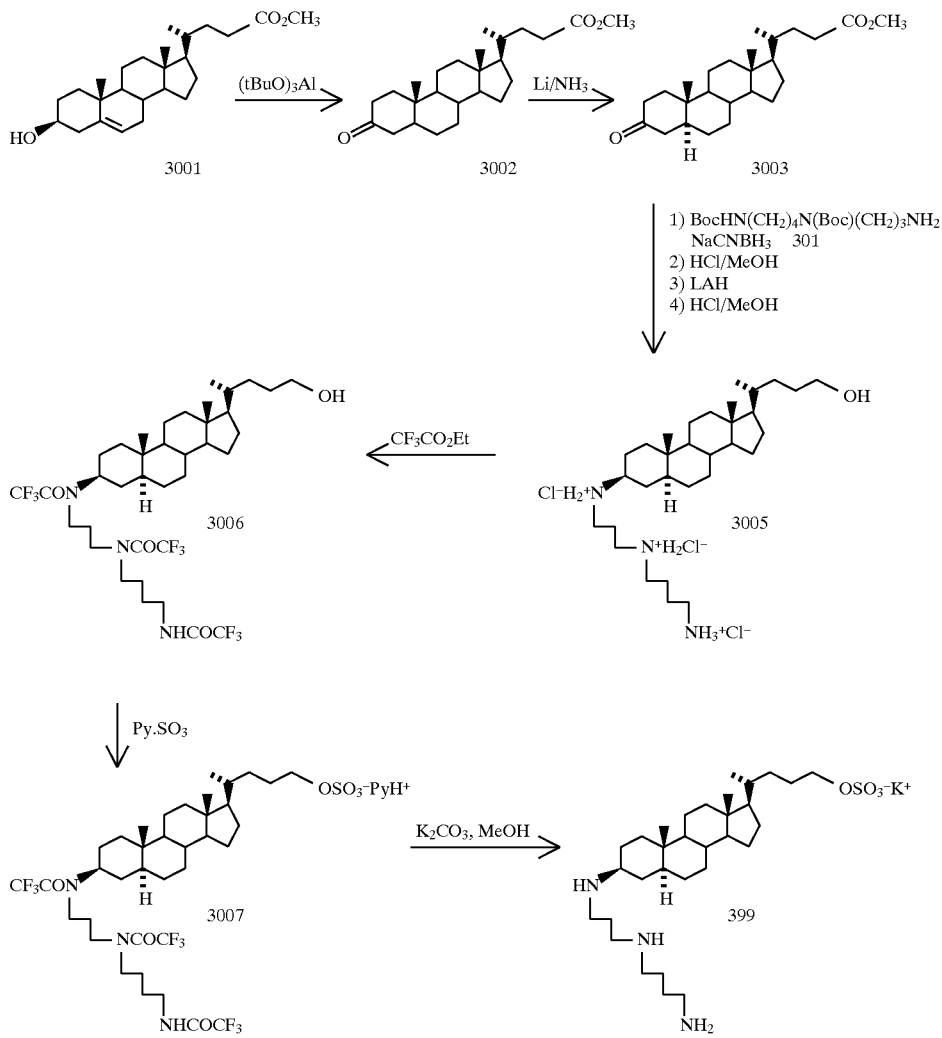

Preparation of 3-oxo-4-cholenic acid methyl ester 3002:

A solution of 3β-hydroxy-5-cholenic acid methyl ester 3001 (24.16 g, 57.11 mmol), aluminum tri-t-butoxide (56.27 g, 228.43 mmol) and isopropylmethylketone (50 ml) in dry toluene (150 ml) was stirred and heated to 120° C. (oil bath) for 6 hours. The reaction mixture was then cooled to room temperature diluted with toluene (100 ml) and acidified with 2NHCl (70 ml). The organic layer was separated, and the aqueous layer extracted with toluene (3×50 ml). The combined organic extracts were washed with water (1×50 ml), saturated $NaHCO_3$ (2×50 ml), water (1×50 ml), brine (1×50 m), dried ($MgSO_4$), filtered and evaporated in vacuo to get the crude product. Flash chromatography of the crude product using toluene followed by a gradient of ethyl acetate/hexane (5, 10, 20 and 40%) solvent systems gave a pure white solid, 3-oxo-4-cholenic acid methyl ester 3002 (13.43 g, 60%). $^1$H NMR (400 MHz, $CDCl_3$) δ: 0.71 (3H, s, 18-$CH_3$), 0.90 (3H, d, 21-$CH_3$), 1.17 (3H, S, 19-$CH_3$), 3.66 (3H, s, $CO_2CH_3$) and 5.71 (1H, s, 4-H).

Preparation of 3-oxo-5α-cholanic acid methyl ester 3003:

Into a solution of 3-oxo-4-cholenic acid methyl ester 3002 (13.0 g, 23.68 mmol) in dry ether (50 ml) was added distilled liquid ammonia (70 ml) at −78° C. Lithium (1.0 g, 144.1 mmol) was added in small portions until a blue coloration persisted for 10 minutes, after which the solution was quenched with solid $NH_4Cl$ (50 g). Ammonia was evaporated, and the resulting residue was partitioned between water (100 ml) and ether (150 ml). The aqueous solution was extracted further with ether (3×50 ml). The combined extracts were washed with brine (1×70 ml), dried ($MgSO_4$), filtered and concentrated in vacuo to get the crude product. Flash chromatography of the crude product in silica gel using ethyl acetate:hexane (2:8) gave pure 3-oxo-5α-cholanic acid methyl ester 3003 (3.85 g, 29%). $^1$H NMR (400 MHz, $CDCl_3$) δ: 0.69 (3H, s, 18-$CH_3$, 0.91 (3H, d, 21-$CH_3$), 1.02 (3H, s, 19-$CH_3$) and 3.66 (3H, s, $CO_2CH_3$).

Preparation of N-(3'-Aminipropyl)-N,N'-(di-tert-butoxycarbonyl)-1,4-diaminobutane 301:

(a) To a solution of 1,4-diaminobutane (8.6 g, 97.6 mmol) in methanol (3.0 ml) was added a solution of acrylonitrile (6.2 g, 116.8 mmol) in methanol (3.0 ml) at 0° C., and the mixture was stirred for 12 hours. Evaporation of the solvent in vacuo afforded N-(2'-cyanoethyl)-1,4-diaminobutane as a colorless oil (11.0 g, 80%). $^1$H NMR (400 MHz, $CDCl_3$) δ: 1.45 (4H, br, —$CH_2CH_2$—), 2.46 (2H, t), 2.58 (2H, t), 2.62 (2H, t) and 2.84 (2H, t).

(b) To a solution of N-(2'-cyanoethyl)-1,4-diaminobutane (5.6 g, 40 mmol) in dichloromethane (140 ml) was added dropwise a solution of di-t-butyldicarbonate (19.2 g, 88 mmol) in dichloromethane (20 ml) at room temperature, and the mixture was stirred for 12 hours. The organic solvent was removed in vacuo and the residual oil was dissolved in ethyl acetate (150 ml), and washed with saturated NaHCC)$_3$ (2×75 ml), water (2×75 ml), brine (75 ml), dried (MgSO$_4$), filtered and evaporated to get the crude viscous oil. The crude product was purified by flash chromatography in silica gel to give pure (N-(2'-cyanoethyl)-N,N'-(di-t-butoxycarbonyl)-1,4-diaminobutane as a colorless viscous oil (8.4 g, 75%). $^1$H NMR (400 MHz, CDCl$_3$) δ: 1.44 (9H, s, t-Boc), 1.46 (9H, merged s, t-Boc), 2.60 (2H, m), 3.15 (2H, m), 3.28 (2H, t) and 3.45 (2H, t); CIMS (m/e): 342 (M+1, 62.7%), 239 (100%), 186 (83.1%).

(c) To a suspension of lithium aluminum hydride (1.8 g, 48.9 mmol) in dry ether (300 ml) was added a solution of N-(2'-cyanoethyl)-N,N'-(di-t-butoxycarbonyl)-1,4-diaminobutane (4.8 g, 13.8 mmol) in dry ether (150 ml) dropwise at 0° C., and the mixture was stirred for 30 minutes. The excess lithium aluminum hydride was quenched with 1N NaOH at 0° C. and the resulting white suspension wads filtered through Celite and washed with ether, and the ether extract was washed with brine, dried (MgSO$_4$), filtered and evaporated in vacuo to get a crude oil. The crude product was purified by flash chromatography in silica gel to give pure N-(3'-aminopropyl)-N,N'-(di-t-butoxycarbonyl)-1,4-diaminobutane 301 (3.3 g. 68%) as a colorless oil. $^1$H NMR (400 MHz, CDCl$_3$) δ: 1.44 (18H, s, 2(t-Boc)), 2.68 (2H, t), 3.05–3.25 (6H, br), and 4.65 (1H, br); CIMS (m/e): 346 (M$^+$1, 100%), 290 (3.1%), 246 (32.2%).

Preparation of 3β-N-1-{N[3-(4-Aminobutyl)]-1,3-diaminopropane}-24-hydroxy-5α-cholane trihydrochloride 3005:

To a solution of 3-oxo-5α-cholanic acid methyl ester 3003 (3.0 g, 7.73 mmol) and N-(3'-aminopropyl)-N,N'-(di-t-butoxycarbonyl)-1,4-diaminobutane 301 (4.01 g, 11.60 mmol) in methanol (150 ml) was added 3 Å molecular sieves (10 g) and NaCNBH$_3$ (0.73 g, 11.61 mmol). The reaction mixture was stirred at room temperature for 16 hours. After filtering through Celite, methanol was removed in vacuo. The residue was dissolved in methanol (50 ml) and then methanol pre-saturated with HCl gas (15 ml) was added. The reaction mixture was stirred at room temperature for 6 hours. After removing methanol in vacuo, the crude product was dissolved in tetrahydrofuran (100 ml) and then lithium aluminum hydride (1.50 g, 39.52 mmol) was added in one portion. The reaction mixture was gently refluxed for 8 hours. The reaction mixture was cooled to 0° C. (ice bath), then a solution of 2N NaOH was added dropwise until white solid granulates were formed. Tetrahydrofuran was decanted and the residue further extracted with toluene (3×50 ml), and the combined organic extracts were dried (K$_2$CO$_3$), filtered and evaporated in vacuo to get the residue. The residue was dissolved in dry methanol (50 ml) and then methanol pre-saturated with HCl gas (20 ml) was added. After one hour, excess methanol was removed in vacuo to get white solid. The crude product: was purified by flash chromatography in silica gel using chloroform:methanol:isopropylamine (15:1:1) to get pure 3β-N-1-{N[3-(4-aminobutyl)]-1,3-diaminopropane}-24-hydroxy-5α-cholane trihydrochloride 3005 (1.10 g, 24%). $^1$H NMR (400 MHz, CD$_3$OD) δ: 0.71 (3H, s, 18-CH$_3$), 0.89 (3H, s, 19-CH$_3$), 096 (3H, d, 21-CH$_3$), 2.90–3.40 (9H, m) and 3.51 (2H, br t, CH$_2$O); MS-FAB (positive): 490 (M$^+$+1, 100%), 419 (8%) and 360 (7.5%)

Preparation of 3β-N-1-{N[3-(4-Trifluoroacetyl) aminobutyl)]-1,3-di(trifluoroacetyl)diaminopropane}-24-hydroxy-5α-cholane 3006:

To a solution of 3β-N-1-{N[(3-(4-aminobutyl)]-1,3-diaminopropane}-24-hydroxy-5α-cholane trihydrochloride 3005 (0.95 g, 1.58 mmol) in dry methanol (20 ml) was added dry triethylamine (2.29 ml, 15.8 mmol) followed by ethyl trifluoroacetate (2.80 ml, 23.53 mmol) at room temperature, and the mixture was stirred for 20 hours. After removal of excess methanol and low boiling organic reagents in vacuo produced a white residue. The residue was dissolved in ethyl acetate (50 ml) and then washed with 2N HCl (3×20 ml), water (2×20 ml), saturated NaHCO$_3$ (3×20 ml) and brine (1×20 ml), dried (MgSO$_4$), filtered and evaporated in vacuo to get an almost pure white solid, 3β-N-1-{N[3-(4-trifluoroacetyl)aminobutyl)]-1,3-di (trifluoroacetyl) diaminopropane}-24-hydroxy-5α-cholane 3006 (0.77 g, 73%). HNMR (400 MHz, CDCl$_3$) δ: 0.71 (3H, , 18-CH$_3$), 0.89 (3H, s, 19-CH$_3$), 0.96 (3H, d, 21-CH$_3$), 3.01–3.57 (11H, m, 4×CH$_2$N+1×CHN+CH$_2$O).

Preparation of 3β-N-1-{N[3-[4-Trifluoroacetyl) aminobutyl)]-1,3-di(trifluoroacetyl)diaminopropane}-24-hydroxy-5α-cholane 24-pyridinium sulfate 3007:

To a solution of compound 3006 (0.70 g, 1.05 mmol) in dry pyridine (20 ml) was added sulfur trioxide pyridine complex (0.75 g, 4.71 mmol) at room temperature, and the mixture was stirred for 6 hours. The excess pyridine was removed in vacuo to get solid residue, from which the sulfated compound was extracted with chloroform (5×20 ml). Removal of chloroform gave white solid, 3β-N-1-{N [3-(4-trifluoro-acetyl)aminobutyl)]-1,3-di(trifluoroacetyl) diaminopropane}-24-hydroxy-5α-cholane 24-pyridinium sulfate 3007 along with excess reagent (1.0 g). The crude product was used in the next step without further purification.

Preparation of 3β-N-1-{N[3-(4-Aminobutyl)]-1,3-diaminopropane}-24-hydroxy-5α-cholane 24-potassium sulfate (399):

To a solution of crude compound 3007 (1.0 g) in methanol (25 ml) was added a solution of potassium carbonate in water (10 ml) at room temperature, and the mixture was stirred overnight. After 18 hours, the excess methanol and water were removed in vacuo to get the residue. The residue was extracted with methanol (3×30 ml). The combined methanol extracts were concentrated in vacuo to get crude product. Flash chromatography of the crude product in silica gel using dichloromethane:methanol:ammonium hydroxide (7:2:1) (dried over MgSO$_4$ before use) gave white solid, 3β-N-1-{N[3-(4-aminobutyl)]-1,3-diaminopropane}-24-hydroxy-5α-cholane 24-potassium sulfate or compound 399 (0.22 g, 35% based on compound 3006). $^1$H NMR (400 MHz, CD$_3$OD) δ: 0.74 (3H, s, 18-CH$_3$), 0.92 (3H, s, 19-CH$_3$), 1.0 (3H, d, 21-CH$_3$), 2.95–3.24 (9H, m) and 4.00 (2H, br t, CH$_2$OSO$_3$); MS-FAB (positive) (m/e): 570 (M$^+$+2, 85%), 490 (44%), 430 (15%), 402 (16%), MS-FAB (negative) (m/e): 568 (M$^+$, 3.7%), 495 (10%), 452 (7%), 438 (17%), 423 (14%).

EXAMPLE T

Preparation of compound 1436:

This compound can be readily prepared from squalamine through the coupling of β-alanine aldehyde, followed by reduction, as shown in the following scheme:

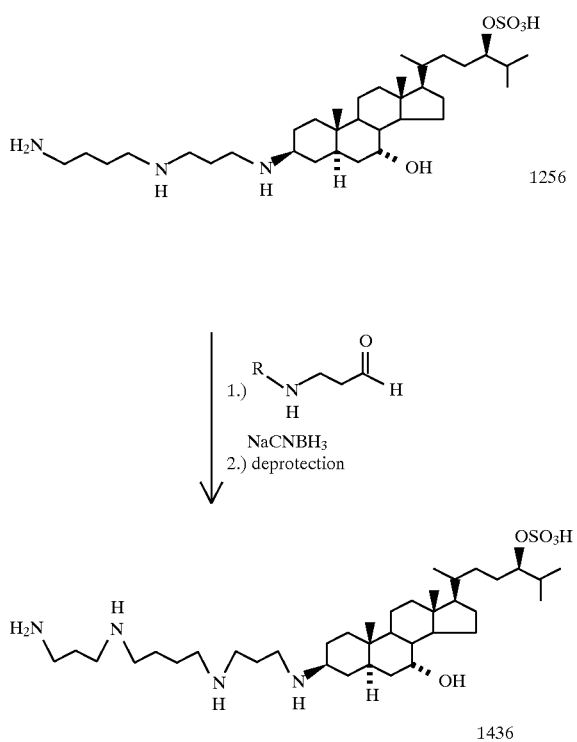

The above approach permits the ready conversion of squalamine, present-in large amounts in shark liver, to compound 1436, present in about 5% the quantity of squalamine.

Additional aminosterol compounds such as those shown in Tables I and II herein can be prepared in manners analogous to those given above.

Therapeutic Activities and Utilities

Aminosterol compounds such as squalamine have been discovered to be effective inhibitors of NHE. In seeking to elucidate the antimicrobial mechanism of action for squalamine, squalamine has been found to advantageously inhibit a specific NHE isoform—the compound inhibits NHE3, but not NHE1. In addition, squalamine has been determined to inhibit the exchanger through a special mechanism. The special and advantageous effects and utilities of squalamine and other aminosterols are further evident from the results of the experimental tests discussed below.

Specific Inhibition of NHE3:

To determine the specificity of squalamine's inhibition of NHEs, squalamine was assayed against a cell line expressing either human NHE1 or human NHE3 following procedures outlined in Tse et al., J. Biol. Chem. 268, 1993, 11917–11924. Internal pH was measured either following acid loading or in the absence of an acid-loading challenge, with the results shown in FIGS. 1A and 1B.

Specifically, PS120 fibroblasts transfected with rabbit NHE3 were grown in supplemented Dulbecco's-modified Eagle's medium as described by Levine et al., J. Biol. Chem. 268, 1993, 25527–25535. Transfected cells grown on glass coverslips were then assayed for internal. pH changes following treatment with 5 µg/ml squalamine using the fluorescent dye BCECF-AM (2',7'-bis(carboxyethyl)-5(6)-carboxyfluorescein-acetoxymethyl ester) as a pH indicator as described by Levine et al. For cells acid-preloaded by exposure to 40 mM NH$_4$Cl, the rate of pH recovery as a function of restored extracellular sodium ion concentration was monitored, with the results being shown in FIG. 1A. For cells not acid-preloaded, the actual internal pH value was monitored as a function of time following addition of squalamine, with the results depicted in FIG. 1B.

Figure 1A:
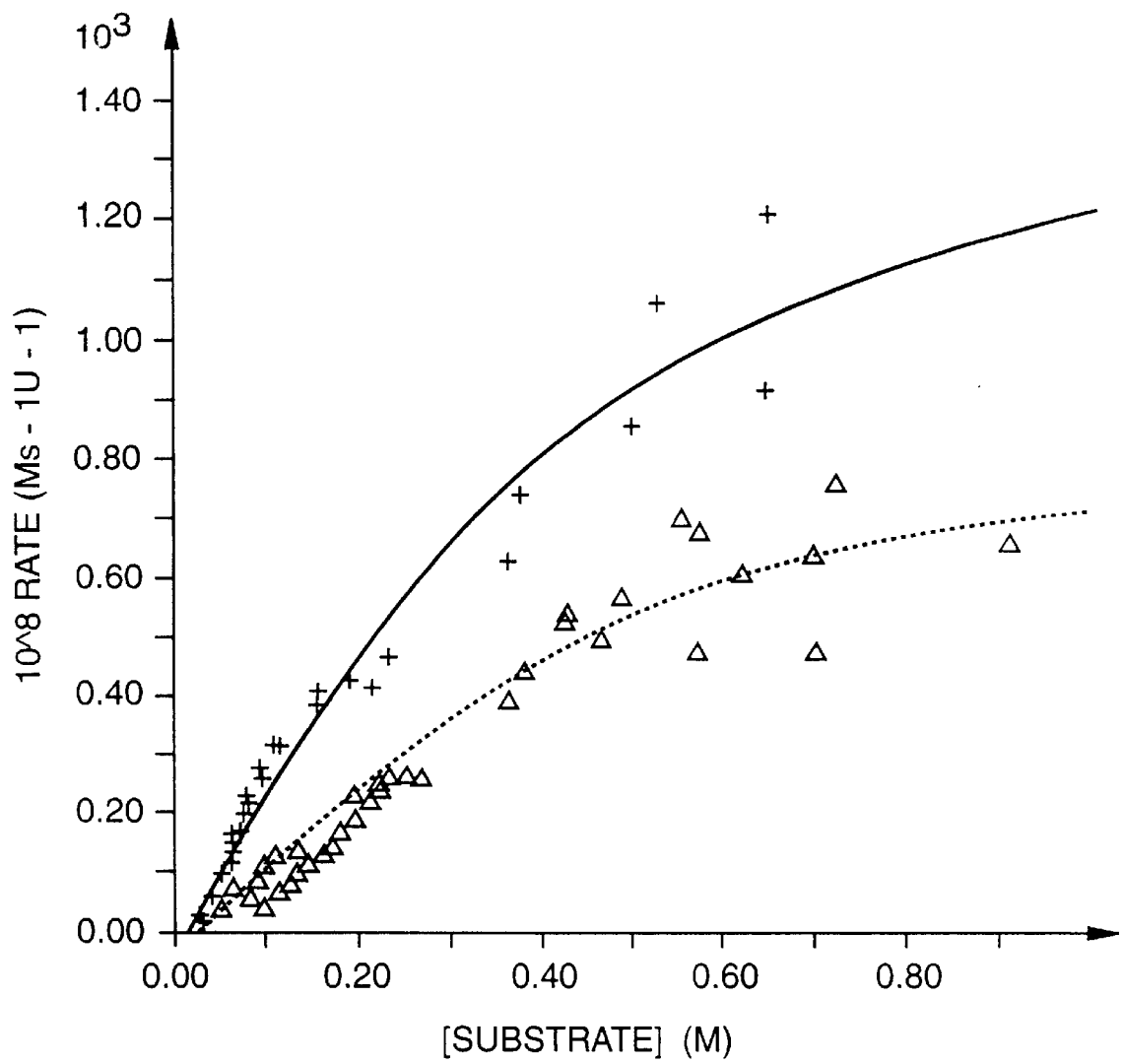
FIGS. 17A and 1 show the effect of compound 353 versus squalamine on human melanoma.
Figure 1B:
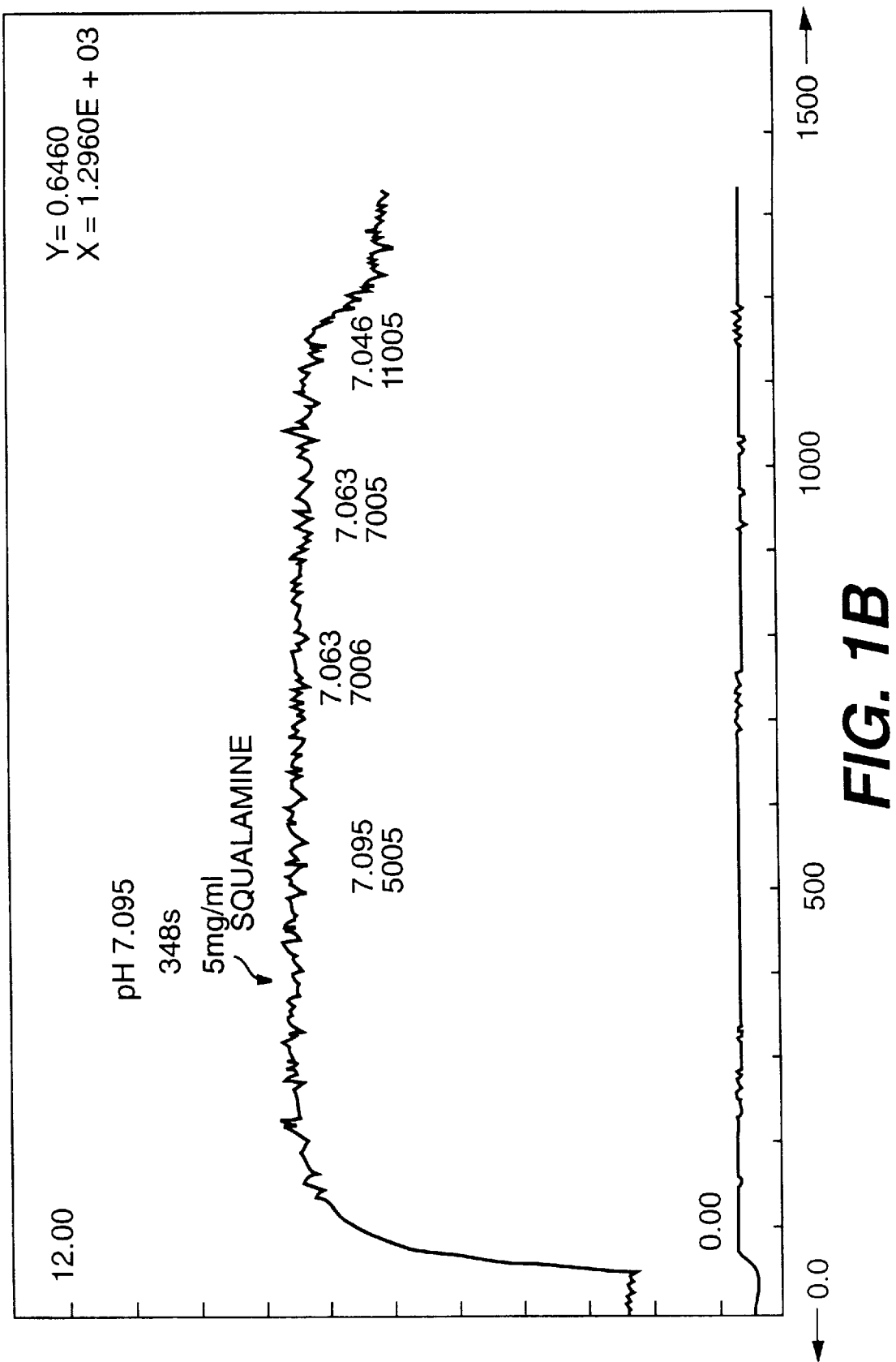

As seen in FIGS. 1A and 1B, squalamine inhibited NHE3 with respect to proton concentration at both $K_m$ and $V_{max}$ levels. In contrast, existing agents such as amiloride affected only $V_{max}$.

Thus, the aminosterol squalamine not only reduces the absolute number of protons that can be secreted by the cell (the $V_{max}$ effect), but also forces the cell to fall to a lower pH in the presence of this inhibitor (the $K_m$ effect). As a consequence, the sodium/proton exchanger is more profoundly inactivated by squalamine than by amiloride.

Figure 2A:
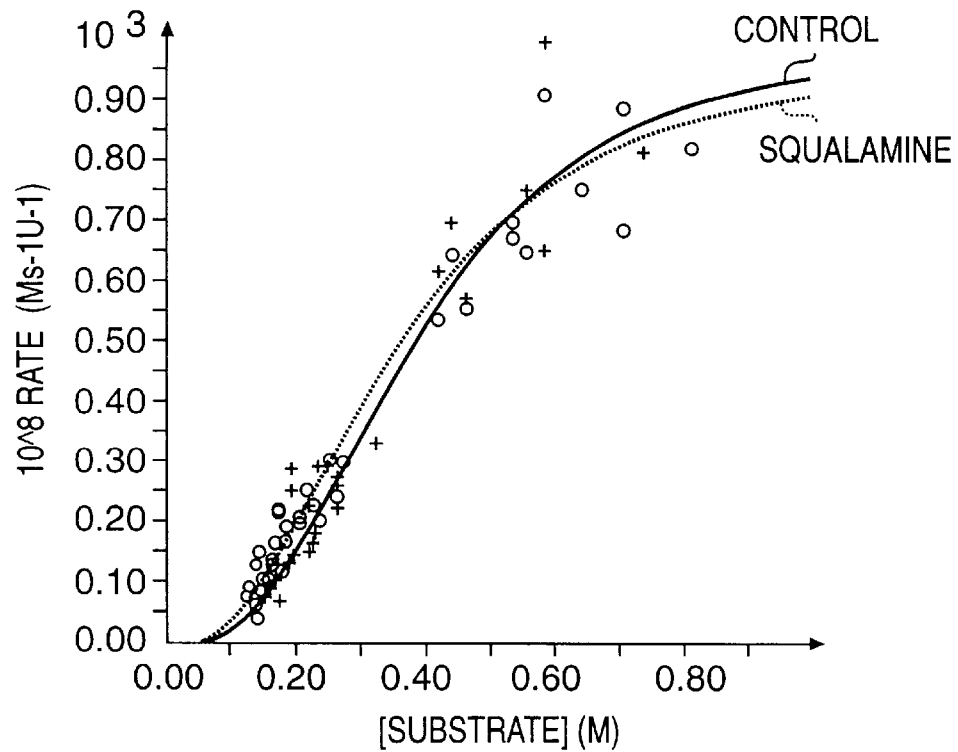
Figure 2B:
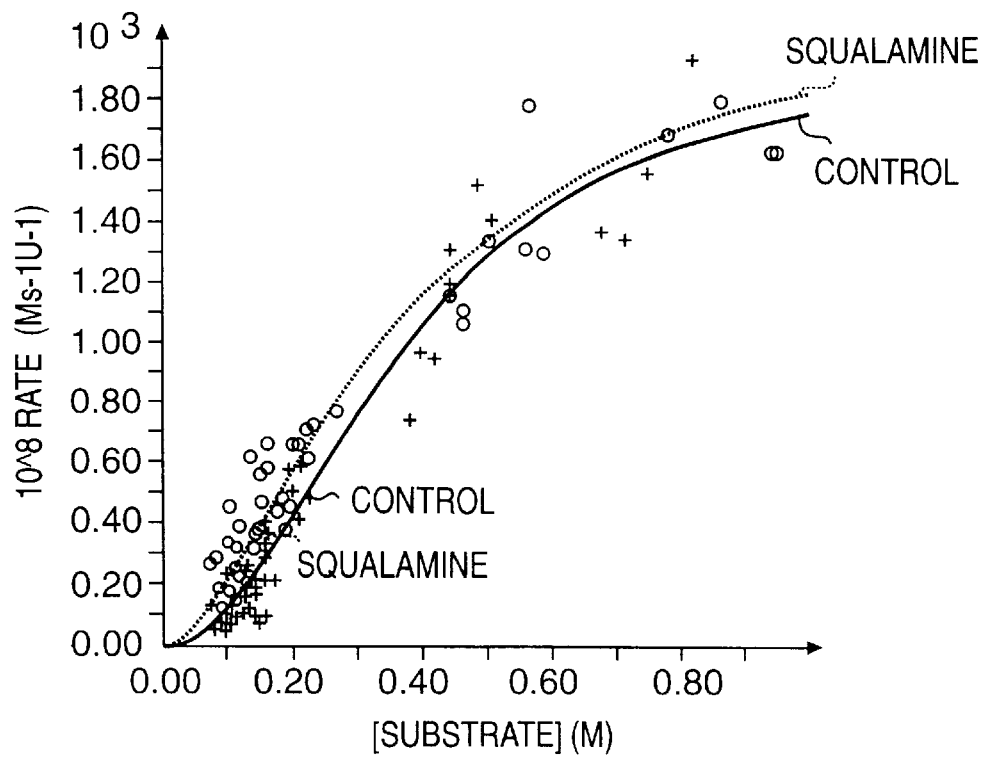

In contrast to its effects on NHE3 shown in FIGS. 1A and 1B, squalamine exhibited no inhibitory activity against human NHE1 or rabbit NHE1 as shown in FIGS. 2A and 2B. PS120 fibroblasts transfected with rabbit or human NHE1 were grown as described above. Transfected cells expressing rabbit NHE1 (FIG. 2A) or human NHE1 (FIG. 2B) grown on glass coverslips were then assayed for internal pH changes following treatment with 5 µg/ml squalamine using the fluorescent dye BCECF-AM with cells acid-preloaded by exposure to 40 mM NH$_4$Cl. The rate of pH recovery as a function of restored extracellular sodium ion concentration was monitored.

In addition, as demonstrated by FIG. 1B, the resting pH of these cells was also inhibited. Thus, squalamine's effect on proton exchange causes the cell to drop to a lower pH in its presence before activation of the pump occurs.

Through these studies, squalamine has been discovered to be a distinct inhibitor with specificity for NHE3 over NHE1. Moreover, squalamine has been identified as an inhibitor that causes a cell to drop to a lower pH before the pump is activated. The results shown in FIGS. 1A, 1B, 2A and 2B demonstrate that squalamine exhibits a unique NHE specificity.

The Expression of NHE3:

Such a specific effect for NHE3 is important for several reasons. NHE3, being present on apical surfaces of a limited number of cell types, is more specialized than NHE1. A cell of particular interest therapeutically is the endothelial cell.

Using PCR, the expression of this antiporter in both human microvascular and human pulmonary artery endothelial cells has now been demonstrated. Total RNA was isolated from primary human pulmonary artery endothelial cells (HPAEC), human melanoma cell line wm1617, and human microvascular endothelial cells (HMVEC) by a modification of the method of Chomczynski et al., Anal. Biochem. 162, 1987, 156, and then reverse-transcribed with MMLV reverse transcriptase using a first strand cDNA synthesis kit (Clontech Laboratories, Palo Alto, Calif.). Human small-intestine total RNA obtained from Clontech was also reverse-transcribed in the same fashion.

Approximately 80 ng of the cDNA product were then amplified in a 50-µl reaction mixture using reagents from the AmpliTaq DNA Polymerase kit (Perkin Elmer, Norwalk, Conn.) and containing 400 ng each of two oligonucleotides specific for human NHE3 (B13: 5'-CATCTGGACCTGGAACACG-3'; B14: 5'-CGTAGCTGATGGCATCCTTC-3') using one thermal cycle of 5',94° C., and then 38 cycles of 50",94° C., 1',57° C., 2',71° C., and finally 10',72° C. before cooling to 4° C. Twenty µl of this sample was analyzed on a 1.7% agarose gel. The expected NHE3 PCR band of about 550 bp was seen in most instances, as indicated in Table 2 below.

One µl of each PCR reaction was then further analyzed by nested PCR in a 50-µl reaction mix using two internal primers (B15: 5'-CTGGTCTTCATCTCCGTGTAC-3'; B16: 5'-AGCTCGTGGAA-GACATTCAGG) with a 5',94° C. program of thermal cycling, then 35 cycles of 50",94° C., 1',58° C., 2',71° C., and finally 10',72° C. before cooling to 4° C. About: 20 μl of this reaction was analyzed on another 1.7% agarose gel. The expected NHE3 PCR band of about 490 bp was seen in all cases as noted in the table below. DNA sequencing of the HPAEC and HMVEC nested PCR bands from both ends confirmed they had the expected human NHE3 sequences.

TABLE 2

EXPRESSION OF HUMAN NHE3 IN HUMAN ENDOTHELIAL CELL LINES

| | Visible Detection of Human NHE3 by PCR | |
|---|---|---|
| Total RNA Source | 1 PCR Round | 2 Nested PCR Rounds |
| Small Intestine | − | + |
| Human Melanoma | + | + |
| HPAEC | + | + |
| HMVEC | +/− (multiple bands) | + |

Thus, a variety of endothelial cell growth/shape related events are inhibited by squalamine and functionally related compounds. The experimental tests discussed below were conducted to assess this aminosterol's effects.

Growth Inhibition of Endothelial Cells, Fibroblasts and Epithelial Cells In Vitro:

When non-transformed human cells are grown in the presence of increasing concentrations of squalamine, endothelial cells exhibit a particular sensitivity to squalamine, as shown by the following experiment. Bovine pulmonary endothelial cells, human epithelial cell line MCF 10A, and human foreskin fibroblasts were incubated in the presence of 12 different membrane-active agents, including peptides and squalamine.

Specifically, bovine pulmonary endothelial cells, human epithelial cell line MCF 10A, and human foreskin fibroblasts were incubated in the presence of the following twelve membrane-active agents: (1) RGD[KIAGKIA]$_3$—NH$_2$; (2) d-[KKLLKKL]$_2$—NH$_2$; (3) squalamine; (4) SWLSK-TAKKLENSAKKRISEGIAIAIQGGPR; (5) FLGGLIKIV-PAMICAVTKKC; (6) Magainin 2; (7) PGLA; (8) GFAS-FLGKALKAALKIGANLLGGTPQQ; (9) PR-39; (10) l-[KKLLKKLI]$_2$—NH$_2$ (11) Cecropin B; and (12) [KIAGKIA]$_3$—NH$_2$. Cell growth was measured by absorbance at 600 nm. Results are shown in FIGS. 3A–3C.

Figure 3A:
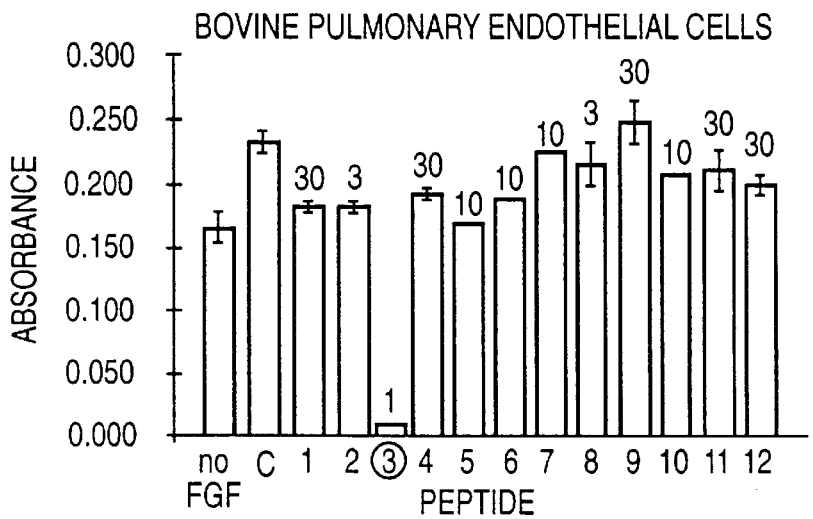
Figure 3B:
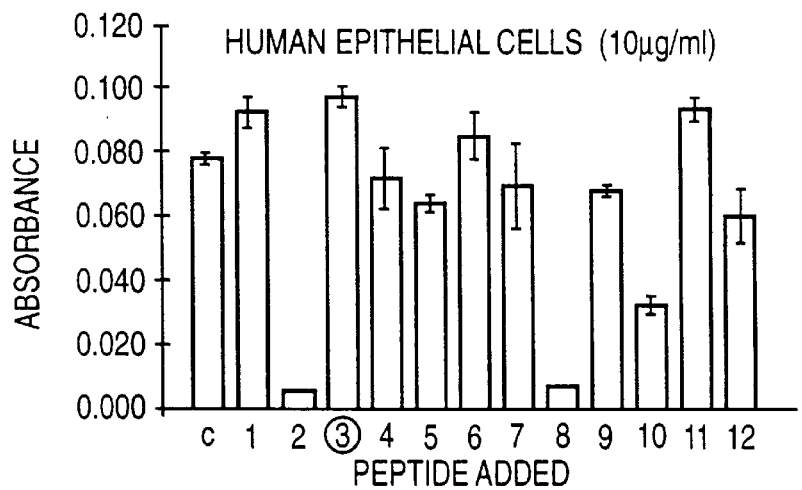
Figure 3C:
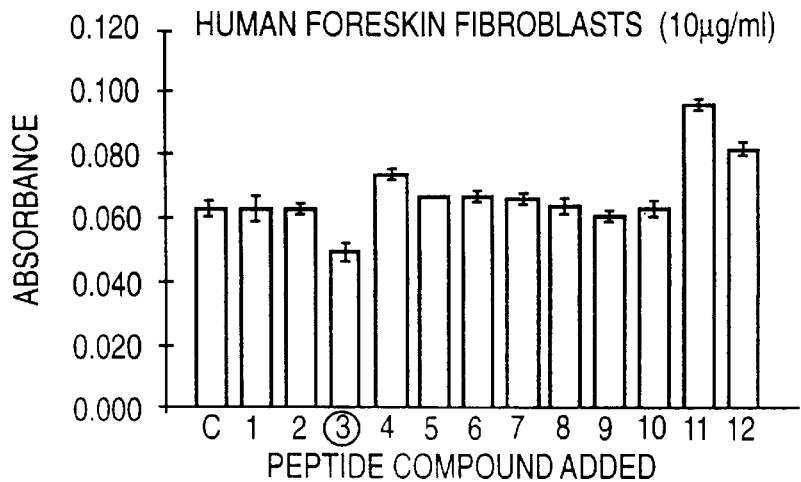

As evident from FIG. 3A, squalamine inhibited the growth of bovine pulmonary artery endothelial cells (BPE) at 1 μg/ml. In contrast, at 10 μg/ml it exerted no effect on the growth of either epithelial (FIG. 3B) or fibroblast (FIG. 3C) lines. However, peptides that inhibited the growth of epithelial cells exhibited no effect on BPE. Thus, endothelial cells are more sensitive to squalamine than are either fibroblasts or epithelial cells.

Inhibition of Endothelial Cell Cord Formation In Vitro:

Endothelial cells have the capacity in vitro to form tubular aggregates resembling capillaries in various early stages of formation. This conversion occurs under relatively specific conditions, in which essential growth factors along with an effective substratum are provided. It has been shown that both the interaction of growth factors with the endothelial cell and its attachment to a substratum activate the NHE. The activation of this exchanger is believed to be required for subsequent morphologic transformation of the endothelial cell into a multicellular tubular structure.

To assess the effect of compounds on the cord-like structures formed by human microvascular cells when plated in the presence of VEGF (Vascular Endothelial Growth Factor) and basic fibroblast growth factor on a collagen matrix, a standard cord formation assay was used. The results are shown in the table below.

TABLE 3

EFFECT OF VARIOUS AMINOSTEROLS ON ENDOTHELIAL CORD FORMATION

| | μg/ml | | | |
|---|---|---|---|---|
| | 0.01 | 0.1 | 1.0 | 10.0 |
| Fumagillin | | − | +/− | + |
| Squalamine | − | + | + | + |
| Compound 319 | − | + | + | + |
| Compound 353 | | + | + | + |
| Compound 410 | | − | + | +* |
| Compound 411 | | − | − | + |
| Compound 412 | | − | − | + |
| Compound 413 | | − | − | + |
| Compound 415 | | − | − | +/T |
| Compound 371 | | | T | T |
| Compound 432 | | | − | − |
| Compound 449 | | | − | +/− |
| Compound 467 | | | − | − |

Notes:
+ = Inhibition of angiogenesis;
− = No inhibition of angiogenesis;
T = Toxic;
* = cell rounding @ 10 μg/ml.

As shown in Table 3, squalamine inhibits cord formation at about 0.1 μg/ml, compared with fumagillin, which exhibits comparable activity at 10 μg/ml. At these concentrations, squalamine does not appear to profoundly affect cell viability or proliferation. This property in vitro roughly correlates with anti-angiogenic activity in more complex in vivo models (see Goto et al., *Lab Investigation* 69, 1993, 508–518).

LPS-Induced Neutrophil Adherence to Human Umbilical Venous Endothelial Cells:

When endothelial cells are exposed to certain stimuli, including lipopolysaccharide (LPS) and certain cytokines, specific adhesion molecules are induced on the plasma membrane that enhance the binding of leukocytes. These leukocyte-endothelial cell interactions are believed to be necessary to localize leukocytes to sites of bacterial invasion and to facilitate extravasation of the leukocytes from the capillary into the surrounding tissue space. Leukocyte-adhesion molecules include the Selectins and ICAM-1.

To determine if squalamine inhibited this particular endothelial cell function, standard adhesion assays were performed as outlined in Gamble et al., *J. Imm. Methods* 109, 1988, 175–184. The expression of cell surface ligands in an endothelial-based system has been shown to effect adherence to granulocytes with a system using human umbilical venous endothelial cells, purified neutrophils, and inducers of cell surface ligands such as LPS (100 ng/ml) and TNF-α (40 ng/ml). In these experiments, approximately 2×10$^5$ human umbilical venous cells (passage 2–6) were plated per well. The cells were grown in serum-free media overnight. For induction, either TNF-α (40 ng/ml) was added to endothelial cells for 6 hours prior to adding neutrophils or LPS (100 ng/ml) was added for 4–6 hours. It was found that the LPS response was increased by adding 1% FBS to the wells to provide a source of LPS-binding protein. After activation of the endothelial cells, approximately 50×10$^6$ neutrophils were added per well. The plates were gently rocked for 30 minutes at room temperature, followed by removal of the media and washing in serum-free media three times and then photographing of each well. Experiments to test the effects of squalamine were performed by adding squalamine at 10 μg, 1.0 μg, or 0.1 μg at the time of adding LPS or TNF-α. A second repeat dose of squalamine was added at the time of adding neutrophils. A monoclonal Ab to ICAM-1 was a positive control.

Using three different subjects, there was no inhibition of squalamine on neutrophil adherence using activated human endothelial cells. There was approximately 50% inhibition of adherence when adding 40 μg/ml of a monoclonal Ab to ICAM-1 prior to adding neutrophils.

These results indicate that inhibition of the endothelial NHE by squalamine affects both growth and capillary formation in vitro, but does not inhibit all signal transduction pathways in this cell. Thus, certain "housekeeping" functions, such as the capacity of the endothelial cell to attract leukocytes to the site of an infection, should not be impaired by squalamine. This demonstrates that squalamine can be used to inhibit angiogenesis but will not otherwise disrupt certain important endothelial cell functions, such as leukocyte recruitment to sites of infection or inflammation.

Anti-proliferative Activity:

The Chorioallantoic Membrane Model:

Using the classical chorioallantoic membrane model, it has been found that squalamine is an inhibitor of capillary growth. The growing capillaries within the chorioallantoic membrane model (CAM model) have been used as a system in which to evaluate the effect of agents on their potential to inhibit new vessel growth. Neovascularization occurs most aggressively over the first week of embryonic development. Thereafter capillary growth is characterized by principally "elongation" rather than "de novo" formation.

In the standard assay, agents are applied locally to a region of the embryo over which neovascularization will occur. Agents are assessed by their ability to inhibit this process, as evaluated by visual examination about 7 days after application. Agents which disrupt vascular growth during the period of de novo capillary formation, but do not interfere with subsequent capillary growth, are generally regarded as "specific" inhibitors of neovascularization, as distinguished from less specific toxic substances. The assay utilized is described in detail in Auerbach et al., *Pharm. Ther.* 51, 1991, 1–11. Results are tabulated below.

TABLE 4

INHIBITION OF CAPILLARY GROWTH IN CAM MODEL

| | Squalamine Applied (μg) | Percentage positive Assay 1 | Assay 2 | Mean |
|---|---|---|---|---|
| 3-Day Embryo: | 0.65 | 28 | | |
| | 1.25 | 18 | 18 | 18 |
| | 2.5 | 35 | 18 | 27 |
| | 5.0 | 91 | 57 | 74 |
| | 20 | 52* | 58* | 55 |
| | 40 | 50* | 13* | 32 |
| 13-Day Embryo: | 5.0 | | 0/26 | |

Note:
* = Some vascular irritation noted.

As seen from Table 4, applying as little as 0.65 μg squalamine to a 3-day CAM resulted in inhibition of CAM vessel neovascularization. In contrast, applying ten times that amount of squalamine onto a 13-day old chick exerted no inhibitory effect.

Thus, in a classical angiogenesis assay, squalamine exhibited potent but specific inhibitory activity, equal in potency to the most active compounds described to date in the literature. The effect is compatible with suppression of neovascularization rather than toxic inhibition of capillary growth.

The Vitelline Capillaries of 3–5 Day Chick Embryo Model:

In the course of evaluating squalamine in the "classical" chick chorioallantoic membrane model, it was noted that this steroid exerted a dramatic and rapid effect on capillary vessel integrity in the three- to five-day old chick embryo. Using the chick embryo vitelline capillaries assay, compounds were tested for their ability to induce capillary regression. Each compound was applied in 0.1 ml of 15% Ficol 400 and PBS onto the embryo, and vascular regression was assessed after 60 minutes.

Figure 8:
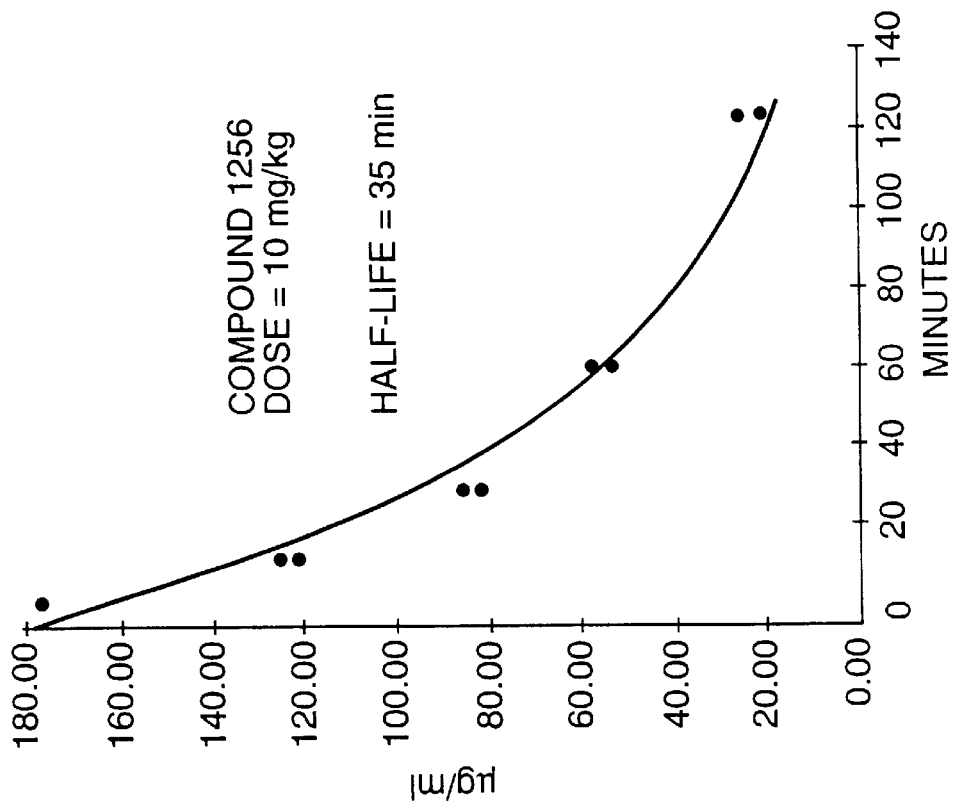
FIG. 8 shows the pharmacokinetic clearance of squalamine from a mouse IV PK study.

Squalamine was found to disrupt vitelline capillaries in 3- to 5-day chick embryos. The 3-day chick embryo consists of an embryonic disc from which numerous vessels emerge and return, forming a "figure 8"-shaped structure—the embryo in the center with vascular loops extending outward over both poles. Application of squalamine onto the embryonic structure (0.1 ml in 15% Ficol in PBS) resulted in progressive "beading up" of the vitelline vessels, with the finest capillaries being the first to exhibit these changes. Following a lag period of around 15 minutes, the constriction of continuity between capillary and secondary vessels, generally on the "venous" side, was observed. Continued pulsatile blood flow progressed, resulting in a "swelling" of the blind tube, followed by a pinching off of the remaining connection and formation of an enclosed vascular sac resembling a "blood island." This process progressed until only the largest vessels remained intact. The embryonic heart continued to beat vigorously. No hemorrhage was seen, reflecting the integrity of the capillary structure. In addition, no obvious disruption of circulating red cells was observed microscopically, demonstrating the absence of hemolysis.

Utilizing this assay, which appears to demonstrate what is commonly called capillary "regression," a minimum concentration of squalamine required to observe an effect in 60 minutes can be determined. Results are summarized in the table below.

TABLE 5

EFFECTS OF VARIOUS AMINOSTEROLS IN CHICK EMBRYO VITELLINE CAPILLARY REGRESSION ASSAY

| | Amount of Compound Applied (μg) | | | | |
|---|---|---|---|---|---|
| Compound | 10 | 1 | 0.1 | 0.01 | 0.001 |
| Compound 1436 | + | + | + | + | +/− |
| Compound 319 | + | + | + | + | +/− |
| squalamine | + | + | + | + | 0 |
| Compound 415 | | + | + | + | 0 |
| Compound 410 | | + | +/− | +/− | 0 |
| Compound 412 | | + | 0 | 0 | 0 |
| Compound 411 | | +/− | 0 | 0 | 0 |
| Compound 382 | + | + | 0 | 0 | 0 |
| Compound 1364 | + | + | 0 | 0 | 0 |
| Compound 371 | + | +/− | 0 | 0 | 0 |
| Compound 396 | | + | 0 | 0 | 0 |
| Compound 353 | +/− | | | | |
| Compound 413 | 0 | | | | |
| Compound 414 | 0 | | | | |
| Compound 381 | 0 | | | | |
| Compound 303 | 0 | | | | |
| Compound 318 | 0 | | | | |
| Compound 409 | 0 | | | | |

TABLE 5-continued

EFFECTS OF VARIOUS AMINOSTEROLS IN CHICK EMBRYO
VITELLINE CAPILLARY REGRESSION ASSAY

| Compound | Amount of Compound Applied ($\mu$g) | | | | |
|---|---|---|---|---|---|
|  | 10 | 1 | 0.1 | 0.01 | 0.001 |
| Compound 1360 |  | 0 |  |  |  |
| Vehicle | 0 | 0 | 0 | 0 | 0 |

Notes:
+ = Vascular reactivity;
0 = No vascular reactivity;
+/- = Equivocal reactivity;
Vehicle = 15% (w/w) Ficol in phosphate-buffered saline.

As apparent from Table 5, 0.1–0.01 $\mu$g of squalamine in 0.1 ml medium can induce changes. Compounds having various ranges of activities were found, with squalamine, compound 319 and compound 415 being especially active. This experiment demonstrates that the steroids tested can dramatically restructure capillaries over a time interval amounting to several minutes. The results reflect that squalamine exerts this effect through inhibition of NHE.

Tadpole Assay:

A newly developed assay employing tadpoles, preferably *Xenopus laevis* Stages 59–60, were employed to study the effect of a compound by monitoring capillary occlusion in the tadpole's tail. Animals at these stages were used because they represent the period of transition through metamorphosis at which time the animals possess both embryonic and adult stage tissues. The compounds of the invention affect the shape, viability and integrity of the embryonic tissues while not affecting the adult tissues, providing a powerful, highly specific screen. For example, substances that destroy all of the animal's epithelium, both adult and embryonic, could be regarded as toxic. Substances that destroy only the embryonic tissues exhibit a very unique specificity.

In this assay, tadpoles are introduced into Petri dishes containing a solution of the test compound in distilled water, preferably about 100 ml. The preferred concentration of the test compound is from about 1 $\mu$g/ml to about 10 $\mu$g/ml. The volume of liquid is sufficient for the animal to swim freely and drink from the solution. Thus, the effect observed results from oral absorption and subsequent systemic distribution of the agent. If the volume of liquid is not sufficient to permit oral intake, the effects that are observed would result from absorption through the surface epithelium. Thus, this simple assay can identify if an compound has characteristics of oral availability.

In another embodiment of this assay, a solution of a compound in water can be injected directly into the abdomen of the animal using standard techniques. Concentrations of the compound from about 0.05 mg/ml to about 0.5 mg/ml in about 0.05 ml of water are preferred.

After an amount of time, typically about 60 minutes, the occlusion of blood flow through capillaries in the tadpole's tail are observed under an inverted microscope at a magnification of roughly 100X.

When the tadpoles were introduced into distilled water containing squalamine at 10 $\mu$g/ml, it was observed that blood flow through the capillaries of the tail shut down. The process occurred from the caudal to cranial direction. Blood flow within the most distal vessels stopped initially, followed by the larger vessels. During this period, it was observed that the cardiovascular system was otherwise robust, as evidenced by a continued heartbeat, pulsatile expansion of the great vessels, and, most curiously, unaltered blood flow through the fine capillaries of the hands and feet. Thus, selective cessation of blood flow was seen in localized regions. If the animals are maintained in squalamine for several days, enhanced regression of the most distal aspects of the tail, as well as the peripheral aspects of the tail fin are observed, corresponding to regions of the animal perfused by the occluded vasculature.

This effect apparently results from selective change in the resting diameter of the capillaries of the tail. Inhibition of the endothelial cell NHE evidently leads to a change in shape of the cell making up the capillary, resulting in diminished flow. The continued functioning of capillary beds in the "adult" portions of the tadpole (the limbs) indicates that squalamine is selective for certain capillaries. From the results of the tadpole tail capillary occlusion assay, compound 319, squalamine and compound 1436 were found to induce a common vascular occlusive effect.

Suppression of Melanoma Growth:

Suppression of Growth of Melanomas in Mice by Oral and Parenteral Routes of Administration:

The growth of B16 melanoma in C57B mice is dependent upon neovascularization. Hence, this is a recognized model for evaluating the impact of inhibitors of angiogenesis on the growth of cancer.

Figure 4A:
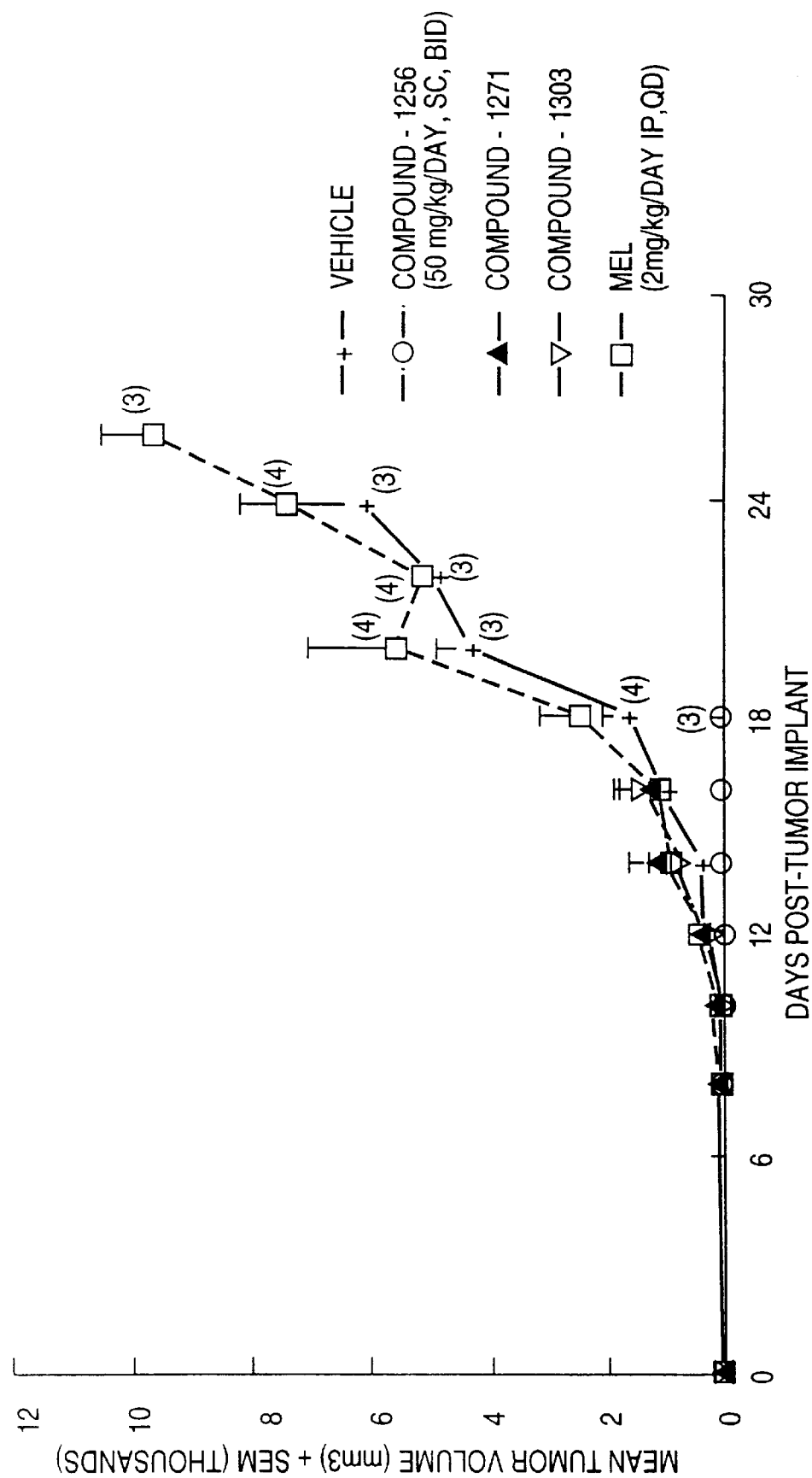
Figures 1, 4A:
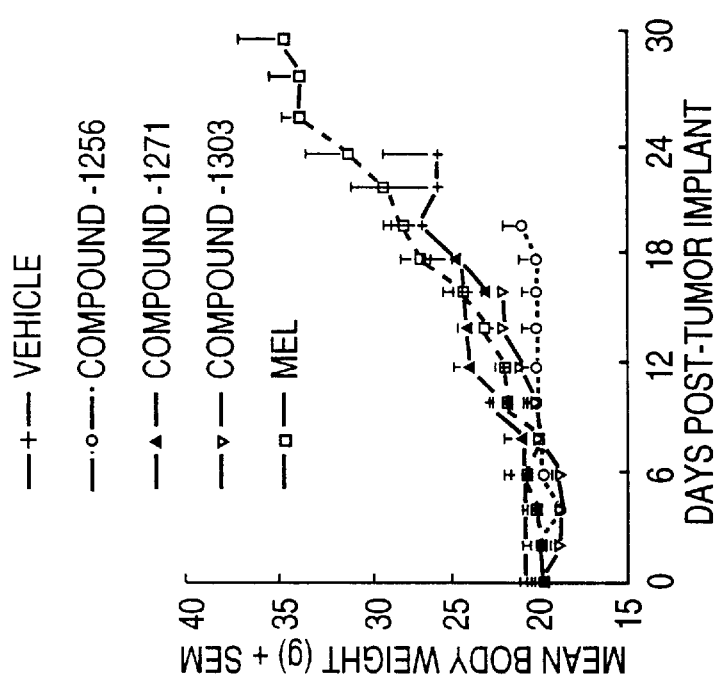
Figure 4B:
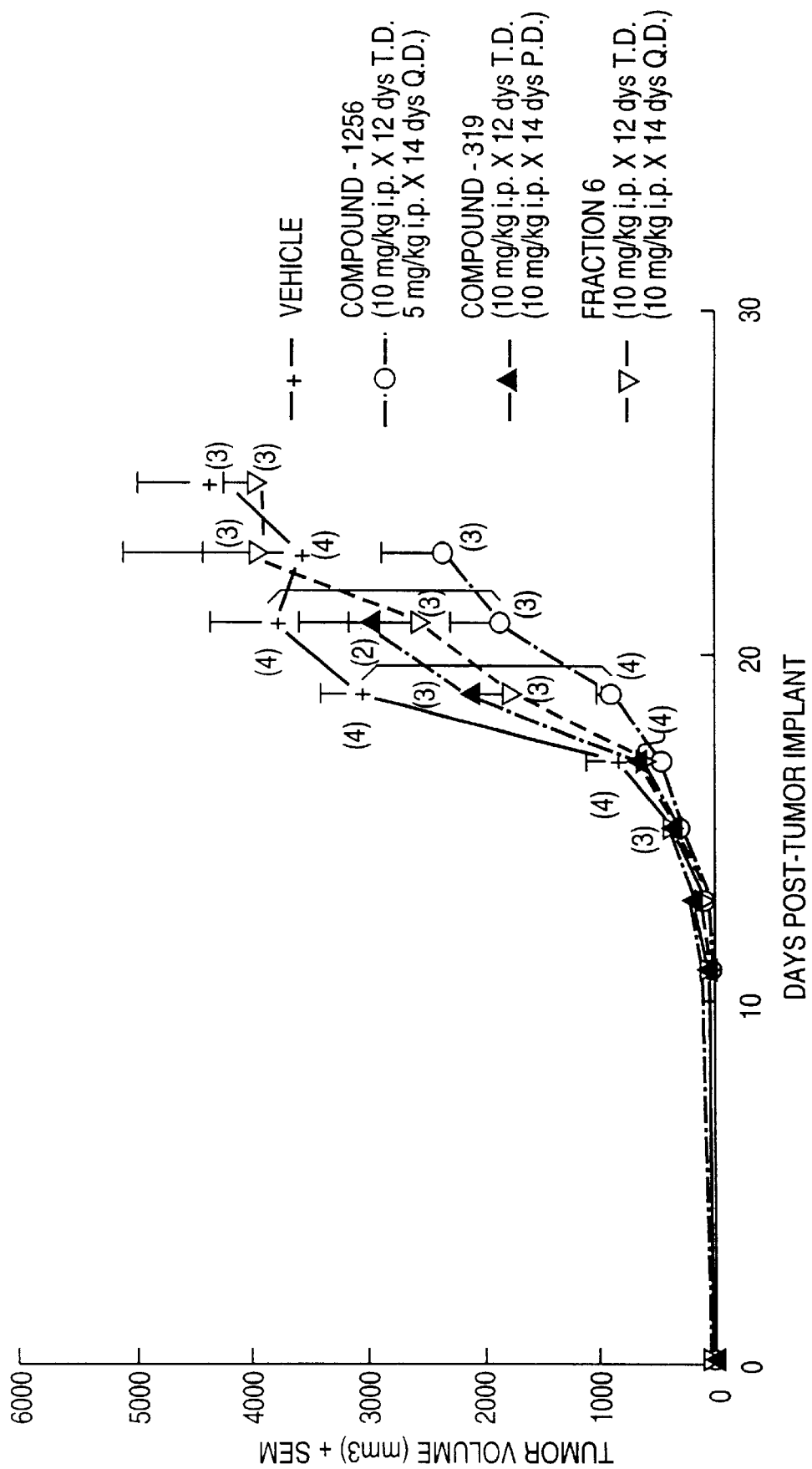
Figures 1, 4B:
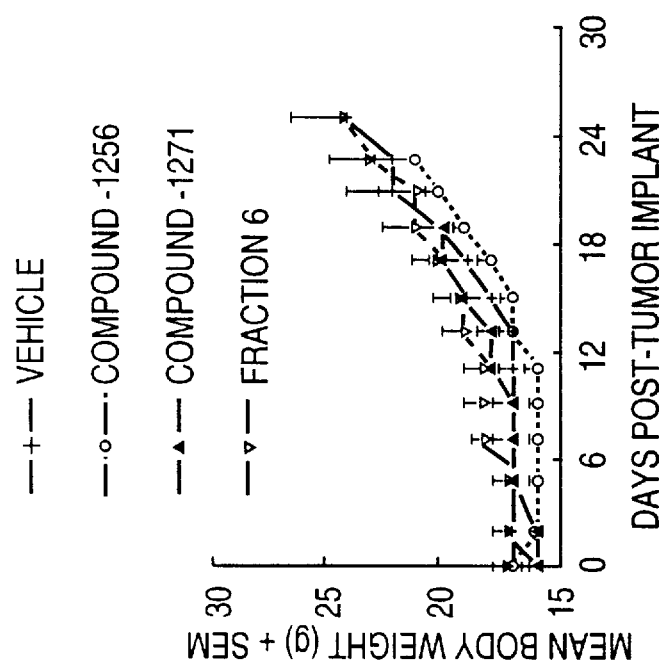
Figure 4C:
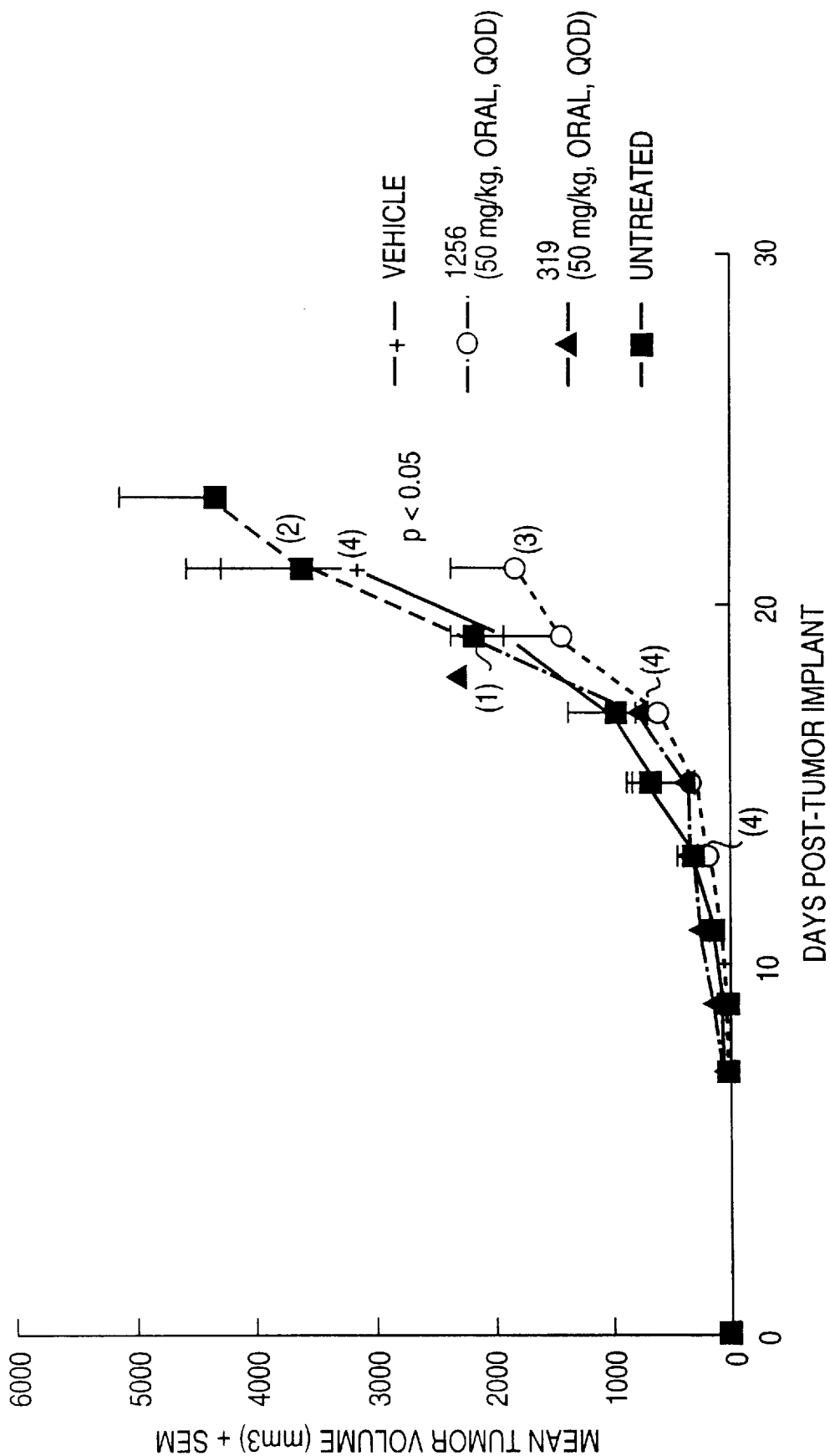
Figures 1, 4C:
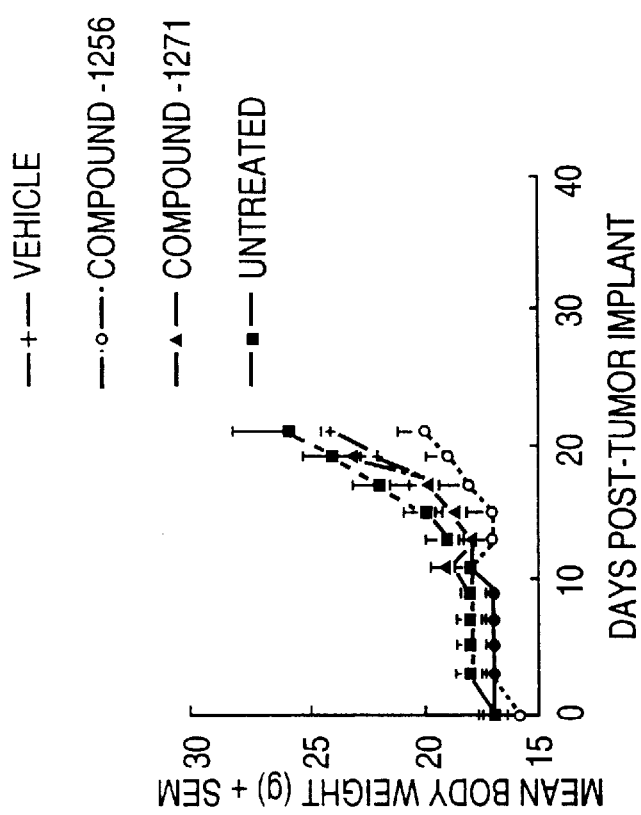

Using the growth of B16 melanoma cells in C57B mice, a recognized model for the evaluation of inhibitors of angiogenesis on the growth of cancers, the effects of subcutaneous, intraperitoneal and oral administration of squalamine were evaluated. An inoculum of B16 melanoma cells was implanted subcutaneously on the dorsum of the C57B mouse, which resulted in the progressive growth of melanoma lesions over 30–40 days as shown in FIGS. 4A, 4B, and 4C.

In this model, there was observed little evidence of metastasis. with or without treatment with chemotherapeutic agents. When animals were treated with squalamine either subcutaneously (FIGS. 4A-1), intraperitoneally (FIGS. 4B and 4B-1) or orally (FIGS. 4C and 4C-1), a dose-dependent suppression of tumor volume was observed. Measurement of both body weight and hematologic parameters demonstrated no significant depression. Since squalamine itself shows minimal cytostatic activity against B16 in culture, except at very high concentrations, this response of the tumor was interpreted to be secondary to interference with capillary development.

Figure 5:
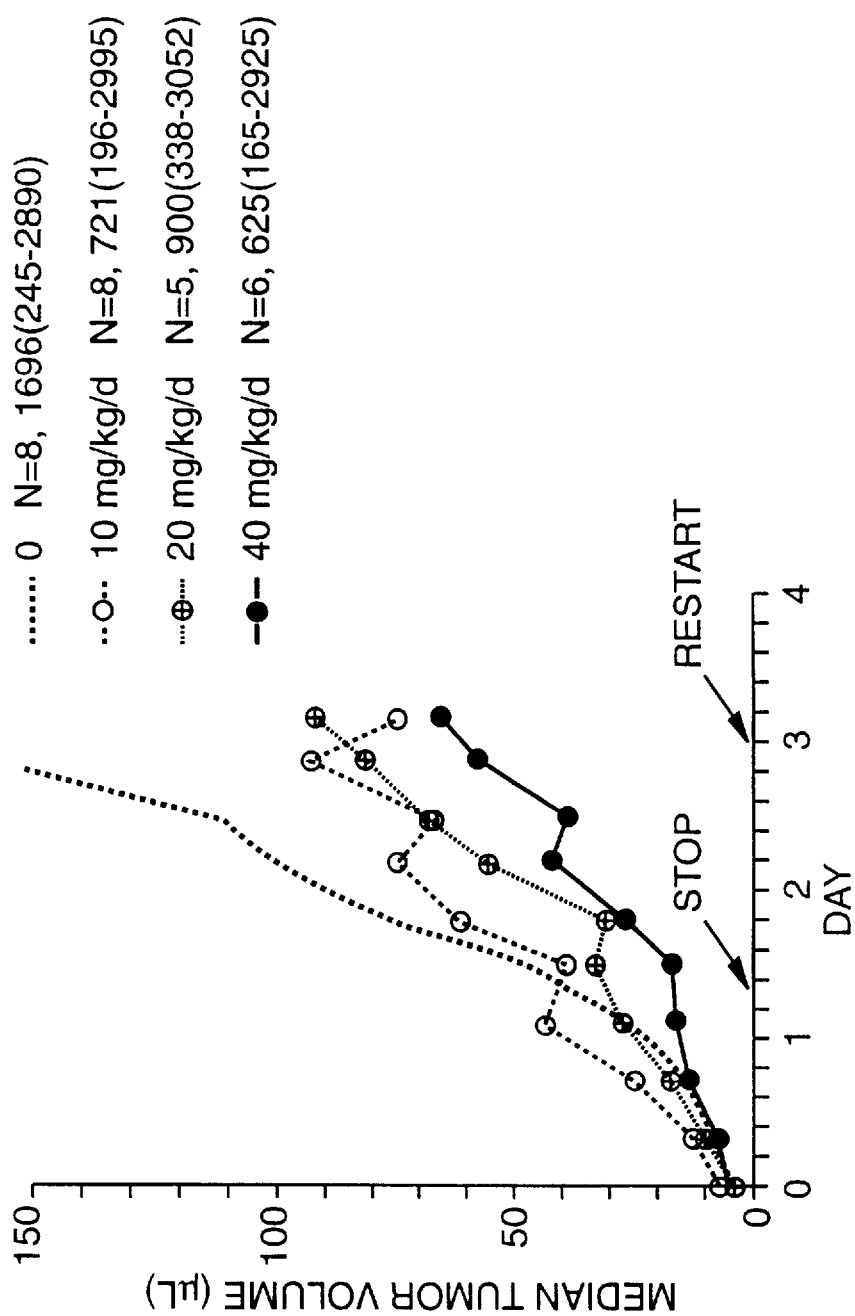

Suppression of Growth of Human Melanoma in Immunocompromised Mice:

As apparent from FIG. 5, melanoma 1205Lu develops aggressively in RAG-1 mice after implantation. Squalamine has been found to suppress the growth of melanoma 1205Lu in RAG-1 mice in a dose-dependent fashion.

Squalamine was administered after tumors had reached about 0.1 ml, and clear suppression of tumor growth in a dose-dependent fashion was found as evidenced by FIG. 5. After cessation of treatment, tumor growth continued at a rate similar to untreated controls, suggesting that the impact of squalamine in this setting is reversible.

Suppression of Tumor-Induced Corneal Neovascularization in Rabbits:

The implantation of VX2 carcinoma into the rabbit cornea results in the induction of new blood vessels within several days (Tamargo et al., *Cancer Research* 51, 1991, 672–675). It is believed that this carcinoma secretes growth factors that stimulate new blood-vessel growth. Thus, this model is indicative in vivo evidence of therapeutic utility in the treatment of pathological disorders of vascularization, including the metastatic spread of tumors, diabetic retinopathy, macular degeneration, and rheumatoid arthritis.

This experiment followed the published protocol—tumor was implanted adjacent to a polymer containing a concentration of the agent to be evaluated. The polymer releases the agent slowly in the immediate neighborhood of the tumor, providing sustained high local concentrations of the agent. In this experiment, squalamine introduced into a pellet of ELVAX 40 P (DuPont, Wilmington, Del.) inhibited new blood vessel formation by about 60% at days 7 and 14, and by about 25% at day 21.

As demonstrated by the experiments described above, squalamine provides a potent inhibitor of NHE3. Squalamine therefore should provide invaluable therapeutic intervention wherever new blood vessel formation in vivo is implicated.

Indeed, any pathological processes dependent on new blood vessel formation can be treated through inhibition of NHE3. As an agent that interferes with the process of neovascularization, squalamine has therapeutic utility in the treatment of diseases or disorders dependent on continued neovascularization where interruption of neovascularization diminishes the intensity of the pathological process. Thus, squalamine has utility for treating disorders including solid tumor growth and metastasis, rheumatoid arthritis, psoriasis, diabetic retinopathy, macular degeneration, neovascular glaucoma, papilloma, retrolental fibroplasia, and organ rejection.

Moreover, other aminosterols have shown anti-angiogenic activity. Compounds were subjected to a various assays, including the chick embryo capillary regression assay, the tadpole assay, the assay for inhibition of endothelial cord formation, and the assay for direct inhibition of NHE, as described above, to determine their utilities. As evident from the above data, correlation among the results from the chick, tadpole and in vitro inhibition of endothelial cell cord formation assays is excellent.

Through the application of these assays, compound 319 emerged as an attractive alternative to squalamine. In fact, it has been found to be superior to squalamine in the following characteristics: potency as an NHE inhibitor; simpler synthetic route; specificity—i.e, no CNS effects. Further properties of compound 319 are discussed below.

Figure 6:
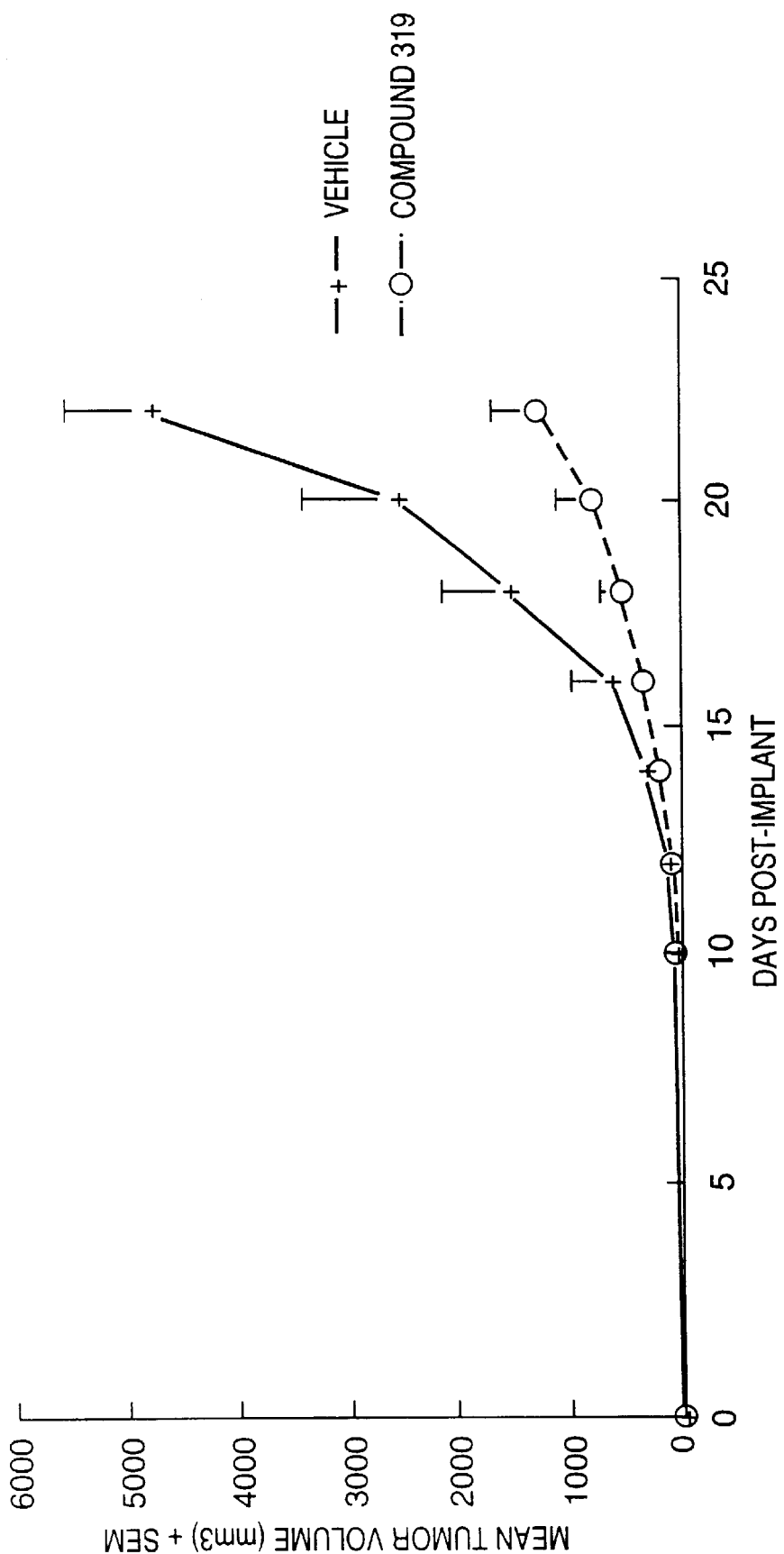
FIG. 6 illustrates the suppression of murine melanoma in mice by intraperitoneal administration of compound 319.

Melanoma Growth Suppression:

Compound 319 has been found to exhibit activity against B16 melanoma in vivo. As seen in FIG. 6, which illustrates the results from the murine melanoma assay described above, subcutaneous administration of the compound achieved control of B16 in C57B mice to an extent almost comparable to squalamine (FIG. 4B).

Figure 7:
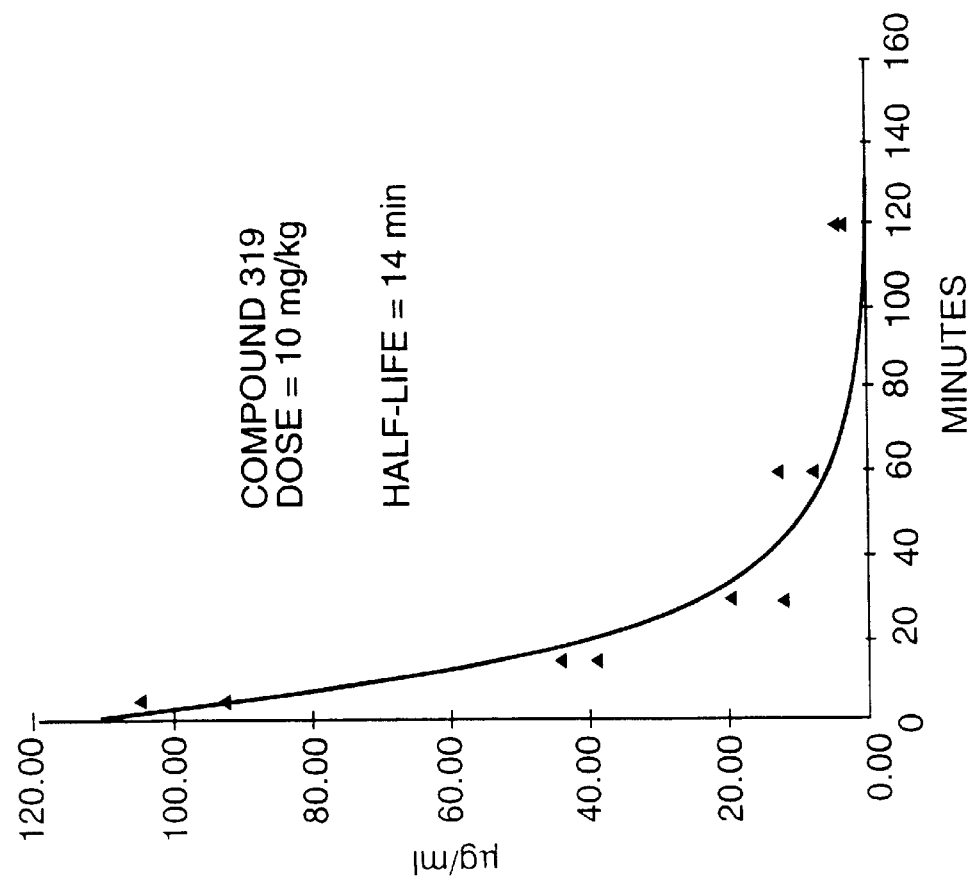
FIG. 7 shows the pharmacokinetic clearance of compound 319 from a IV PK mouse study.

Pharmakokinetic Clearance:

Compound 319 also has a more rapid pharmacokinetic clearance than squalamine. To assess clearance, a mouse IV PK study was performed for compound 319 and squalamine. The compound was administered i.v. and blood samples were taken every 10 minutes. The concentration of the administered steroid was determined by HPLC analysis. As shown in FIG. 7, after i.v. administration, the compound was cleared from the blood stream of the mouse with a half-life of about 14 minutes. In comparison, squalamine was cleared with about a 35-minute half-life, as reflected by FIG. 8.

It should be possible to achieve further reductions in clearance in vivo through derivatives of compound 319. It is frequently of value to extend the lifetime of an agent in the bloodstream, to achieve higher blood levels with a given dose of drug and to reduce the frequency of administration. Polyamines are readily metabolized by a variety of oxidases, which degrade the free terminal amino group of the polyamine moiety. See Seller et al., Prog. Drug. Res. 43, 1994, 88–126. Alkylation of the primary amine generally retards this metabolic pathway. Seller et al., id. Thus, through simple alkylation of the primary amine on compound 319 or on any of the steroids bearing a metabolizable polyamine, straightforward modifications of this type would be expected to extend biological lifetime.

Xenopus Tadpole Assay:

The tadpole assay described above provides an advantageous way to determine the pharmacological targets of each steroid when introduced into a mammal, and to determine pharmacological categories into which synthetic compounds belong. In the assay, each of the steroids was dissolved in 100 ml of distilled water at a concentration of 10 $\mu$g/ml. Stage 59–60 Xenopus tadpoles were introduced and evaluated by light microscopy and gross observation 1 hour later.

The steroids tested were observed as producing different and distinctive pharmacological responses in this animal:

Compound 1256 (Squalamine): Vascular occlusion in fine capillaries of tail. No effect on vascular flow through hands or feet. Inactivity and death occurred within 2 hours.

FX1: Increased passage of fecal material within 1 hour. By 12 hours, solution contained considerable fecal debris.

Circulatory system of animal appeared hyperemic, suggestive of hematopathic stimulation.

Compound 1360: Swelling and lysis of certain erythrocytes occurred, resulting in accumulation of nuclei within certain small vessels of the tail. Subsequent tissue breakdown occurred in areas of tail surrounding these nuclear plugs.

Compound 1361: Similar to compound 1360.

Compound 1436: Gradual reduction in overall activity. Heart beat remained strong, suggesting nervous system depression. Melanocytes over head and tail began to swell, first exhibiting visibly distinct nuclei, followed by rupture into fragments. Animal died by about 2 hours.

Compound 1437: Epithelium covering the embryonic portions of the animal, such as the tail and antennae, began to slough off in sheets. Sheets of cells remain intact initially, but gradually detach from one another. Trypan Blue staining demonstrates that cell death occurred. Animal was otherwise active, with little tissue breakdown noted.

FX 3: Muscular bundle within the tail began to leak myoglobin. Striations of the skeletal muscle grew less distinct. Segments of muscle began to separate.

Inhibition of Mitogen-Stimulated Growth of Human T-cells:

Specific assays were used to identify steroids with a particular biological activity, such as an assay for inhibition of mitogen-stimulated growth of human T-cells. Mitogen-induced cell proliferation has been reported to be dependent on the activation of the NHE. Thus, to determine which steroids act on particular cells, one need only determine which steroids inhibit mitogen- (or growth factor)-activated cellular proliferation.

The T lymphocyte is the lymphoid cell which serves as the host of HIV infection. A steroid that inhibits transformation of human lymphocytes is, in principle, acting on an NHE probably activated during HIV infection. Indeed, since GP120 activates hippocampal cell NHE upon binding to its cellular receptor (Benos et al., J. Biol. Chem. 269, 1954, 13811–13816), the assumption that a similar event follows early viral interaction with the lymphocyte is reasonable. This formed the basis of the next assay.

Human heparinized blood, freshly collected, was introduced into tissue culture flasks containing 10 μg/ml phytohaemagglutinin (PHA) in RPMI medium with 10% FCS. Various purified steroids were introduced subsequently at concentrations of 1, 5, and 10 μg/ml. Cultures were incubated for 72 hours, after which time colcemid was added to 1 μg/ml. Cultures were maintained for an additional 2 hours, and cells collected. Mitotic figures were estimated using standard cytochemical techniques, following Giemsa staining. Results are tabulated below.

TABLE 6

INHIBITION OF PHA-STIMULATED HUMAN LYMPHOCYTES

| Compound | (% control) | | |
|---|---|---|---|
| | 1 μg/ml | 5 μg/ml | 10 μg/ml |
| 1256 | 3 | 8 | 10 |
| 1360 | 5 | 5 | 5 |
| 1436 | 20 | 50 | 80 |
| 1437 | | | 10 |
| FX 3 | | | 5 |

As seen from the above table, compound 1436 inhibited blast transformation most potently, with greater than 75% inhibition observed at 10 μg/ml. Some effect was observed for squalamine at this concentration, but the other steroids were considerably less active. By using this simple assay, compound 1436 was identified for use in the treatment of T-cell lympho-proliferative diseases, including viral infections which actively propagate on these cells.

Assays of similar design, employing a cell of interest and an appropriate growth factor, can be readily constructed. Thus, to determine which steroid might be most useful in inhibiting proliferation of vascular smooth muscle cells following angioplasty, one need only set up a culture with human coronary smooth muscle and determine which steroid inhibits the PDGF-stimulated growth of these cells, as discussed below.

The Inhibition of a Spectrum of Cells:

Using the assay of Baker et al., Cancer Res. 53, 1993, 3052–3057, compound 1436 was observed to inhibit the growth of a very broad spectrum of cells. As set forth in Table 7 below, all malignant tumors evaluated in tissue culture, endothelial cells and vascular smooth muscle cells were sensitive to inhibition. Thus, compound 1436 has application in the control of growth factor dependent proliferation of many types of tissue.

TABLE 7

CANCER CELLS INHIBITED IN VITRO BY COMPOUND 1436 (10 μg/ml):

| | |
|---|---|
| Human colon carcinoma | SW948 |
| Human colon carcinoma | HT29 |
| Human ovarian carcinoma | SKOV3 |
| Human melanoma | WM 1617 |
| Lewis lung carcinoma | |
| Murine B16 melanoma | |
| Murine L1210 leukemia | |

Figure 10:
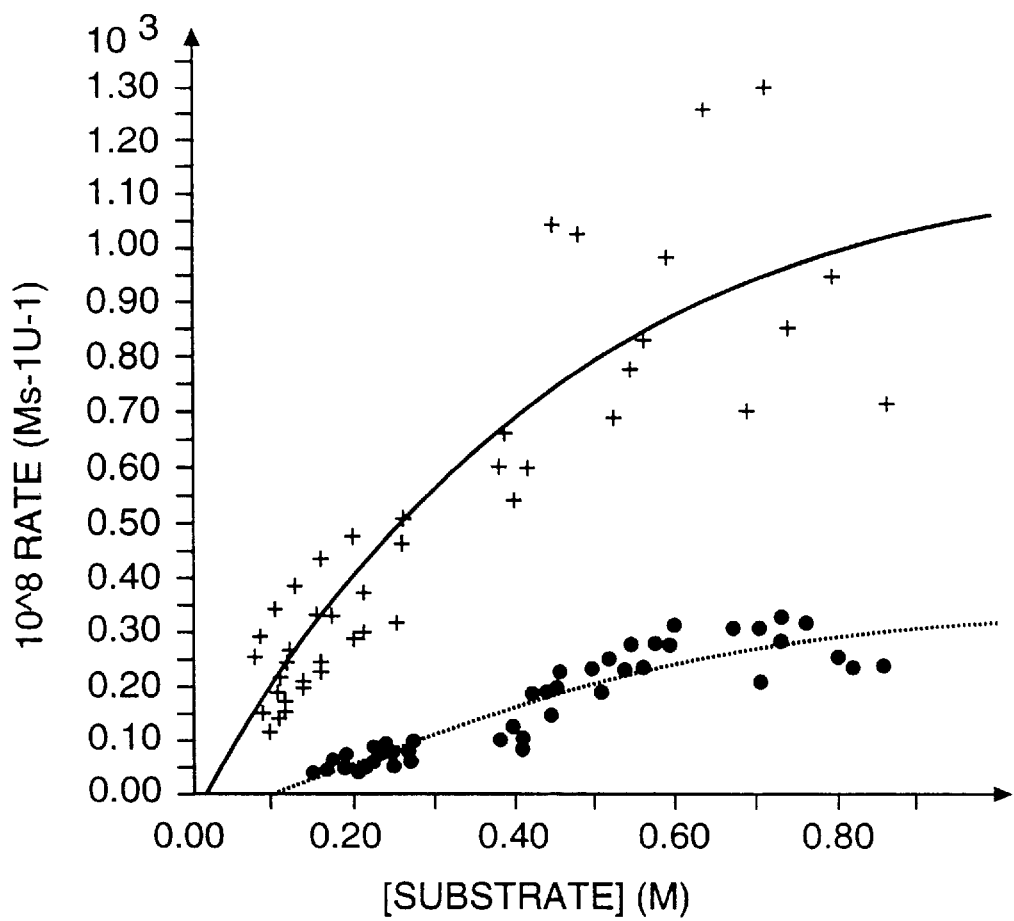
FIG. 10 illustrates the inhibitory effect of compound 1436 on NHE3.

NON-TRANSFORMED CELLS INHIBITED IN VITRO BY COMPOUND 1436 (10 μg/ml):

Bovine pulmonary endothelial cells
Human microvascular endothelial cells
Human umbilical venous endothelial cells
Human coronary artery smooth muscle cells Inhibition of NHE3:

Compound 1436 was also found to inhibit rabbit NHE3. PS120 fibroblasts transfected with rabbit NHE3 were grown and acid preloaded by exposure to 40 mM $NH_4Cl$ as described above in conjunction with FIGS. 1A and 1B. Internal cellular pH changes expressed as the rate of pH recovery as a function of restored extracellular sodium ion concentration following exposure to 10 μg/ml of the compound were assayed with the fluorescent dye BCECF-AM as described above. The results are presented in FIG. 10.

Thus, compound 1436 is an inhibitor of NHE3. The inhibition of NHE3 caused by compound 1436, however, does not adequately explain the very different pharmacologic effects of squalamine and compound 1436 when assessed on cells in culture and several in vivo models, as described above. This suggested that compound 1436 was inhibiting another NHE in addition to NHE3. A reasonable candidate NHE is NHE5 (recently cloned, see Klanke et al., Genomics 25, 1995, 615–622), which is expressed at least in lymphoid cells, brain, and testes.

Inhibition of NHE5-Expressing Cells:

To determine whether NHE5 was the other NHE affected by compound 1436, a test was performed to evaluate whether cells inhibited by this compound expressed NHE5. Using the method of Klanke et al. and appropriate PCR primers as described in Klanke et al., it was found that NHE5 was expressed in all cell types which exhibit sensitivity to compound 1436 (see table below). Total cDNA was prepared from isolated total RNA or total RNA or polyA+ RNA purchased from Clontech Laboratories (Palo Alto, Calif.). Initial PCR cycle reactions were carried out as described in conjunction with Table 2 above, with primers specific for human NHE1, human NHE3 or human NHE5 with 80 ng cDNA or, in the case of polyA$^+$ RNA as the cDNA source, with 1.5 ng cDNA. The annealing temperatures were 57° C. in all instances. Hemi-nested PCR reactions were then carried out for human NHE1 and NHE5 and nested PCR reactions for human NHE3 in second-cycle PCR reactions, with the conditions as described above in conjunction with Table 2, except that the annealing temperature for the second PCR round for the primers to detect NHE5 was 65° C. Results are tabulated below.

TABLE 8

| Antiporter: | NHE1 | | NHE3 | | NHE5 | |
|---|---|---|---|---|---|---|
| Rounds of PCR: | 1 | 2 | 1 | 2 | 1 | 2 |
| Assayed cell line or tissue | | | | | | |
| adrenal gland | + | + | − | + | + | + |
| brain, whole | + | + | +* | + | + | + |
| small intestine | − | + | − | + | | |
| skeletal muscle | + | + | − | −/+* | − | + |
| HPAEC (endothelial) | + | + | +* | + | + | + |
| HMVEC (endothelial) | + | + | − | + | + | + |
| $CaCO_2$ (epithelial) | + | + | +* | + | + | + |
| melanoma (WM1617) | + | + | +* | + | + | + |
| colon carcinoma (polyA$^+$ RNA) | + | + | +* | + | − | − |
| leukemia HL-60 | + | + | − | + | − | + |
| leukemia MOLT4 (polyA$^+$ RNA) | + | + | − | + | − | + |
| astrocytoma | + | | + | | + | |
| glioblastoma | + | | + | | + | |

Note:
* = multiple PCR bands observed.

It is believed that NHE5, which is similar in sequence to NHE3, is the more effectively inhibited target of compound 1436. Cells which exhibit both NHE3 and NHE5 would experience both NHE isoforms shut down by compound 1436, but only NHE3 would be inhibited in the presence of squalamine.

Figure 11:
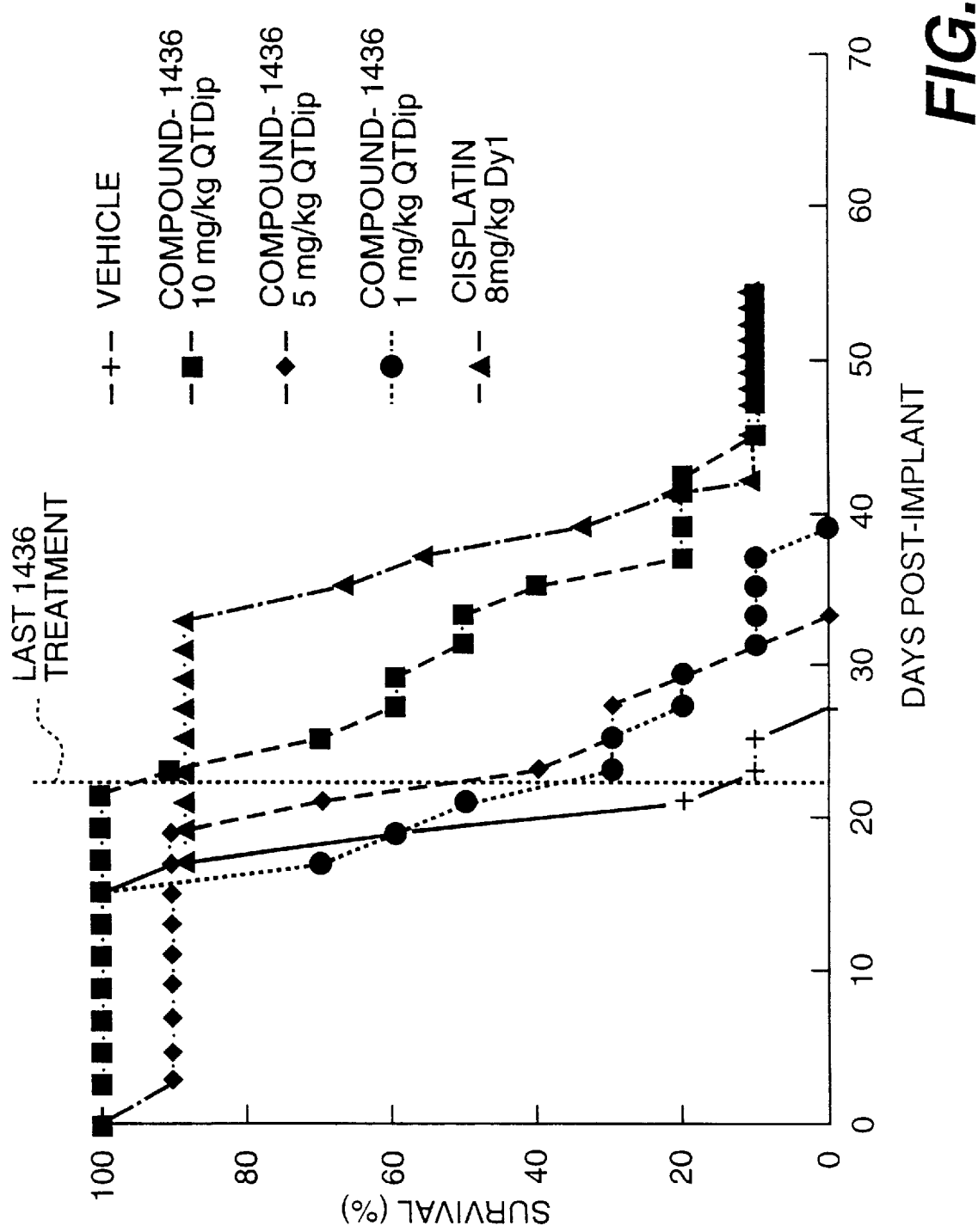
FIG. 11 illustrates the effect of compound 1436 on survival in mice bearing L1210 leukemia.

Inhibition of Mouse Leukemia:

Because of its inhibitory activity on the growth of numerous cancer cells, compound 1436 was evaluated in a classical mouse model of leukemia (Baker et al., *Cancer Res.* 53, 1993, 3052–3057). C57B mice were inoculated with L1210 lymphoblastic leukemia cells at an inoculum that causes leukemia in 100% of animals. Mice received compound 1436 at 1, 5, 10 mg/kg every 3 days intraperitoneally. As shown in FIG. 11, significant prolongation of life was achieved with the highest dose of compound 1436.

Of particular interest is the hematological profile determined during the course of treatment. Animals were treated with cisplatin and compound 1436. As apparent from Table 9 below, animals treated with cisplatin developed a profound anemia by day 28, due to a suppression of marrow erythroid precursors. In contrast, animals treated with compound 1436 exhibited a near normal hematocrit, with evidence of a robust granulocyte count.

TABLE 9

| Agent | Treatment | RBC ($10^6$/mm$^3$) | | WBC ($10^3$/mm$^3$) | |
|---|---|---|---|---|---|
| | | Early Time | Late Time | Early Time | Late Time |
| Cisplatin | Inoculate mice 5 × 10$^5$ L1210 cells ip, d 1 inject cisplatin 8 mg/kg ip | 9.4 | 1.5 | 8.1 | 18.1 |
| Cmpd. 1436 | Inoculate mice 5 × 10$^5$ L1210 cells ip, inject compound 1436 10 mg/kg ip q4d | 4.8 | 8.8 | 3.3 | 3.7 |

Synergistic Inhibition of Tumor Growth:

Based on the idea that tumor growth involves both the clonal expansion of a malignant cell along with the development of a supporting vascular supply, a combination of compound 1436 with squalamine was tested to determine whether it would achieve a synergistic effect on solid tumor growth. This concept was evaluated in the B16 melanoma model.

Figure 12:
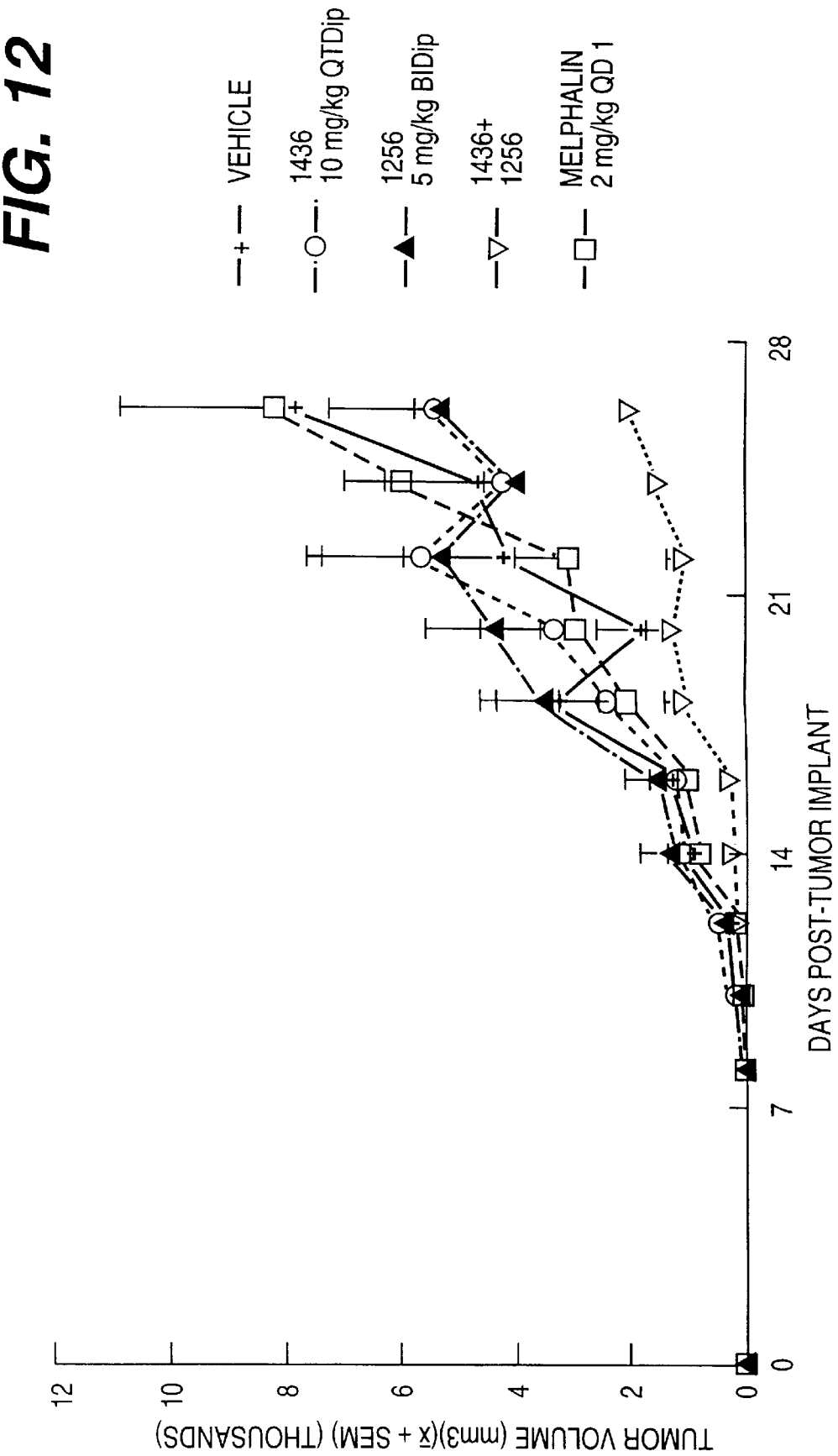
FIG. 12 illustrates that squalamine and compound 1436 exhibit synergy in suppressing growth of murine melanoma in mice.

Animals were implanted with B16 melanoma followed by treatment with compound 1436 or 1256 administered in a combined schedule or separately. As apparent from FIG. 12, when squalamine was administered at 5 mg/kg/day or compound 1436 was administered at 10 mg/kg/every 3 days, no significant impact on tumor volume was observed. In contrast, when both agents were administered together, a significant reduction in tumor growth was noted. Neither administration of squalamine at 15 mg/kg/day nor compound 1436 alone in a tolerable schedule could achieve this effect. Thus, a combination of these two compounds achieves a therapeutic benefit in tumors dependent on neovascularization that may prevent metastatic spread.

Effect of Aminosterols on Lymphotropic Viruses:

Since compound 1436 inhibits the PHA-stimulated proliferation of human T cells and controls the proliferation of a lymphoblastic leukemia in mice without unfavorable toxicity as shown above, it seemed a reasonable candidate for evaluation in vitro as an inhibitor of HIV. PHA-stimulated lymphocytes were inoculated with a clinical isolate of HIV at a multiplicity of infection of 10. Fresh lymphocytes were obtained and stimulated with PHA and IL-2. After 3 days, 1000 TCID of virus-(HIV clinical isolate) were applied for 1 hour and there was a M.O.I. of 1:10. The cells were washed and in a dose response fashion, and drug in media was applied. After 3 days, the supernatant was exchanged with ½ volume of fresh media and ½ the volume of fresh drug. After 7 days, detergent was added, and HIV P-24 Antigen was determined by Elisa. Viability of the lymphocytes was evaluated along with appearance of the viral gene product p24. Results are tabulated below.

TABLE 10

INHIBITION OF HIV REPLICATION BY COMPOUND 1436

| Conc. $\mu$M | P-24 Elisa | % Viability |
|---|---|---|
| 0.5 | 40561 | 91 |
| 1 | 7464 | — |
| 5 | 3426 | — |
| 10 | 421 | 95 |
| 20 | 9 | 90.1 |

As seen above, at 10 $\mu$g/ml compound 1436 effectively inhibited antigen synthesis by 97%, while retaining lymphocyte viability to 95%.

The above experiments clearly support the utility of compound 1436 in the treatment of lymphotropic viral diseases. Based on these studies, the identification of the specific NHE inhibitors of specific cellular targets of specific virus should permit the rational development of an effective antiviral therapy for a given infectious agent. Thus, the NHE inhibitor from the aminosterols that acts on the respiratory epithelial cell should be effective in the treatment of respiratory viruses which propagate on these cells, such as Herpes, influenza and RSV. The concept can be generalized to viruses infecting the CNS (herpes) and liver (hepatitis). The approach prevents infection by the virus of the cellular target by preventing activation of the cellular NHE, required for cellular proliferation and effective intracellular viral multiplication.

Effect on Insulin Secretion:

In studying additional roles for the aminosterols of this invention, it was noted that the release of insulin from the islet cell of the pancreas requires activation of the islet cell's NHE, ultimately activated through a mechanism triggered by glucose. It is believed that overstimulation of the islet cell might play a role in the depletion of islet cell function in Type II disease. In addition, suggestions have been presented that genetic mechanisms leading to hyperactivity of the islet cell NHE may play a role in Type I disease.

Thus, the onset of diabetes in individuals genetically susceptible, or placed into conditions of risk through acquired processes (obesity), might be delayed or allayed if islet cell function could be dampened. Inhibition of the NHE responsible for secretion of insulin could provide therapeutic benefit in these settings.

To study the effect of steroid administrator or the NHE responsible for secretion of insulin, several of the aminosterols from shark liver were administered to fasting mice. Male CD-1 mice were assigned to one of four treatment groups. Whole blood glucose was tested using glucometer (Lifescan Glucometer II and One Touch test strips). Statistical analysis was via one-way analysis of variance (ANOVA) followed by subsequent Bonferonni's t-test. Results are tabulated below.

TABLE 11

EFFECT OF COMPOUND ON FASTING BLOOD GLUCOSE IN MICE

| Group | n | Compound | Total Dose mg/kg | Treatment | Fasting Blood Glucose Mean + SEM (mg/dl) |
|---|---|---|---|---|---|
| 1 | 5 | — | — | Overnight fast, blood obtained | 38 ± 5.2 |
| 2 | 4 | 1437 (in H$_2$O) | 20 | 10 mg/kg i.v. Dy 0 PM, overnight fast, 10 mg/kg iv. Dy 1 AM, blood obtained 30 min. after 2d dose | 82 ± 15.3 |
| 3 | 4 | 1256 (in H$_2$O) | 20 | 10 mg/kg i.v. Dy 0 PM, overnight fast, 10 mg/kg iv. Dy 1 AM, blood obtained 30 min. after 2d dose | 65 ± 7.3 |
| 4 | 3 | 1436 (in D5W) | 20 | 10 mg/kg i.v. Dy 0 PM, overnight fast, 10 mg/kg iv. Dy 1 AM, blood obtained 30 min. after 2d dose | 105 ± 8.0 |

As apparent from the data above, blood glucose levels were elevated between 2–3 fold normal after administration of these steroids. The fasting blood glucose of Group 2 was significantly elevated compared to Group 1 (p<0.05). The fasting blood glucose of Group 4 was significantly elevated compared to Group 1. Thus, it appears that the intravenous administration of compound 1436 in D5W (5k glucose) or compound 1437 in water caused hyperglycemia in mice. It is assumed that the observed hyperglycemic response results from inhibition of insulin secretion, as suggested from basic physiological principles. Thus, the long-term chronic administration of a compound such as compound 1436 may be of value in preventing or delaying the onset of both Type I and Type II diabetes.

Figure 14:
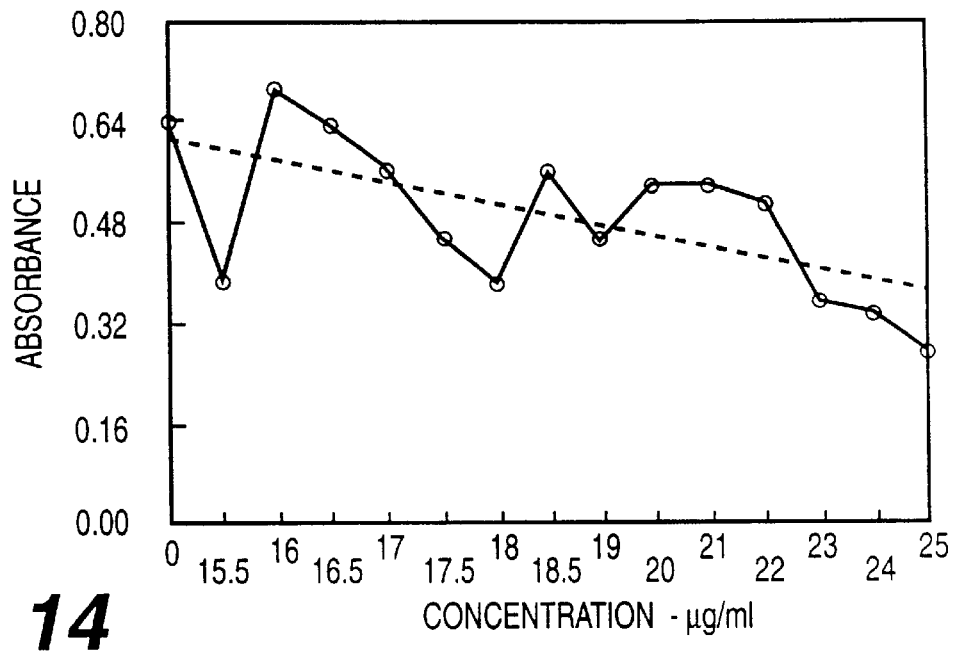
Figure 15:
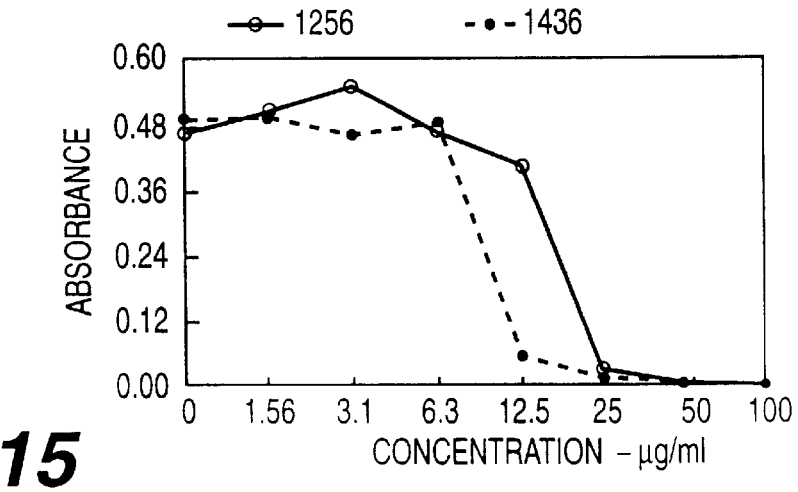
FIG. 15 is a expanded plot of the data shown in FIGS. 13A and 14, evidencing that both compound 1436 and squalamine suppress in vitro the growth of human coronary artery smooth muscle.

Effect on Growth of Arterial Smooth Muscle:

Aminosterols of the invention may also have utility in inhibiting the growth factor mediated proliferation of smooth muscle within the artery. Following coronary angioplasty, reocclusion commonly occurs, secondary to reparative proliferation of the vascular smooth muscle within the wall of the surgically manipulated blood vessel. This process generally takes place over the course of 7–10 days. To evaluate whether an agent could prevent the growth factor mediated proliferation of smooth muscle within the artery, compound 1436 was evaluated in vitro for its effect on the proliferation of human coronary artery smooth muscle. Results for compound 1436 are shown in FIG. 13, and those for squalamine are shown in FIG. 14, with FIG. 15 being a composite logarithmic plot.

Figure 13:
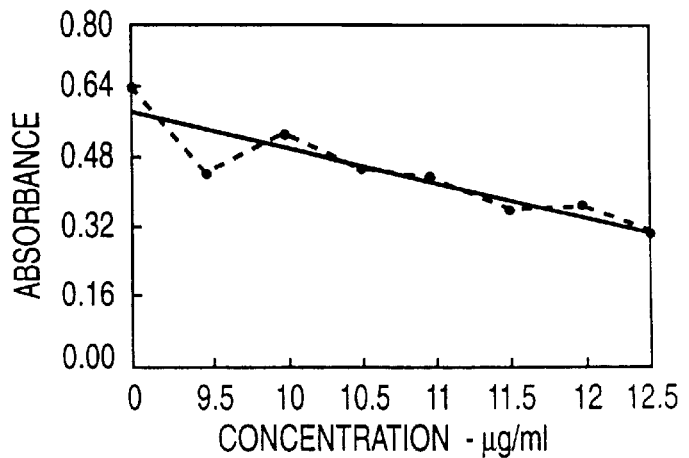
FIGS. 13 and 14 show the in vitro suppression of the growth of human coronary artery smooth muscle by compound 1436 (FIG. 13) and squalamine (FIG. 14), with absorbance plotted vs. concentration $\mu$g/ml.

As seen from FIG. 13, at about 10–12 μg/ml compound 1436 was effective in suppressing growth of these cells. For example, cells could be maintained in a quiescent state in the presence of this steroid at about 11 μg/ml without loss of viability. This experiment suggests that, for several days following angioplasty, local administration of compound 1436 to the site of angioplasty via slow-release administration in a proximal vascular placement could reduce muscle proliferation during the period over which the vessel's endothelium reestablishes continuity and the cellular events surrounding acute injury have subsided.

Figure 16:
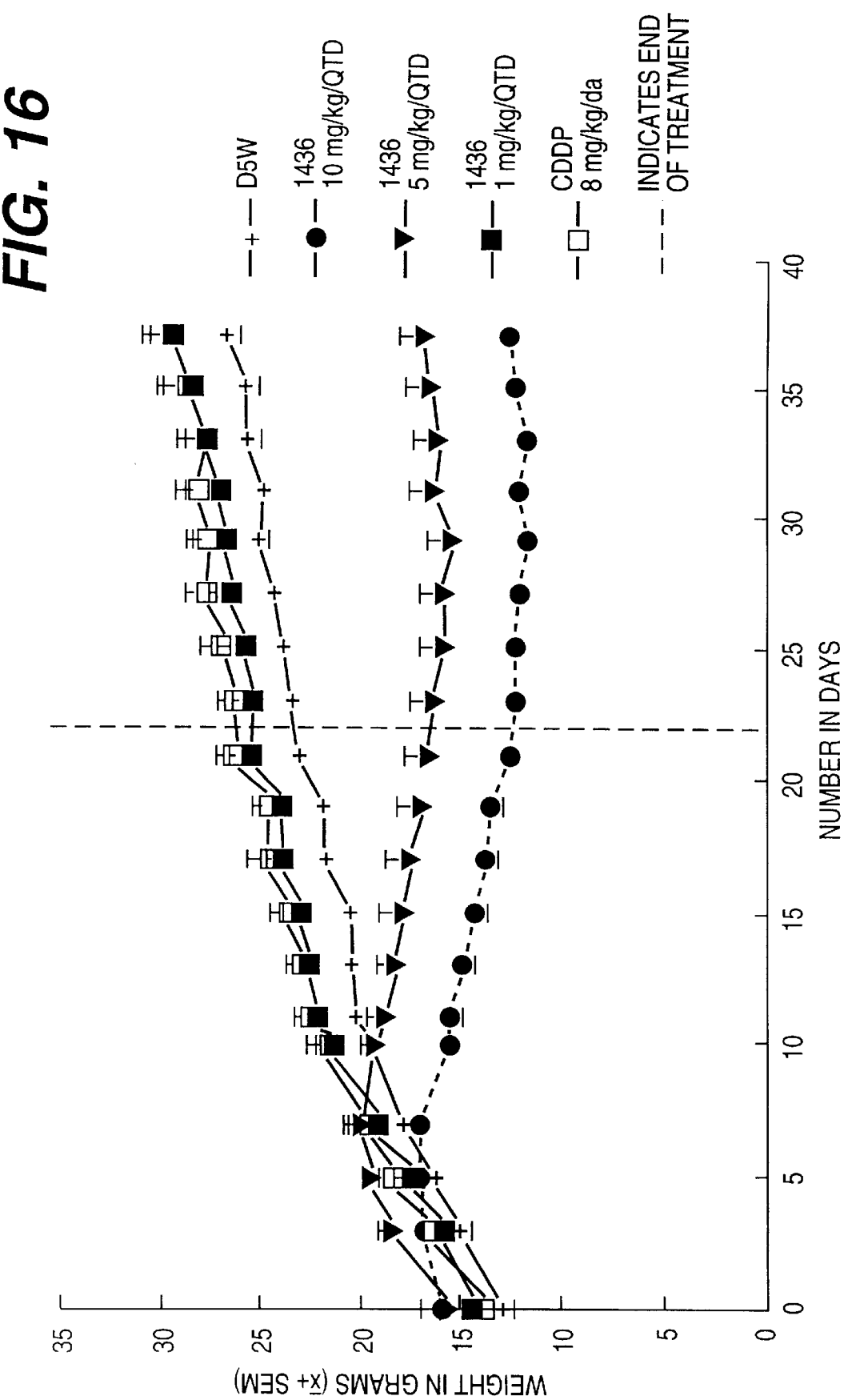
FIG. 16 illustrates that compound 1436 suppresses the growth of mice in a dose-dependent fashion.

Effect on Growth and Weight Gain:

During evaluation of the physiological effects of compound 1436 in normal growing mice, it became evident that this steroid suppresses both linear growth and weight gain in growing mice in a dose-dependent fashion. Animals were dosed QTD (i.p.) starting on Day 1. FIG. 16 shows that C57B mice treated with 10 mg/kg, QTD i.p., 5 mg/kg QTD i.p., and 1 mg/kg QTD i.p. exhibited a dose dependent reduction in growth. After 6 doses, growth of the animals receiving 10 mg/kg QTD had been suppressed to a degree that growth was almost completely inhibited over about 1 month from the initiation of treatment. Animals receiving 5 mg/kg QTD experienced about a 50% reduction in growth, compared to untreated controls, while animals receiving 1 mg/kg QTD were affected by about 10%. Striking was the apparent health of the treated animals—all were active, normally proportioned, not-cachectic, and in excellent apparent clinical health. They appeared very much like hypophysectamized animals might appear.

Compound 1436 clearly inhibits the growth of many different types of cell and tissue and this, to some extent, explains the profound suppression of growth observed. However, the extraordinary good health of these animals suggests that an additional mechanism must be involved— one involving inhibition of pituitary function. Compound 1436 is believed to partially inhibit secretion of anterior pituitary hormones, resulting in the observed growth suppression.

This property of compound 1436, regardless of its precise mechanism, suggests that it can produce an unprecedented form of antiproliferative effect when administered to an animal. It will not only inhibit growth-factor induced cellular proliferation by acting on the proliferating cell, but also inhibit growth-promoting hormone secretion at a central, endocrine level. Thus, compound 1436 places the animal in a "growth-inhibited" state. In such a state, malignant cells will not receive optimal exogenous hormonal stimulation from hormones such as growth hormone, and perhaps LH and FSH. Secretion of hormones such as estrogen and progesterone, as well as insulin, are likely to be dysregulated. Virally infected cells will be placed under physiologically unfavorable conditions, and the efficiency of viral infection should be dramatically reduced. Immunologically foreign cells, suppressed in growth, should be cleared by existing immune systems, now giving a chance to catch up kinetically to these "foreign" cells.

Effect on Arterial Resistance:

Compound 1436 has also been found to reduce arterial resistance in the rat after intravenous (i.v.) administration. A 200-g rat was catheterized in the right carotid artery, and the compound was introduced over a ten-second period to a total dosage of 5 mg/kg. Within 30 seconds, the mean arterial pressure had fallen from about 100 mm Hg to about 70 mm Hg, with a marked reduction in pulse pressure from about 40 mm to about 10 mm. Despite the fall in blood pressure, no significant increase in heart rate was observed. If cardiac output was basically unaffected, reduction in blood pressure would have resulted principally from a reduction in system resistance.

The effect was followed for 30 minutes, without significant change. At that time, 40 μg of noradrenaline was introduced. An almost immediate increase in blood pressure was observed, with an associated increase in pulse pressure. This data demonstrate that the effect of compound 1436 is readily reversible by standard pharmacological practice.

The ability of compound 1436 to reduce arterial resistance and arterial blood pressure indicates its application as an antihypertensive agent. Because it does not appear to induce a compensatory tachycardia, the net effect is to reduce cardiac afterload. A physiological consequence of this type of cardiovascular effect would be to slow the process of cardiac hypertroph and arteriolar smooth muscle proliferation. Because of these properties, compound 1436 should be an effective treatment of congestive heart failure, where reduction in afterload would be desired. Its rapidity of action and ready reversibility, along with minimal tachycardic effect, make the compound a valuable therapeutic agent.

Thus, compound 1436 represents an antiproliferative and therapeutic agent with previously unknown and valuable properties and utilities. It clearly can be utilized in disorders where suppression of growth of specific tissues or entire organ systems is desired.

Suppression of Cardiotoxic Effects of Ischemia:

It has been suggested that inhibitors of the NHE family could play a therapeutic role in the treatment of cardiac ischemic states. These states occur after heart attacks, during heart failure, and in the course of transplantation of an organ from donor to recipient.

To determine if compound 1436 has such utility, the following experiment was performed. The heart of a juvenile *Xenopus laevis* frog was dissected from the living animal. The heart was placed into a Petri dish containing Krebs-Ringer buffer with adrenaline 50 μg/ml, and examined with the naked eye. At room temperature, the heart continued beating in a coordinated fashion (atrial beat followed by ventricular beat) for about one hour. In the presence of 10 μg/ml of compound 1436, spontaneous beating persisted up to 24 hours. The atrial pacemaker and the conduction of the atrial beat to the ventricle remained vigorous over this period.

Although the precise mechanism explaining this phenomenon of persistence of cardiac activity ex vivo is not fully understood, it is believed that compound 1436, by inhibiting NHE3 and NHE5, prevents accumulation of intracardiac calcium by blocking these NHEs. It is the current understanding in the art that intracellular acid accumulating during ischemia is exchanged by the NHE for extracellular sodium. In turn, the sodium driven into the cell is subsequently excreted in exchange for extracellular calcium through the action of a sodium/calcium exchanger. It is the calcium entering via this route that leads to cardiac death and cardiac arrhythmia. By blocking the NHE, compound 1436 prevents protons or acid from leaving the cardiac cell, reducing energy consumption and work output, effects which are protective to the cell, along with preventing the ultimate entry of damaging calcium.

Anti-Proliferative Assays and Tumor Growth Suppression Assays as Characterizing Assays:

As above, the tadpole assay was used to screen for additional compounds. In the presence of 10 μg/ml of compound 1436, the stage 59–60 Xenopus tadpole experiences dramatic disruption of melanocytes over its head, trunk, and tail, along with depression of its nervous system. No effects are observed on epithelial cell integrity, vascular flow, erythrocyte volume, tissue integrity, muscle fiber striation, or GI tract activity.

Using the tadpole assay to screen for functionally similar compounds, compounds 353, 371 and 413 were found to produce effects like those produced by compound 1436. Of these, compound 353 is especially preferred because of its ease of synthesis as described above. This compound was also found to exhibit other advantageous properties.

Using the growth suppression methods set forth above, it was determined that compound 353 exhibits potent activity against melanoma and a number of cancer cells as set forth below:

TABLE 12

| CYTOTOXIC ACTIVITY OF COMPOUND 353 AGAINST CANCER CELLS | |
|---|---|
| Cell | IC$_{50}$ (μg/ml) |
| Human melanoma WM 1167 | 3.0 |
| Lewis Lung carcinoma | 1.9 |

Figure 17A:
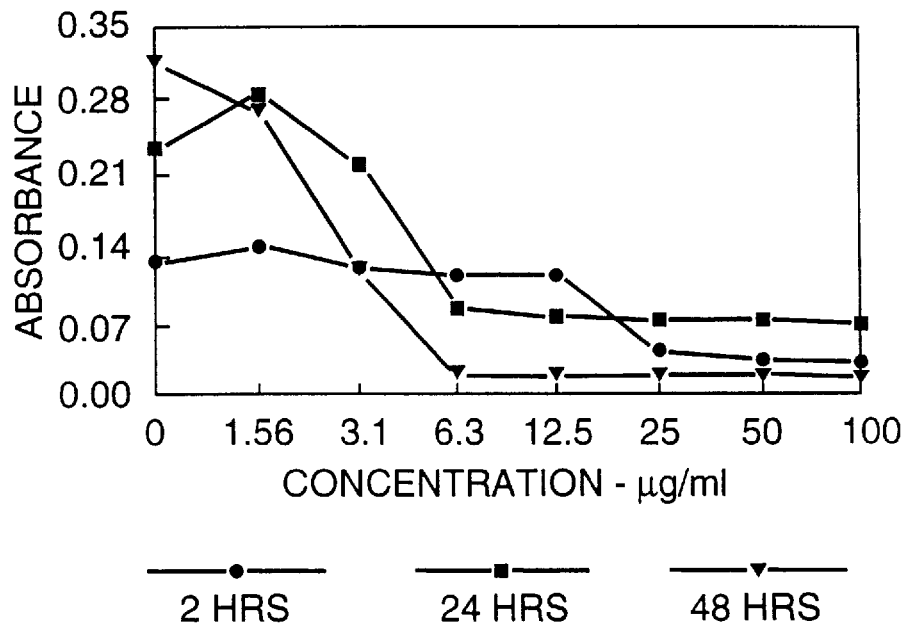
Figure 17B:
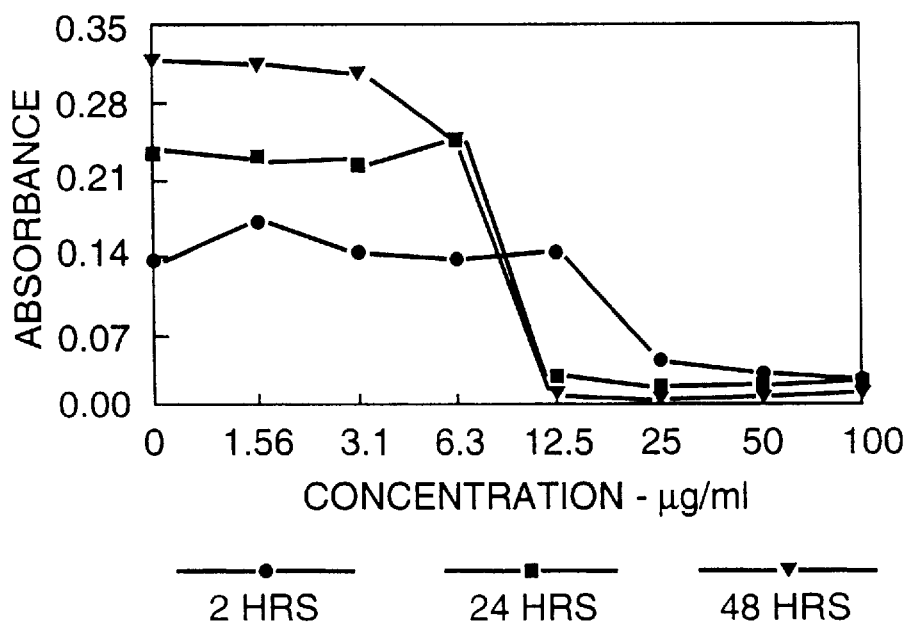

In addition, using the method of Baker et al., *Cancer Res.* 53, 1994, 3052–3057, it was observed that the effect of compound 353 on the growth of melanoma is most pronounced over 48 hours, with less of an effect noted within the first 12 hours of incubation, as shown in FIG. 17A. For comparative purposes, the effect of squalamine in human melanoma is shown in FIG. 17B.

Analysis of the cells exposed to compound 353 reveals that apoptotic cell death has been induced. Thus, this aminosterol exhibits the same highly selective mechanism of killing as does compound 1436.

Although as set forth above, compound 1436 exhibits melanocyte disruptive activity in the tadpole, it causes vitelline capillary regression with about the same potency as squalamine. In contrast, compound 353 exhibits no effect on the chick embryo capillary bed. Thus, it appears that compound 353 inhibits NHE5 to a greater extent than NHE3, with even greater selectivity than compound 1436. Compound 353 demonstrates that it is possible to create aminosterols that exhibit greater specificity than naturally occurring molecules.

Compound 1437 (Fraction 4) contains an unusual ergosterol-like side chain. This molecule can be distinguished readily from all other steroids extracted from shark on the basis of its dramatic effect on the embryonic epithelium covering the tadpole tale.

Using the tadpole assay described above, within 60 minutes of exposure to this steroid at 10 μg/ml, the larval skin was observed to shed off in a sheet. The speeded appearance of the process suggests that an NHE expressed by this epithelial tissue is the target. Since NHE activity and cell membrane proteins involved in adhesion cross-communicate (Schwartz et al., *Proc. Nat'l. Acad. Sci.* 888, 7849–7853), it is proposed that inhibition of NHE on the epithelium results in disruption of cellular contacts between the epithelium and its substratum, leading to a shedding effect.

Using the assay described above, the anticancer effects of compound 1437 against several cancer lines was assessed. Compound 1437 was found to exhibit anticancer activity against the human ovarian carcinoma, SKOV3. Thus, compound 1437 should find use in the treatment of carcinomas exhibiting a sensitive phenotype.

As the study above demonstrates, compound 1437 targets a "mesothelium-like" epithelial layer, a skin layer that is comprised of only one cellular layer. Such a layer resembles epithelial surfaces such as the human peritoneum, synovium, pericardium and ependyma. Accordingly, compound 1437 should exhibit antiproliferative effects on these tissues and malignancies which derive from them. In addition, these tissues can support viral infections, and therefore in these instances the compound should provide therapeutic antiviral benefit.

By use of the Xenopus tadpole assay, it is possible to identify compounds that exhibit little chemical resemblance to compound 1437, but produce the same pharmacological effect with respect to epithelial shedding. Using such a method, it was found that compounds 409, 410, 416, 431, 432 and 433 are functionally similar to compound 1437.

Steroid 1360 (Fraction 2) contains a side chain bearing a keto group on carbon 24 and a sulfate on the C 27 hydroxyl. Although somewhat similar in structure to squalamine, it exhibits a dramatically different pharmacologic profile in both the tadpole and chick embryo assays.

When stage 59–60 tadpoles were introduced into a 10 μg/ml solution of compound 1360, extensive vasocclusion occurred within 60 minutes throughout the tail—the distal portions to a greater extent than the proximal. Occlusion occurred due to the visible swelling of erythrocytes followed by rupture and release of nuclei. Nuclei were shuttled by the design of the vascular bed into distal arteries and veins, which can be analogized to a coin separating machine separating coins of different size and weight into specific collecting tubes. As the nuclei pooled within these vessels, blood flow stopped proximally. Within 20–30 minutes after nuclear plugs formed, tissue surrounding these plugs began to break down. It appeared as if the nuclei were releasing hydrolytic enzymes that were essentially dissolving the ground substance holding these tissues.

In the chick embryo assay, application of compound 1360 produced a different effect than seen in the tadpole. Within 20 minutes, the blood circulating through the embryonic vessels exhibited a brighter red color, reflecting a higher degree of oxygenation than the red cells not exposed to the compound. Although many numerous mechanisms might explain this effect, it is believed that the red cell of the chick is experiencing a more alkaline internal pH after exposure to compound 1360. This could arise through activation of the NHE of this cell. Furthermore, activation of the exchanger would also cause cellular swelling—a phenomenon observed in tadpole.

It is known that the nucleated erythrocytes of amphibia and fish (and probably birds) express a specific NHE, termed NHE1-beta. Unlike all others characterized, this exchanger is activated by cAMP and is influenced by the state of hemoglobin oxygenation. This data suggest that compound 1360 will be shown to activate this exchanger. Furthermore, the chemical structure of the compound makes it ideally suited to function in the suggested fashion. It has been discovered that, under slightly alkaline conditions, compound 1360 undergoes a dehydration of the 27 hydroxyl, loss of sulfate, and generation of the corresponding 27-ene, as set forth in the scheme below:

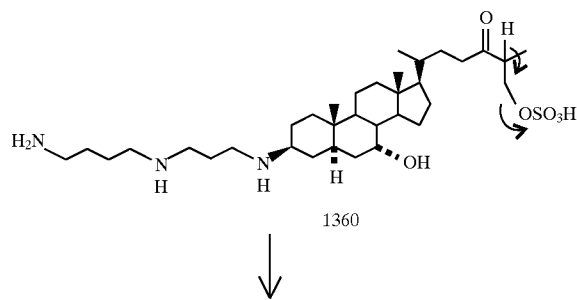

1360

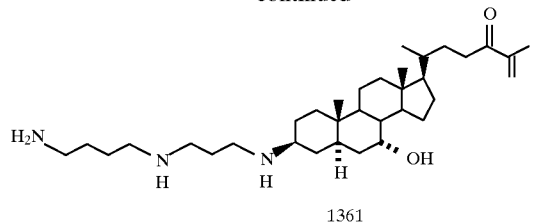

1361

Thus, as the alkalinity of the interior of a cell increases, the lifetime of compound 1360 decreases, thereby providing an extraordinary form of "feedback." It is possible that compound 1361, the product of this hydrolytic conversion, is inhibitory to the same NHE.

The data demonstrate that compound 1360 clearly interacts with a NHE present on embryonic stage blood cells. Since the human fetus generates nucleated red cells comparable in size to those of the birds, fish, and amphibia, it is thought that certain human blood cells, perhaps fetal, will also represent cellular targets of this compound. Activation of the fetal NHE might find use in strategies designed to protect the fetus from hypoxic damage.

The full scope of applications for compound 1360 awaits description of the distribution of the erythrocyte NHE isoform in man. However, it appears to be stimulatory activity in some settings, rather than an inhibitor of an NHE. In any event, compound 1360 could be used for the following: antibacterial, antifungal, antiviral, etc.; fetal distress treatment; and hematologic malignancies treatment.

Although the chemical structure of Fraction 3 (FX 3) is yet to be fully determined, from its thin layer chromatographic properties it has a spermine associated with the steroid, much like compound 1436. This steroid has a profound effect on the embryonic skeletal muscles of the tadpole.

In the tadpole assay, within 1 hour after exposure, leakage of brown pigment from the tail muscle bundles of stage 59–60 tadpole was observed. Cross striations became fuzzy and obscure. Heartbeat and other functions, including muscle activity in the limbs, were unaffected. These observations suggest that FX 3 is targeting primitive mesenchyme, including muscle.

If the observations of the tadpole extend to man, then FX 3 should profoundly affect the proliferation of certain mesenchymal cells. Thus, it would have use in the treatment of a variety of cancers of mesenchymal origin, such as cancers of striated muscle, cartilage, fibroblastic tissues, bone, and fatty tissue.

In addition, if proliferation of fibroblasts is affected, then FX 3 would have application in the control of fibroblastic proliferation in settings where this process is unwanted. Thus, scarring after CNS injury might be prevented. Unwanted scarring after surgery at sites complicated by fibrosis would be serious therapeutic targets. Generalized conditions of fibroblastic proliferation, such as seen in heart, kidney and liver disease, might be allayed.

If proliferation of muscle is inhibited, FX 3 could find use in the inhibition of hyperplastic diseases of muscle, such as in certain forms of cardiac disease.

Through use of the Xenopus tadpole assay, several aminosterols have been identified as exhibiting pharmacologic activity similar to that seen for FX 3. These compounds include compounds 370, 412, 458, 459, 465 and 466. These compounds in general share the spermine moiety. They are simpler chemically than squalamine and offer a less expensive route to drug design than the naturally occurring steroids.

The structure of the Fraction 1 (FX 1A) steroid is shown above. It appears to undergo conversion to another molecule (FX 1B) rapidly in water. FX 1A exerts a distinctive pharmacologic effect on the Xenopus tadpole using the assay set forth above.

Within several hours of introduction of this steroid into the water surrounding the tadpole, fecal elimination is dramatically increased. Since the GI tract of a number of vertebrates utilizes NHE in the control of gut fluid secretion, it is believed that Fraction 1 acts on such an NHE. The increase in fecal material could correspond to "diarrhea," a condition which occurs in man when the colonic NHE is inhibited. Since this steroid has little effect on overall activity, muscle integrity or viability of any visible tissue, it might serve a physiological function such as regulation of sodium-water exchange.

Although the uses will be clearer after the steroid and target are better characterized, the tadpole data suggest that Fraction 1 will find use in the modulation of sodium/proton exchange in certain physiological derangements. These include treatment of hypertension, cystic fibrosis and constipation.

Because of its effects on bowel fluid dynamics, this agent may be as a antimicrobial—one which would effect killing of susceptible bacteria, parasites, fungi, etc., while promoting the discharge of the infectious load from the gut. Fraction 1 may also find use as an effective antibacterial, antiparasitic or antifungal agent.

Through the use of the Xenopus tadpole assay, aminosterols with pharmacologic activity similar to Fraction 1 have been identified. Surprisingly, these compounds have been found to include compound 1363 and compound 414. Although these compounds exhibit potencies comparable to that of Fraction 1, they have chemically simpler structures.

Preliminary data has revealed the presence of a least two hydrophilic steroids eluting slightly ahead of Fraction 1 on the reversed-phase separation depicted in FIG. 9. The structures of these steroids are presented below.

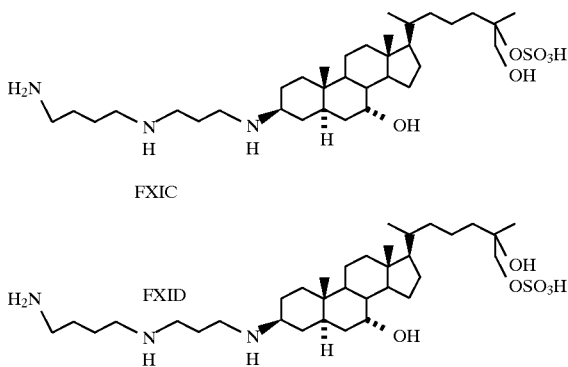

FX1C and FX1D are seen to be steroids with a single sulfate like squalamine and an additional hydroxyl, resembling compound 1437.

Additional Aminosterol Structures:

From the diverse aminosteroids isolated from Squalus acanthias, it is possible to predict the existence of related aminosterols not as yet isolated from this animal's tissues. These sterols can be deduced to exist in vertebrate tissues based on the structures determined to date and the known biochemical transformations the cholesterol side chain can undergo (Tammar, "Bile Salts in Fishes," *Chemical Zoology*, (eds. Florkin et al.), Academic Press, 1974, 595–612).

Thus, based on the existence of squalamine, which bears a 24 sulfated hydroxyl, one should be able to find other derivatives with the squalamine steroidal nucleus and aminosterol portion, but differing in the position of the sulfated hydroxyl on the side chain as shown below. Since hydroxylation can occur on carbons 25, 26 or 27, and since each would represent a stereospecific chemical entity, it is reasonable to expect their existence in nature and to assume they would exhibit distinct pharmacological properties.

Similarly, the existence of steroids bearing a single sulfate along with a second hydroxyl in the cholesterol side chain suggests potential diversity in the pattern of side-chain sulfation and single-site hydroxylation. Thus, aminosterols likely exist in nature where sulfation is found on carbons 24, 25, 26 or 27. In turn, each of these four sulfated aminosterols can be hydroxylated at available carbons 24, 25, 26 and 27. At least the following steroids may be isolated from natural products, based on inductive logic and the data revealed herein:

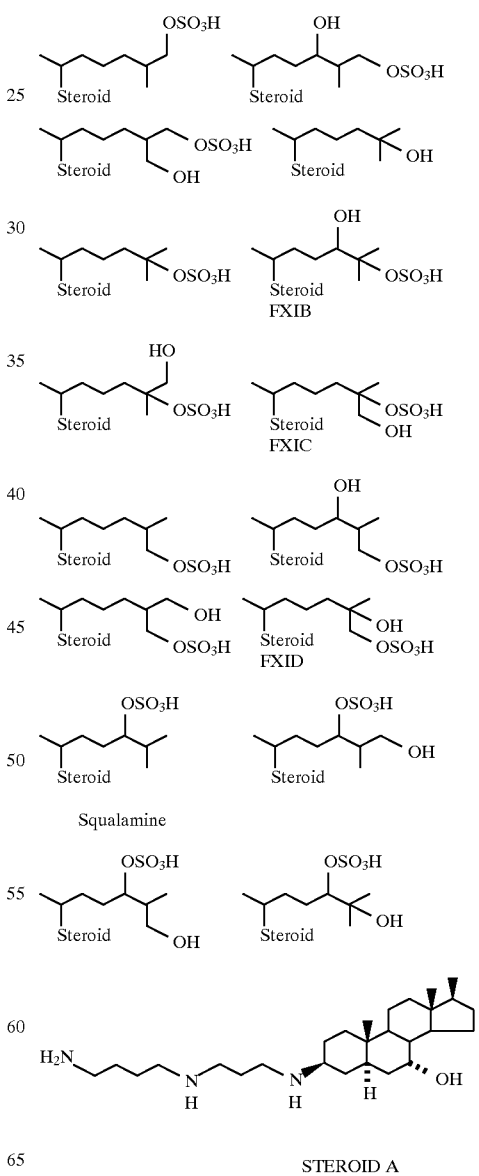

-continued
Steroids Predicted to Exist Based on Steroids Isolated to Date

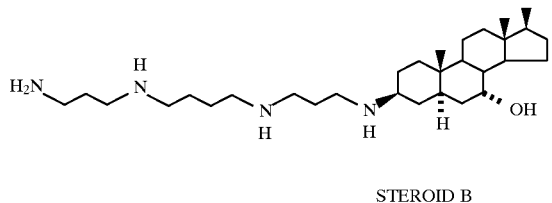

STEROID B

Structure-Activity Considerations for NHE Inhibitors:

Based on the information given above, key structural elements of the aminosterol inhibitors of the sodium/proton exchangers can now be deduced. The key core structure contains a steroid nucleus and a distinctive side chain. An aminosterol portion specifies interaction of the molecule with a NHE. The side chain, bearing free or sulfated hydroxyl groups, determines the specificity for a specific NHE isoform. In addition, the presence of spermine or spermidine attached to the steroid extends the spectrum of activity. Based on this generalization it can be readily seen that the structure of the side chain imparts great specificity.

Thus, other synthetic steroidal NHE inhibitors can be designed with great pharmacological specificity by considering the modular nature of the molecule. Chemical entities which mimic the aminosterol in shape and molecular surface characteristics will interact with the NHE family. Such chemical mimics of the steroidal nuclei are known and widely used in the synthesis of non-steroidal estrogen agonists and antagonists. Coupling of specific cholesterol side chains to these steroidomimetic structures will in turn establish specificity for individual NHE isoforms.

Antimicrobial Activity:

The aminosterol NHE inhibitors represent a class of antibiotics based on mechanism of action. Because these agents also interact with specific NHE isoforms in human tissues, prudent selection of an antibiotic of this class can eliminate undesirable side effects, due to host NHE inhibition, or potentiate the therapeutic intent. Thus, use of an agent like compound 1436 would suppress lymphoid proliferation during active treatment of an infection. Oral administration of Fraction 1 may increase bowel fluid transit as it kills parasitic targets. An effective antifungal agent can be designed further to increase specificity for its pathogenic target over sensitive vertebrate isoforms.

As seen in Table I at the end of this specification, the antibacterial/antifungal spectrum differs from compound to compound. Thus, it is possible to achieve an antimicrobial steroid with or without squalamine-like pharmacological activity.

As set forth in Table II, which follows Table I, the activities of natural and synthetic aminosterols in the different assays vary. In light of the foregoing, it is now possible to screen for steroids with or without squalamine-like pharmacological activity.

Selection of NEE Isoform:

Through the use of molecular biological techniques, it is possible to determine which NHE isoforms are expressed in specific cells, such as malignancies. Human melanoma expresses NHE1, NHE3 and NHE5, and human adenocarcinoma expresses principally NHE3 (see Table 8).

Thus, treatment of this type of adenocarcinoma might most effectively be accomplished with the use of a more specific NHE3 inhibitor, such as squalamine or compound 319. In contrast, melanoma expresses considerable amounts of NHE5 along with NHE3. Hence, treatment of this malignancy should include an inhibitor of both NHE3 and NHE5, such as compound 1436, alone or in combination with squalamine.

In summary, the invention allows for the utilities of the aminosterol NHE inhibitors to be established through diagnostic evaluation of the NHE isoforms expressed in the target tissues. Diagnostic approaches can include immunological detection of the specific NHE isoform protein or a molecular biological procedure such as PCR, utilizing specific sequence information, and standard techniques.

Thus, other embodiments of the invention will be apparent to those skilled in the art from consideration of the specification and practice of the invention. The embodiments and preferred features described above should be considered as exemplary, with the invention being defined by the appended claims.

TABLE I

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| MSI-1240A | 4 | >256 | >256 | 64 |
| MSI-1241A | 16 | >256 | >256 | >256 |

TABLE I-continued

ANTIBIOTIC ACTIVITY OF NATURAL AND SYNTHETIC AMINOSTEROLS

| Structure | Antibiotic Activity MIC Values (µg/mL) | | | |
|---|---|---|---|---|
| | S. aureus | E. coli | P. aerug | C. albicans |
| MSI-1232 | 4–16 | 32 | 128 | 64 |
| MSI-1239A | 8–16 | 64 | 128 | 64 |
| Cmpd. 303 | 8 | 128–256 | 128 | 256 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| MSI-1256 | 0.5–1 | 2–4 | 16 | 8 |
| Compound 304 | 2–4 | 128 | 128 | 128 |
| Compound 319 | 64 | 32–64 | 32 | 8 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 318 | 128 | 32 | 64 | >256 |
| Compound (unlabeled) | 16 | 128 | 64 | 32 |
| Compound 354 | 8 | 64–128 | 64 | 16–32 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| 387 | 16–32 | 128 | 256 | 64 |
| 388 | 2–4 | 4–8 | 16 | 16 |
| Compound 380 | 4–8 | 32 | 64 | 32 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 381 | 32 | 64 | 32 | 128 |
| Compound 382 | 16 | 64 | 32 | 32 |
| Compound 393 | 2 | >256 | >256 | 32 |

TABLE I-continued

ANTIBIOTIC ACTIVITY OF NATURAL AND SYNTHETIC AMINOSTEROLS

| Structure | Antibiotic Activity MIC Values (µg/mL) | | | |
|---|---|---|---|---|
| | S. aureus | E. coli | P. aerug | C. albicans |
| Compound 394 | 4 | 64 | 64 | 32 |
| Compound 395 | 4 | 32 | 64 | 64 |
| Compound 396 | 2–4 | 64 | 128 | 16 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 397 | 16 | 32–64 | 16 | 32 |
| MSI-1350A | 4 | 32–64 | 256 | 64 |
| MSI-1351A | 16 | 64 | 128 | 128 |

TABLE I-continued

ANTIBIOTIC ACTIVITY OF NATURAL AND SYNTHETIC AMINOSTEROLS

| Structure | Antibiotic Activity MIC Values (µg/mL) | | | |
|---|---|---|---|---|
| | S. aureus | E. coli | P. aerug | C. albicans |
| Compound 355 | 64 | 256 | >256 | 256 |
| Compound 356 | 4 | 32–64 | 64 | 64 |
| Compound 1360 | 8 | 128 | 128 | 32 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 1361 | 4 | 32 | 128 | 4 |
| Compound 1363 | 2 | >256 | >256 | 2 |
| Compound 1364 | 2 | >256 | >256 | 2 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 370 | 4 | 32 | 64 | 2 |
| Compound 371 | 4 | 64 | 64 | 2 |
| Compound 409 | 32 | 64 | 128 | 16 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 410 | 16 | 16 | 32 | 16 |
| Compound 411 | 8 | 64 | 64 | 2 |
| Compound 412 | 8 | 64 | 8 | 8 |

TABLE I-continued

ANTIBIOTIC ACTIVITY OF NATURAL AND SYNTHETIC AMINOSTEROLS

| Structure | Antibiotic Activity MIC Values (µg/mL) | | | |
|---|---|---|---|---|
| | S. aureus | E. coli | P. aerug | C. albicans |
| Compound 413 | 8 | 256 | 64 | 32 |
| Compound 414 | 32 | 64 | 64 | 64 |
| Compound 415 | 128 | 128 | 256 | 256 |

TABLE I-continued

ANTIBIOTIC ACTIVITY OF NATURAL AND SYNTHETIC AMINOSTEROLS

| Structure | Antibiotic Activity MIC Values (µg/mL) | | | |
|---|---|---|---|---|
| | S. aureus | E. coli | P. aerug | C. albicans |
| Compound 416 | 8 | 8 | 16–32 | 32 |
| Compound 417 | 16–32 | 64 | 128 | 32 |
| Compound 431 | 16 | 32–44 | 128 | 8 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 432 | 1 | 8–16 | 64 | 2–4 |
| Compound 433 | >256 | >256 | 128 | >256 |
| Compound 1436 | | | | |

TABLE I-continued

ANTIBIOTIC ACTIVITY OF NATURAL AND SYNTHETIC AMINOSTEROLS

| Structure | Antibiotic Activity MIC Values (µg/mL) | | | |
|---|---|---|---|---|
| | S. aureus | E. coli | P. aerug | C. albicans |
| Compound 1437 | | | | |
| Compound 448 | 2 | 16 | 8 | 8 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 449 | 4 | 8–16 | 4 | 4 |
| Compound 458 | 4 | 32 | 64 | 2 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 459 | 1–2 | 32 | 64 | 2 |
| Compound 465 | 2–4 | 32 | 128 | 4 |

TABLE I-continued

ANTIBIOTIC ACTIVITY OF NATURAL AND SYNTHETIC AMINOSTEROLS

| Structure | Antibiotic Activity MIC Values (μg/mL) | | | |
|---|---|---|---|---|
| | S. aureus | E. coli | P. aerug | C. albicans |
| Compound 466 | 2 | 32 | 32 | 2 |
| Compound 467 | 16 | 16 | 8 | 4 |

TABLE II

ACTIVITY OF NATURAL AND SYNTHETIC AMINOSTEROLS IN CHICK EMBRYO AND TADPOLE ASSAYS

V = vascular; M = melanocytes; E = epithelial;
TB = tissue breakdown, GI = gastro intestinal,
MUS = muscle, TOX = lethality at 2 hrs.

| Structure | Chick embryo diss. assay ($\mu$g) | Tadpole (10 $\mu$g/mL) | | | | | | Cord Formation ($\mu$g/mL) | HM MTT assay ($\mu$g/mL) | LLC MTT ($\mu$g/mL) |
|---|---|---|---|---|---|---|---|---|---|---|
| | | V | M | E | TB | GI | Mus | Tox | | |
| 303 | >10 | − | | | | | | | | | |
| 318 | >10 | − | − | − | − | − | − | − | | | |
| 319 | 0.001 | + | − | − | − | − | − | − | | 13.8 | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay ($\mu$g) | Tadpole (10 $\mu$g/mL) V | M | E | TB | GI | Mus | Tox | Cord Formation ($\mu$g/mL) | HM MTT assay ($\mu$g/mL) | LLC MTT ($\mu$g/mL) |
|---|---|---|---|---|---|---|---|---|---|---|---|
| 353 | >1 | − | + | − | − | − | − | + | 10 | 3.0 | 3 |
| 354 | >10 | − | − | − | − | − | − | − | | | |
| | | + | − | − | − | − | − | ± | | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Minimum Effective Concentration (μg/mL) | | | | | | | | | | |
|---|---|---|---|---|---|---|---|---|---|---|---|
| | Chick embryo diss. assay (μg) | V | M | E | Tadpole (10 μg/mL) TB | GI | Mus | Tox | Cord Formation (μg/mL) | HM MTT assay (μg/mL) | LLC MTT (μg/mL) |
| 356 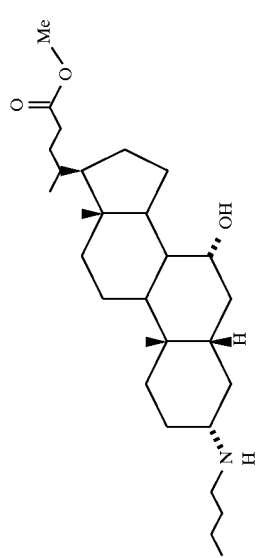 | >10 | + | – | – | – | – | – | + | | | |
| 370 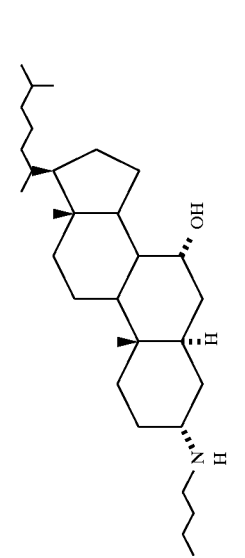 | 1–10 | – | + | – | – | – | + | + | | 4.0 | |
| 371 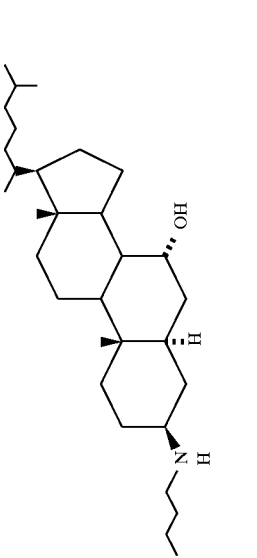 | | – | – | – | – | – | – | + | | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (µg) | Tadpole (10 µg/mL) V | M | E | TB | GI | Mus | Tox | Cord Formation (µg/mL) | HM MTT assay (µg/mL) | LLC MTT (µg/mL) |
|---|---|---|---|---|---|---|---|---|---|---|---|
| 364 | 1 | + | - | ± | - | - | - | + | | | |
| 396 | 10 | - | - | - | - | - | - | + | | | |
| 397 | 1 | - | - | - | - | - | - | + | | | |

TABLE II-continued

ACTIVITY OF NATURAL AND SYNTHETIC AMINOSTEROLS IN CHICK EMBRYO AND TADPOLE ASSAYS

V = vascular; M = melanocytes; E = epithelial;
TB = tissue breakdown, GI = gastro intestinal,
MUS = muscle, TOX = lethality at 2 hrs.

| Structure | Chick embryo diss. assay ($\mu$g) | Tadpole (10 $\mu$g/mL) | | | | | | Cord Formation ($\mu$g/mL) | HM MTT assay ($\mu$g/mL) | LLC MTT ($\mu$g/mL) |
|---|---|---|---|---|---|---|---|---|---|---|
| | | V | M | E | TB | GI | Mus | Tox | | | |
| 399 | >10 | - | - | - | + | - | - | - | | | |
| 409 | >1 | - | - | + | + | - | - | + | | | |
| 410 | 0.01 | ± | - | + | + | - | - | + | 10 | 2.6 | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (μg) | Tadpole (10 μg/mL) V | M | E | TB | GI | Mus | Tox | Cord Formation (μg/mL) | HM MTT assay (μg/mL) | LLC MTT (μg/mL) |
|---|---|---|---|---|---|---|---|---|---|---|---|
| 381 | >10 | − | − | − | − | − | − | + | | | |
| 382 | 0.01 | − | − | − | − | − | − | + | | 58.6 | |
| 393 | >10 | − | ± | − | − | − | − | + | | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (μg) | Tadpole (10 μg/mL) | | | | | | | Cord Formation (μg/mL) | HM MTT assay (μg/mL) | LLC MTT (μg/mL) |
|---|---|---|---|---|---|---|---|---|---|---|---|
| | | V | M | E | TB | GI | Mus | Tox | | | |
| 394 | >10 | − | | | | | | | | | |
| 395 | >10 | − | − | − | − | − | − | + | | | |
| 459 | >1 | − | − | ± | − | − | + | + | | 5.0 | |

TABLE II-continued

ACTIVITY OF NATURAL AND SYNTHETIC AMINOSTEROLS IN CHICK EMBRYO AND TADPOLE ASSAYS

V = vascular; M = melanocytes; E = epithelial;
TB = tissue breakdown, GI = gastro intestinal,
MUS = muscle, TOX = lethality at 2 hrs.

| Structure | Chick embryo diss. assay (µg) | \multicolumn{6}{c|}{Minimum Effective Concentration (µg/mL)} | Cord Formation (µg/mL) | HM MTT assay (µg/mL) | LLC MTT (µg/mL) |
|---|---|---|---|---|---|---|---|---|---|---|
| | | V | M | E | TB | GI | Mus | Tox | | | |
| 465 | | − | − | ± | − | − | + | + | | | |
| 466 | 1 | − | − | ± | − | − | + | + | | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (μg) | Tadpole (10 μg/mL) V | M | E | TB | GI | Mus | Tox | Cord Formation (μg/mL) | HM MTT assay (μg/mL) | LLC MTT (μg/mL) |
|---|---|---|---|---|---|---|---|---|---|---|---|
| 467 | | - | - | - | - | - | - | + | | | |
| 431 | >1 | ± | - | + | + | - | - | + | | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (µg) | Tadpole (10 µg/mL) V | M | E | TB | GI | Mus | Tox | Cord Formation (µg/mL) | HM MTT assay (µg/mL) | LLC MTT (µg/mL) |
|---|---|---|---|---|---|---|---|---|---|---|---|
| 432 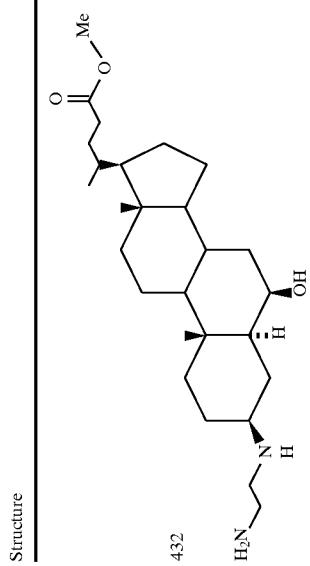 | >1 | − | − | + | − | − | − | + | | | |
| 433 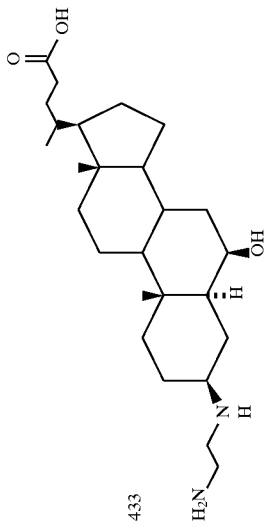 | 1 | − | − | + | + | ± | − | − | | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (μg) | Tadpole (10 μg/mL) V | M | E | TB | GI | Mus | Tox | Cord Formation (μg/mL) | HM MTT assay (μg/mL) | LLC MTT (μg/mL) |
|---|---|---|---|---|---|---|---|---|---|---|---|
| 448 | 1 | ± | - | + | + | - | - | + | | | |
| 449 | >1 | - | - | ± | ± | - | - | + | | | |
| 458 | >1 | - | - | ± | - | - | + | + | | 6.8 | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (µg) | Tadpole (10 µg/mL) V | M | E | TB | GI | Mus | Tox | Cord Formation (µg/mL) | HM MTT assay (µg/mL) | LLC MTT (µg/mL) |
|---|---|---|---|---|---|---|---|---|---|---|---|
| 411 | >1 | ± | - | - | - | - | - | + | 10 | | |
| 412 | 1 | - | - | - | - | - | + | + | >10 | 18.1 | |
| 413 | >1 | - | + | - | - | - | - | + | >10 | | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay (μg) | Tadpole (10 μg/mL) | | | | | | | Cord Formation (μg/mL) | HM MTT assay (μg/mL) | LLC MTT (μg/mL) |
|---|---|---|---|---|---|---|---|---|---|---|---|
| | | V | M | E | TB | GI | Mus | Tox | | | |
| 414 | >1 | – | – | – | – | + | – | – | | | |
| 415 | >1 | – | – | – | – | – | – | – | >10 | | |
| 416 | >1 | ± | – | + | + | – | – | + | | 2.4 | |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay ($\mu$g) | Minimum Effective Concentration ($\mu$g/mL) | | | | | | | Cord Formation ($\mu$g/mL) | HM MTT assay ($\mu$g/mL) | LLC MTT ($\mu$g/mL) |
|---|---|---|---|---|---|---|---|---|---|---|---|
| | | Tadpole (10 $\mu$g/mL) | | | | | | | | | |
| | | V | M | E | TB | GI | Mus | Tox | | | |
| 417 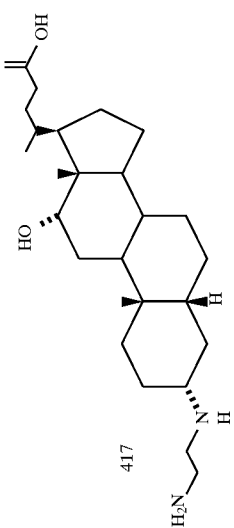 | >1 | – | – | – | – | – | – | – | | | |
| 1256 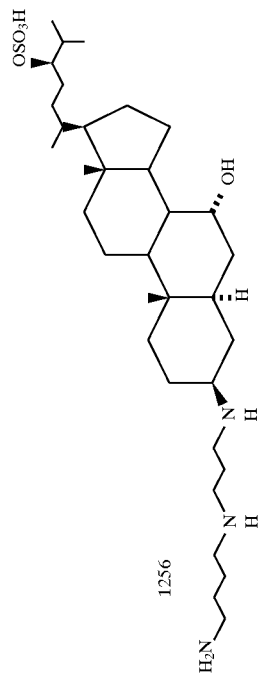 | 0.01 | + | – | – | – | – | – | + | 0.01–0.1 | 7.8 | 13.2 |

TABLE II-continued

ACTIVITY OF NATURAL AND SYNTHETIC AMINOSTEROLS IN CHICK EMBRYO AND TADPOLE ASSAYS
V = vascular; M = melanocytes; E = epithelial;
TB = tissue breakdown, GI = gastro intestinal,
MUS = muscle, TOX = lethality at 2 hrs.

| Structure | Chick embryo diss. assay ($\mu$g) | Tadpole (10 $\mu$g/mL) V | M | E | TB | GI | Mus | Tox | Cord Formation ($\mu$g/mL) | HM MTT assay ($\mu$g/mL) | LLC MTT ($\mu$g/mL) |
|---|---|---|---|---|---|---|---|---|---|---|---|
| 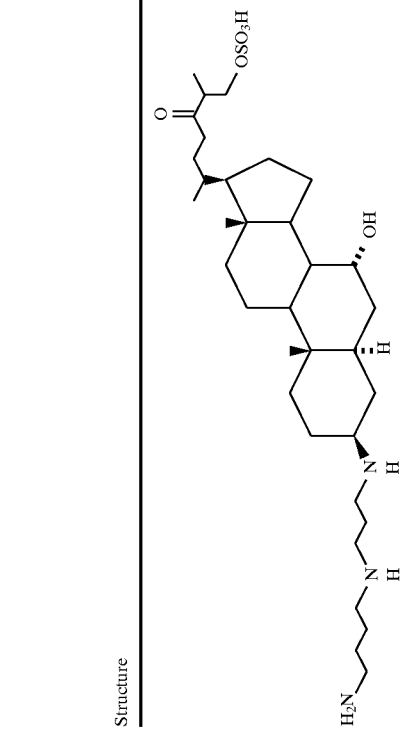 1360 | >10 | - | - | + | + | - | - | - | | | |
| 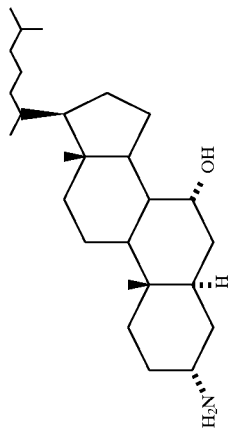 1363 | | - | - | - | - | + | - | - | | | |

TABLE II-continued

ACTIVITY OF NATURAL AND SYNTHETIC AMINOSTEROLS IN CHICK EMBRYO AND TADPOLE ASSAYS

V = vascular; M = melanocytes; E = epithelial;
TB = tissue breakdown, GI = gastro intestinal,
MUS = muscle, TOX = lethality at 2 hrs.

| Structure | Chick embryo diss. assay (µg) | Tadpole (10 µg/mL) V | M | E | TB | GI | Mus | Tox | Cord Formation (µg/mL) | HM MTT assay (µg/mL) | LLC MTT (µg/mL) |
|---|---|---|---|---|---|---|---|---|---|---|---|
| 1436 | 1 | + | + | ± | - | - | - | + | | 6.9 | 16.7 |
| 1437 | >1 | - | - | + | - | - | - | - | | | |

What is claimed is:

1. A compound having the following formula:

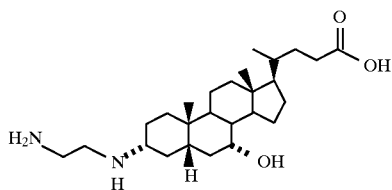  414 or a pharmaceutically acceptable salt thereof.

2. A compound having the following formula:

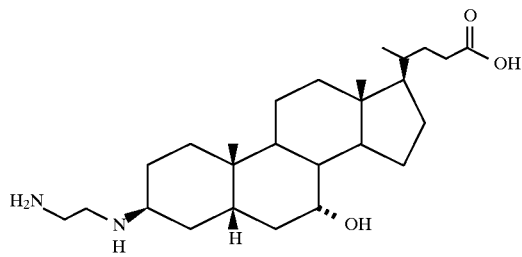  415 or a pharmaceutically acceptable salt thereof.

3. A compound having the following formula:

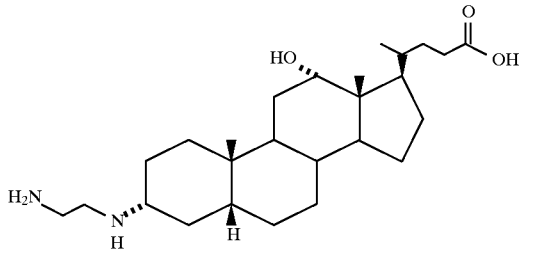  417 or a pharmaceutically acceptable salt thereof.

4. A compound having the following formula:

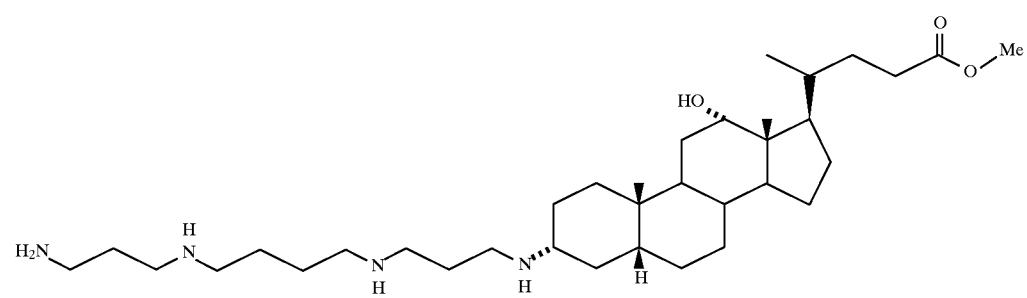  448 or a pharmaceutically acceptable salt thereof.

5. A compound having the following formula:

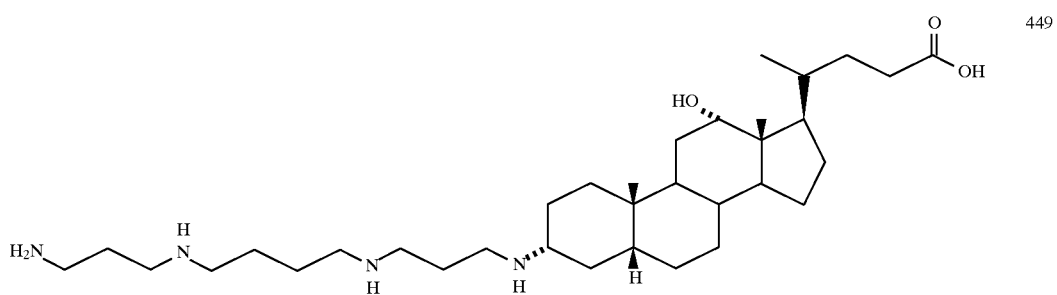  449 or a pharmaceutically acceptable salt thereof.

* * * * *